(12) United States Patent
Caughey et al.

(10) Patent No.: US 8,216,788 B2
(45) Date of Patent: Jul. 10, 2012

(54) DETECTION OF INFECTIOUS PRION PROTEIN BY SEEDED CONVERSION OF RECOMBINANT PRION PROTEIN

(75) Inventors: Byron W. Caughey, Hamilton, MT (US); Ryuichiro Atarashi, Nagasaki (JP); Roger A. Moore, Hamilton, MT (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 305 days.

(21) Appl. No.: 12/177,012

(22) Filed: Jul. 21, 2008

(65) Prior Publication Data

US 2009/0047696 A1  Feb. 19, 2009

Related U.S. Application Data

(60) Provisional application No. 60/961,364, filed on Jul. 20, 2007, provisional application No. 61/021,865, filed on Jan. 17, 2008.

(51) Int. Cl.
| | |
|---|---|
| G01N 33/53 | (2006.01) |
| G01N 33/48 | (2006.01) |
| C12Q 1/00 | (2006.01) |
| C07K 14/435 | (2006.01) |

(52) U.S. Cl. ............ 435/7.1; 435/7.2; 435/4; 435/40.5; 436/172; 530/393

(58) Field of Classification Search ........................ None
See application file for complete search history.

(56) References Cited

U.S. PATENT DOCUMENTS

| | | | | |
|---|---|---|---|---|
| 5,733,758 | A | * | 3/1998 | Nguyen ........................ 435/162 |
| 7,351,526 | B2 | | 4/2008 | Soto et al. |
| 2003/0134340 | A1 | * | 7/2003 | Lengsfeld ...................... 435/7.9 |
| 2005/0064505 | A1 | | 3/2005 | Soto-Jara et al. |
| 2005/0266412 | A1 | | 12/2005 | Prusiner |
| 2006/0040260 | A1 | | 2/2006 | Baskakov |
| 2006/0154239 | A1 | * | 7/2006 | Gassner ............................ 435/5 |
| 2006/0263767 | A1 | | 11/2006 | Castrillon et al. |
| 2007/0020682 | A1 | | 1/2007 | Soto-Jara et al. |
| 2008/0118938 | A1 | | 5/2008 | Estrada et al. |

FOREIGN PATENT DOCUMENTS

| | | | |
|---|---|---|---|
| WO | WO 00/48003 | * | 8/2000 |
| WO | WO 02/04954 | A2 | 1/2002 |
| WO | WO 2004/110243 | A2 | 12/2004 |
| WO | WO 2004/113925 | A1 * | 12/2004 |
| WO | WO 2006/113915 | A2 | 10/2006 |
| WO | WO 2007/067627 | A2 | 6/2007 |
| WO | WO 2007/082173 | A2 | 7/2007 |

OTHER PUBLICATIONS

Aguzzi, "Prion biology: the quest for the test," *Nature Methods* 4(8):614-616, Aug. 2007.

Atarashi et al., "Ultrasensitive detection of scrapie prion protein using seeded conversion of recombinant prion protein," *Nature Methods* 4(8):645-650, Aug. 2007.
Atarashi et al., "Simplified ultrasensitive prion detection by recombinant PrP conversion with shaking," *Nature Methods* 5(3):211-212, Mar. 2008.
Atkinson, "Bovine spongiform encephalopathy (BSE): its context in New Zealand and new tests," *New Zealand Journal of Agricultural Research* 48:499-515, 2005.
Baskakov et al., "Pathway Complexity of Prion Protein Assembly into Amyloid," *The Journal of Biological Chemistry* 277(24):21140-21148, Jun. 14, 2002.
Bieschke et al., "Autocatalytic self-propagation of misfolded prion protein," *PNAS* 101(33):12207-12211, Aug. 17, 2004.
Blochberger et al., "Prion protein expression in Chinese hamster ovary cells using a glutamine synthetase selection and amplification system," *Protein Engineering* 10(12):1465-1473, 1997.
Bocharova et al., "Synthetic prions generated in vitro are similar to a newly identified subpopulation of PrP$^{Sc}$ from sporadic Creutzfeldt-Jakob Disease," *Protein Science* 14:1222-1232, 2005.
Castilla et al., "In vitro generation of infectious scrapie prions," *Cell* 121(2):195-206, Apr. 22, 2005.
Castilla et al., "Detection of prions in blood," *Nature Medicine* 11(9):982-985, Sep. 2005.
Castilla et al., "Protein Misfolding Cyclic Amplification for Diagnosis and Prion Propagation Studies," *Methods in Enzymology* 412:3-21, 2006.
Colby et al., "Prion detection by an amyloid seeding assay," *PNAS* 104(52):20914-20919, Dec. 26, 2007.

(Continued)

*Primary Examiner* — Mark Shibuya
*Assistant Examiner* — Christine Foster
(74) *Attorney, Agent, or Firm* — Klarquist Sparkman, LLP

(57) ABSTRACT

The present disclosure relates to methods and compositions for the detection of infectious proteins or prions in samples, including the diagnosis of prion related diseases. One embodiment is an ultrasensitive method for detecting PrP-res (PrP$^{Sc}$) that allows the use of recombinant PrP-sen (rPrP-sen) as a substrate for seeded polymerization. A sample is mixed with purified rPrP-sen to make a reaction mix which is incubated to permit aggregation of the rPrP-sen with the PrP-res that may be present in the sample. Any aggregates are intermittently disaggregated by agitation (for example by sonication) and the reaction allowed to proceed to amplify target substrate. Any rPrP-res$^{(Sc)}$ in the reaction mix is detected to indicate the presence of PrP-res in the original sample. This assay, which is called rPrP-PMCA, is surprisingly much faster than existing PMCA methods, yet it still retains sufficient sensitivity to detect extremely low levels of PrP-res. An alternative of rPrP-PMCA is the QUIC method in which shaking of the reaction mixture is substituted for sonication. The surprising speed and efficiency of the method permits the rapid identification and diagnosis of prion disease, which can limit the transmission of prion diseases, particularly through the food supply.

12 Claims, 21 Drawing Sheets

OTHER PUBLICATIONS

Deleault et al., "Protease-resistant Prion Protein Amplification Reconstituted with Partially Purified Substrates and Synthetic Polyanions," *The Journal of Biological Chemistry* 280(29):26873-26879, Jul. 22, 2005.

Deleault et al., "Formation of native prions from minimal components in vitro," *PNAS* 104(23):9741-9746, Jun. 5, 2007.

Geoghegan et al., "Selective Incorporation of Polyanionic Molecules into Hamster Prions," *The Journal of Biological Chemistry* 282(50):36341-36353, Dec. 14, 2007.

Grassi et al., "Progress and limits of TSE diagnostic tools," *Vet. Res.* 39(4):33, Jul.-Aug. 2008.

Kim et al., "Effect of transition metals (Mn, Cu, Fe) and deoxycholic acid (DA) on the conversion of $PrP^C$ to $PrP^{res}$," *The FASEB Journal* 19(77):783, May 2005.

Kurt et al., "Efficient in Vitro Amplification of Chronic Wasting Disease $PrP^{RES}$," *Journal of Virology* 81(17):9605-9608, Sep. 2007.

Lee and Caughey, "A simplified recipe for prions," *PNAS* 104(23):9551-9552, Jun. 5, 2007.

Legname et al., "Synthetic mammalian prions," *Science* 305(5684):673-676, Jul. 30, 2004.

Li et al., "Species barriers for chronic wasting disease by in vitro conversion of prion protein," *Biochemical and Biophysical Research Communications* 364:796-800, 2007.

Murayama et al., "Efficient in vitro amplification of a mouse-adapted scrapie prion protein," *Neurosci Lett.* 413(3):270-273, Feb. 21, 2007.

Saá et al., "Cyclic amplification of protein misfolding and aggregation," *Methods Mol Biol.* 299:53-65, 2005.

Saá et al., "Ultra-efficient Replication of Infectious Prions by Automated Protein Misfolding Cyclic Amplification," *The Journal of Biological Chemistry* 281(46):35245-35252, Nov. 17, 2006.

Saborio et al., "Sensitive detection of pathological prion protein by cyclic amplification of protein misfolding," *Nature* 411:810-813, Jun. 14, 2001.

Sarafoff et al., "Automated PrPres amplification using indirect sonication," *J. Biochem Biophys Methods* 63(3):213-221, Jun. 30, 2005.

Seidel et al., "Scrapie Agent (Strain 263K) Can Transmit Disease via the Oral Route after Persistence in Soil over Years," *PLoS ONE* 2(5):e435, May 9, 2007.

Stöhr et al., "Mechanisms of prion protein assembly into amyloid," *PNAS* 105(7):2409-2414, Feb. 19, 2008.

Supattapone, "Prion protein conversion in vitro," *J. Mol Med.* 82(6):348-356, Jun. 2004.

Trieschmann et al., "Ultra-sensitive detection of prion protein fibrils by flow cytometry in blood from cattle affected with bovine spongiform encephalopathy," *BMC Biotechnology* 5(26), Oct. 4, 2005.

Weber et al., "Cell-free formation of misfolded prion protein with authentic prion infectivity," *PNAS* 103(43)15818-15823, Oct. 24, 2006.

Wrammert et al., "Rapid cloning of high-affinity human monoclonal antibodies against influenza virus," *Nature* 453(7195):667-671, May 29, 2008.

Xiong et al., "Conformational change, aggregation and fibril formation induced by detergent treatments of cellular prion protein," *Journal of Neurochemistry* 79:669-678, 2001.

Zou et al., "Acidic pH and Detergents Enhance in Vitro Conversion of Human Brain $PrP^C$ to a $PrP^{Sc}$-like Form," *The Journal of Biological Chemistry* 277(46):43942-43947, Nov. 15, 2002.

International Search Report dated Nov. 17, 2008 from International Application No. PCT/US2008/070656.

* cited by examiner

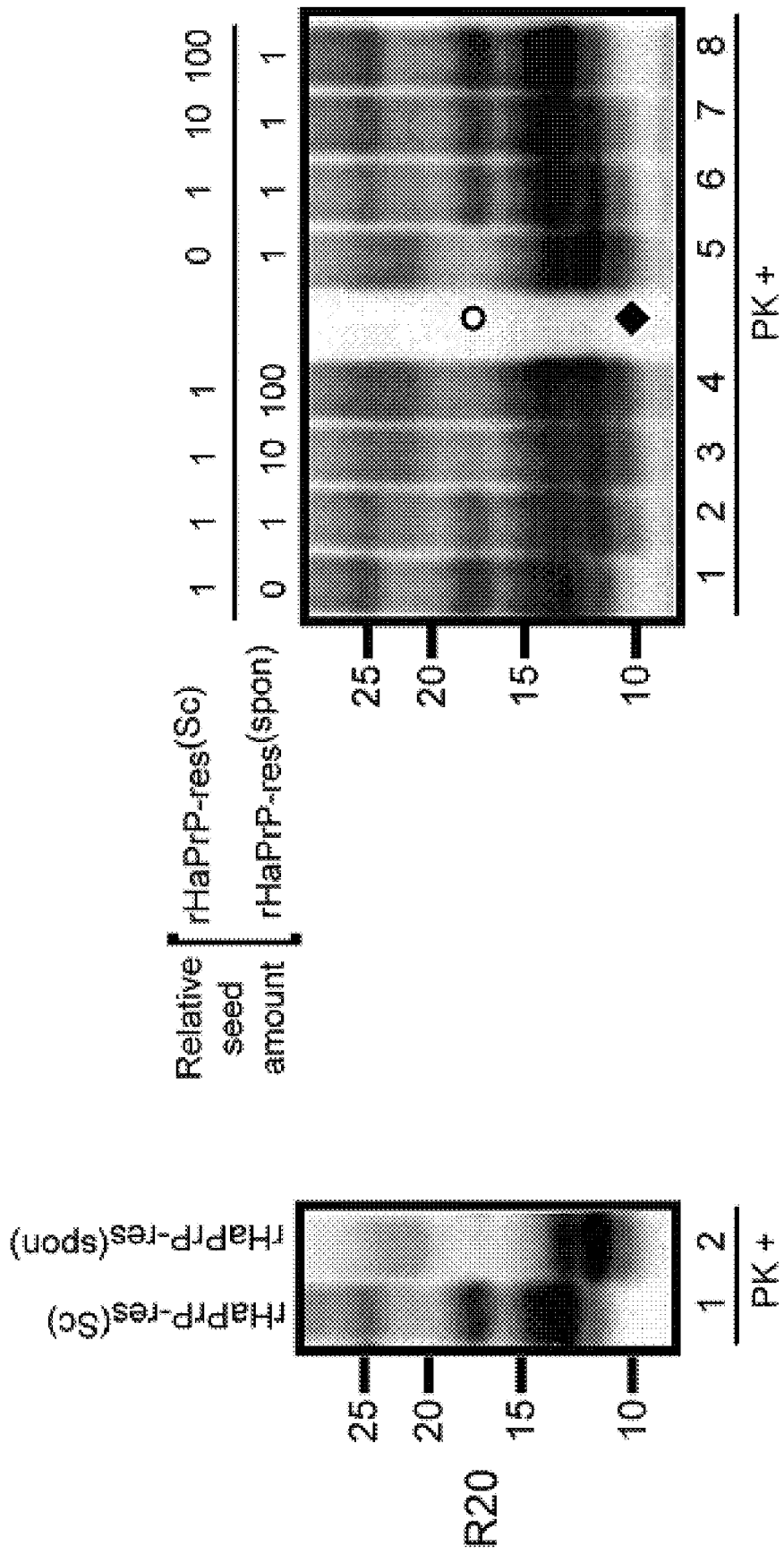

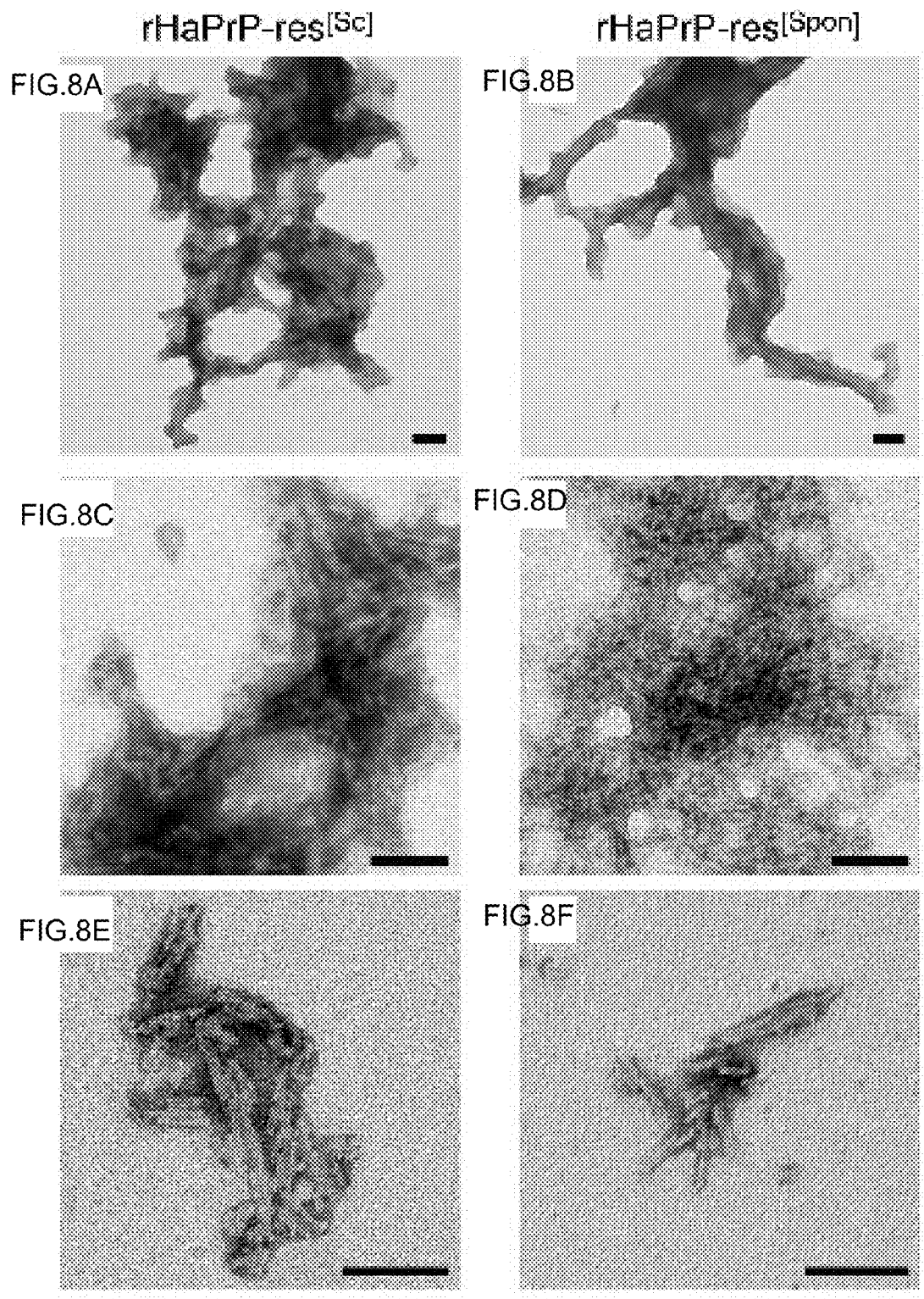

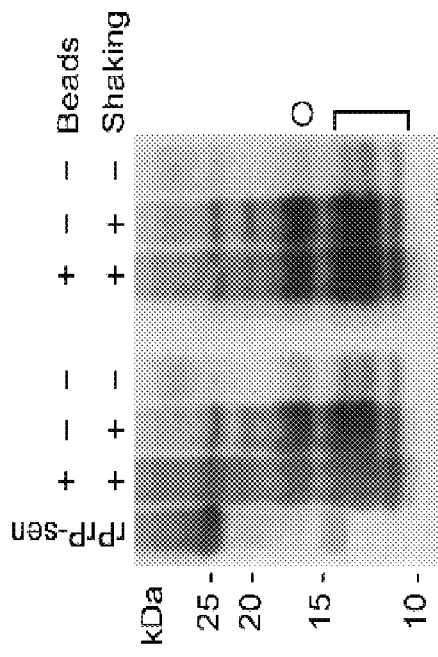
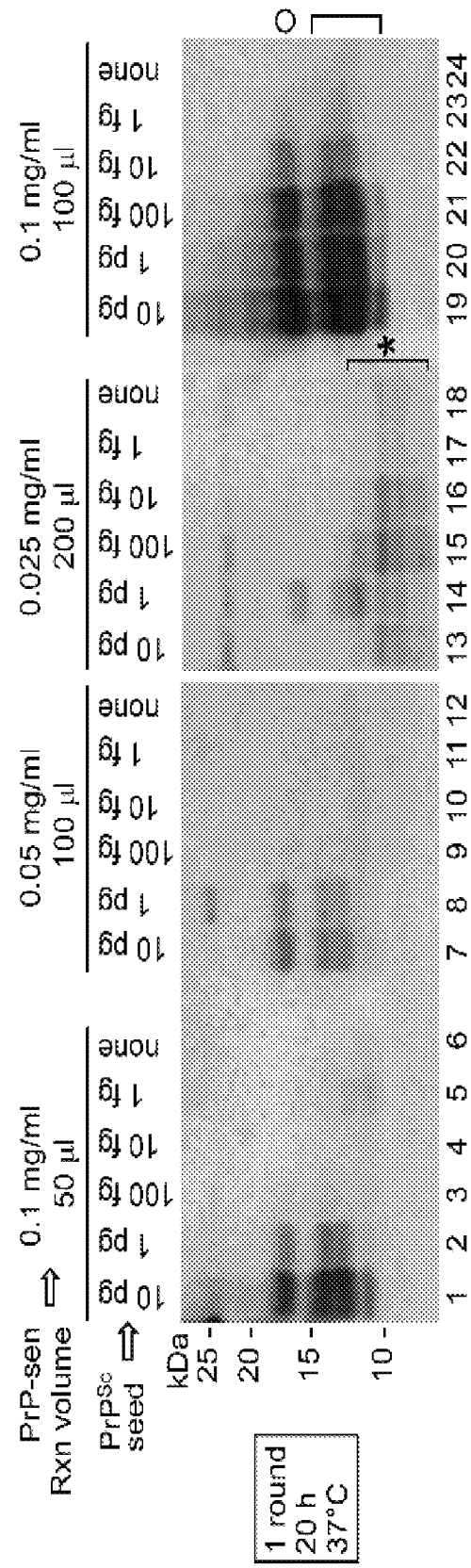
FIG. 10A
FIG. 10B

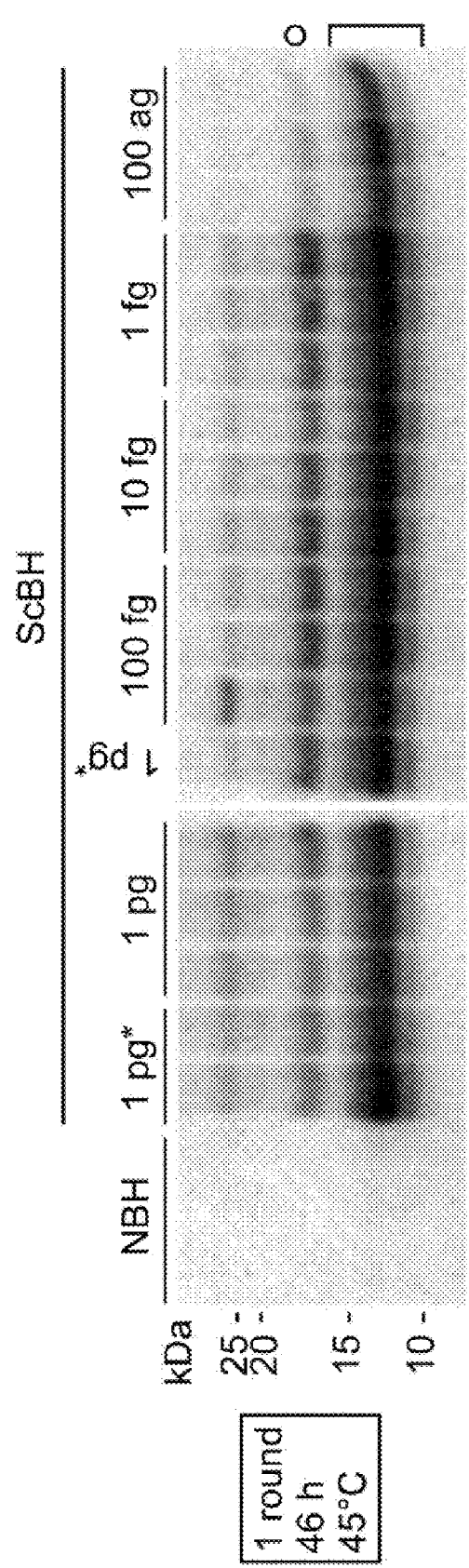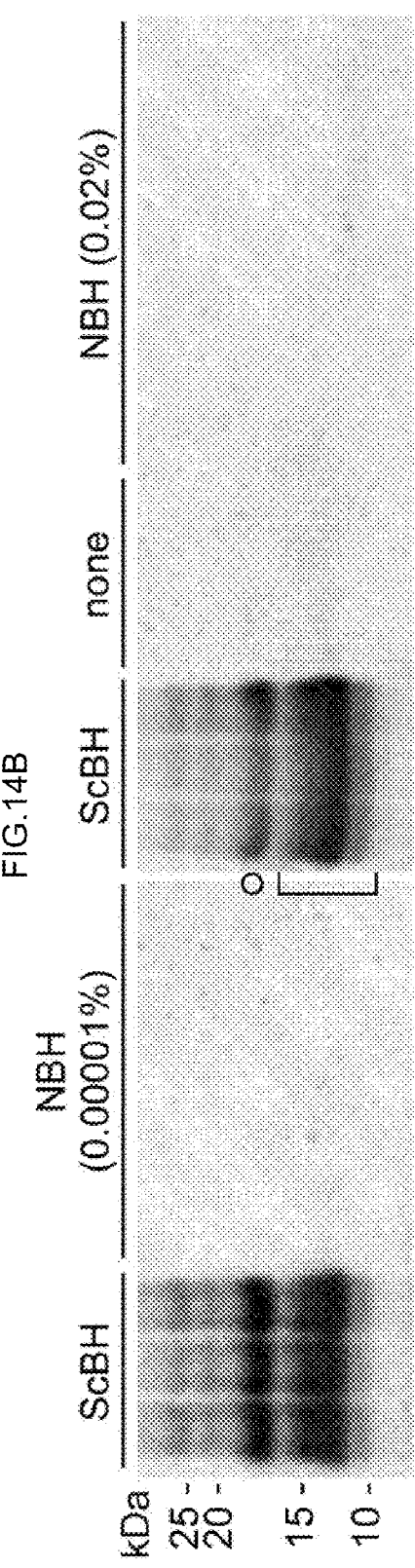
FIG. 14A
FIG. 14B

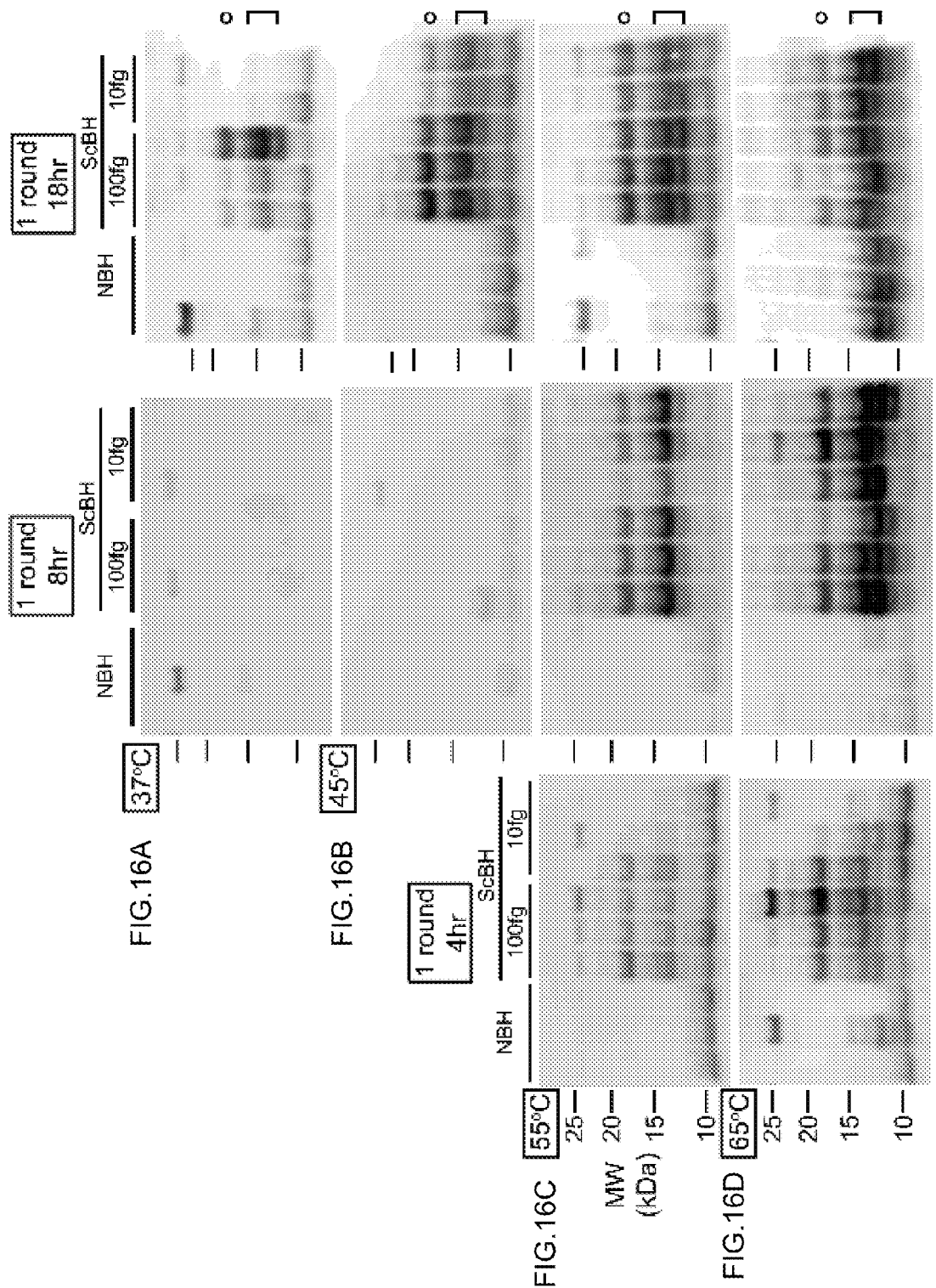

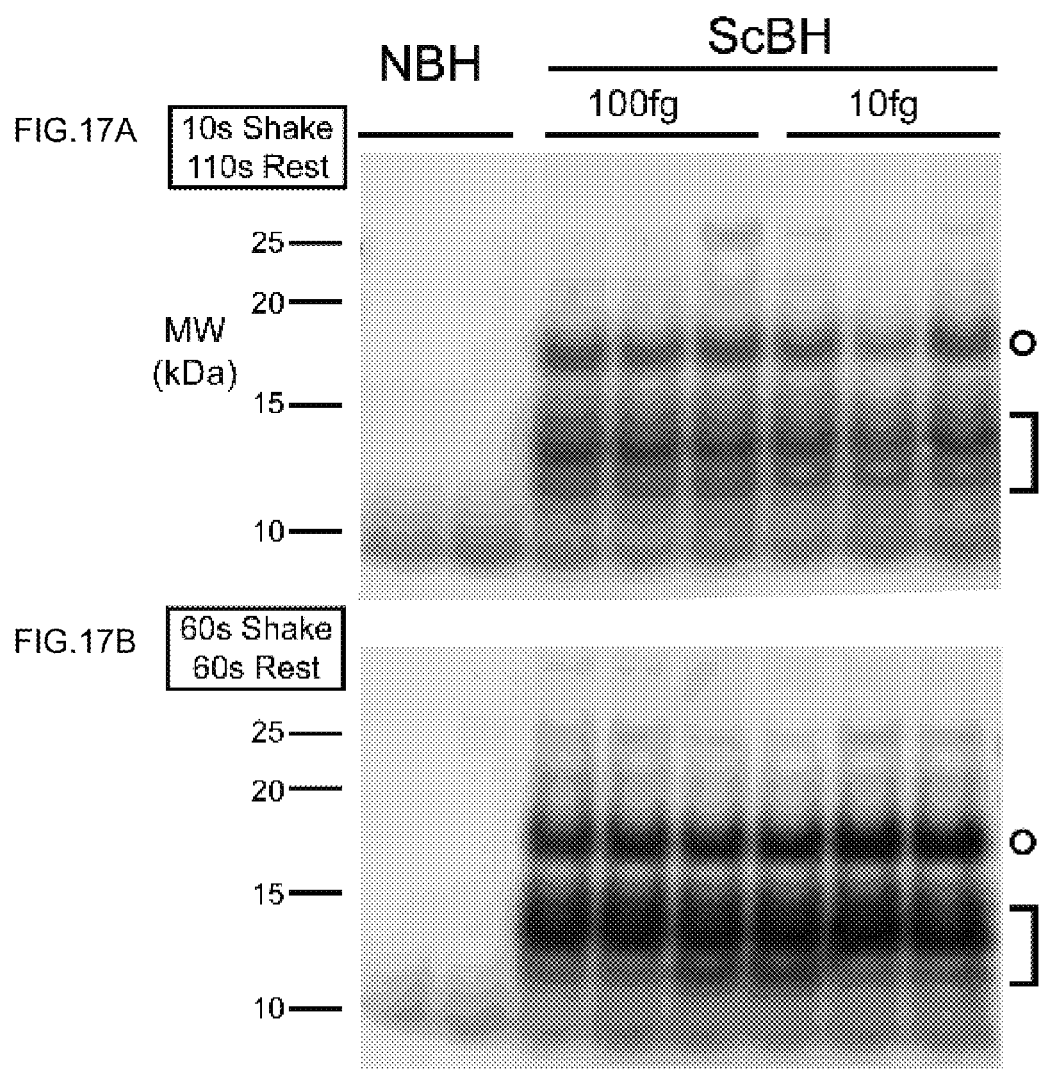

SEQUENCE LISTING

<160> NUMBER OF SEQ ID NOS: 11

<210> SEQ ID NO 1
<211> LENGTH: 209
<212> TYPE: PRT
<213> ORGANISM: Mesocricetus auratus

<400> SEQUENCE: 1

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
                20                  25                  30

Gly Thr Trp Gly Gln Pro His Gly Gly Trp Gly Gln Pro His Gly
            35                  40                  45

Gly Gly Trp Gly Gln Pro His Gly Gly Trp Gly Gln Pro His Gly
        50                  55                  60

Gly Gly Trp Gly Gln Gly Gly Thr His Asn Gln Trp Asn Lys Pro
65                  70                  75                  80

Asn Lys Pro Lys Thr Ser Met Lys His Met Ala Gly Ala Ala Ala
                85                  90                  95

Gly Ala Val Val Gly Gly Leu Gly Gly Tyr Met Leu Gly Ser Ala Met
                100                 105                 110

Ser Arg Pro Met Leu His Phe Gly Asn Asp Trp Glu Asp Arg Tyr Tyr
                115                 120                 125

Arg Glu Asn Met Asn Arg Tyr Pro Asn Gln Val Tyr Tyr Arg Pro Val
            130                 135                 140

Asp Gln Tyr Asn Asn Gln Asn Asn Phe Val His Asp Cys Val Asn Ile
145                 150                 155                 160

Thr Ile Lys Gln His Thr Val Thr Thr Thr Thr Lys Gly Glu Asn Phe
                165                 170                 175

Thr Glu Thr Asp Val Lys Met Met Glu Arg Val Val Glu Gln Met Cys
                180                 185                 190

Val Thr Gln Tyr Gln Lys Glu Ser Gln Ala Tyr Tyr Asp Gly Arg Arg
            195                 200                 205

Ser

<210> SEQ ID NO 2
<211> LENGTH: 208
<212> TYPE: PRT
<213> ORGANISM: Mus musculus

<400> SEQUENCE: 2

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
                20                  25                  30

Thr Trp Gly Gln Pro His Gly Gly Trp Gly Gln Pro His Gly Gly
            35                  40                  45

Ser Trp Gly Gln Pro His Gly Gly Ser Trp Gly Gln Pro His Gly Gly
        50                  55                  60

Gly Trp Gly Gln Gly Gly Gly Thr His Asn Gln Trp Asn Lys Pro Ser
65                  70                  75                  80

Lys Pro Lys Thr Asn Leu Lys His Val Ala Gly Ala Ala Ala Ala Gly
                85                  90                  95

Ala Val Val Gly Gly Leu Gly Gly Tyr Met Leu Gly Ser Ala Met Ser

```
            100                 105                 110
Arg Pro Met Ile His Phe Gly Asn Asp Trp Glu Asp Arg Tyr Tyr Arg
        115                 120                 125

Glu Asn Met Tyr Arg Tyr Pro Asn Gln Val Tyr Tyr Arg Pro Val Asp
130                 135                 140

Gln Tyr Ser Asn Gln Asn Asn Phe Val His Asp Cys Val Asn Ile Thr
145                 150                 155                 160

Ile Lys Gln His Thr Val Thr Thr Thr Lys Gly Glu Asn Phe Thr
        165                 170                 175

Glu Thr Asp Val Lys Met Met Glu Arg Val Val Glu Gln Met Cys Val
            180                 185                 190

Thr Gln Tyr Gln Lys Glu Ser Gln Ala Tyr Tyr Asp Gly Arg Arg Ser
        195                 200                 205

<210> SEQ ID NO 3
<211> LENGTH: 209
<212> TYPE: PRT
<213> ORGANISM: Homo sapiens

<400> SEQUENCE: 3

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
            20                  25                  30

Gly Gly Trp Gly Gln Pro His Gly Gly Gly Trp Gly Gln Pro His Gly
        35                  40                  45

Gly Gly Trp Gly Gln Pro His Gly Gly Gly Trp Gly Gln Pro His Gly
    50                  55                  60

Gly Gly Trp Gly Gln Gly Gly Gly Thr His Ser Gln Trp Asn Lys Pro
65                  70                  75                  80

Ser Lys Pro Lys Thr Asn Met Lys His Met Ala Gly Ala Ala Ala Ala
                85                  90                  95

Gly Ala Val Val Gly Gly Leu Gly Gly Tyr Met Leu Gly Ser Ala Met
            100                 105                 110

Ser Arg Pro Ile Ile His Phe Gly Ser Asp Tyr Glu Asp Arg Tyr Tyr
        115                 120                 125

Arg Glu Asn Met His Arg Tyr Pro Asn Gln Val Tyr Tyr Arg Pro Met
    130                 135                 140

Asp Glu Tyr Ser Asn Gln Asn Asn Phe Val His Asp Cys Val Asn Ile
145                 150                 155                 160

Thr Ile Lys Gln His Thr Val Thr Thr Thr Thr Lys Gly Glu Asn Phe
                165                 170                 175

Thr Glu Thr Asp Val Lys Met Met Glu Arg Val Val Glu Gln Met Cys
            180                 185                 190

Ile Thr Gln Tyr Glu Arg Glu Ser Gln Ala Tyr Tyr Gln Arg Gly Ser
        195                 200                 205

Ser

<210> SEQ ID NO 4
<211> LENGTH: 209
<212> TYPE: PRT
<213> ORGANISM: Homo sapiens

<400> SEQUENCE: 4

Lys Lys Arg Pro Lys Pro Gly Gly Trp Asn Thr Gly Gly Ser Arg Tyr
1               5                   10                  15
```

```
Pro Gly Gln Gly Ser Pro Gly Gly Asn Arg Tyr Pro Pro Gln Gly
            20                  25                  30

Gly Gly Trp Gly Gln Pro His Gly Gly Trp Gly Gln Pro His Gly
        35                  40                  45

Gly Gly Trp Gly Gln Pro His Gly Gly Trp Gly Gln Pro His Gly
50                  55                  60

Gly Gly Trp Gly Gln Gly Gly Thr His Ser Gln Trp Asn Lys Pro
65                  70                  75                  80

Ser Lys Pro Lys Thr Asn Met Lys His Met Ala Gly Ala Ala Ala
                85                  90                  95

Gly Ala Val Val Gly Gly Leu Gly Gly Tyr Val Leu Gly Ser Ala Met
            100                 105                 110

Ser Arg Pro Ile Ile His Phe Gly Ser Asp Tyr Glu Asp Arg Tyr Tyr
            115                 120                 125

Arg Glu Asn Met His Arg Tyr Pro Asn Gln Val Tyr Tyr Arg Pro Met
        130                 135                 140

Asp Glu Tyr Ser Asn Gln Asn Asn Phe Val His Asp Cys Val Asn Ile
145                 150                 155                 160

Thr Ile Lys Gln His Thr Val Thr Thr Thr Thr Lys Gly Glu Asn Phe
                165                 170                 175

Thr Glu Thr Asp Val Lys Met Met Glu Arg Val Val Glu Gln Met Cys
            180                 185                 190

Ile Thr Gln Tyr Glu Arg Glu Ser Gln Ala Tyr Tyr Gln Arg Gly Ser
        195                 200                 205

Ser

<210> SEQ ID NO 5
<211> LENGTH: 218
<212> TYPE: PRT
<213> ORGANISM: Bos taurus

<400> SEQUENCE: 5

Lys Lys Arg Pro Lys Pro Gly Gly Trp Asn Thr Gly Gly Ser Arg
1               5                   10                  15

Tyr Pro Gly Gln Gly Ser Pro Gly Gly Asn Arg Tyr Pro Pro Gln Gly
            20                  25                  30

Gly Gly Gly Trp Gly Gln Pro His Gly Gly Gly Trp Gly Gln Pro His
        35                  40                  45

Gly Gly Gly Trp Gly Gln Pro His Gly Gly Gly Trp Gly Gln Pro His
50                  55                  60

Gly Gly Gly Trp Gly Gln Pro His Gly Gly Gly Trp Gly Gln Gly
65                  70                  75                  80

Gly Thr His Gly Gln Trp Asn Lys Pro Ser Lys Pro Lys Thr Asn Met
                85                  90                  95

Lys His Val Ala Gly Ala Ala Ala Ala Gly Ala Val Val Gly Gly Leu
            100                 105                 110

Gly Gly Tyr Met Leu Gly Ser Ala Met Ser Arg Pro Leu Ile His Phe
        115                 120                 125

Gly Ser Asp Tyr Glu Asp Arg Tyr Tyr Arg Glu Asn Met His Arg Tyr
130                 135                 140

Pro Asn Gln Val Tyr Tyr Arg Pro Val Asp Gln Tyr Ser Asn Gln Asn
145                 150                 155                 160

Asn Phe Val His Asp Cys Val Asn Ile Thr Val Lys Glu His Thr Val
                165                 170                 175

Thr Thr Thr Thr Lys Gly Glu Asn Phe Thr Glu Thr Asp Ile Lys Met
```

```
                     180                 185                 190
Met Glu Arg Val Val Glu Gln Met Cys Ile Thr Gln Tyr Gln Arg Glu
            195                 200                 205

Ser Gln Ala Tyr Tyr Gln Arg Gly Ala Ser
            210                 215

<210> SEQ ID NO 6
<211> LENGTH: 209
<212> TYPE: PRT
<213> ORGANISM: Ovis aries

<400> SEQUENCE: 6

Lys Lys Arg Pro Lys Pro Gly Gly Gly Trp Asn Thr Gly Gly Ser Arg
1               5                   10                  15

Tyr Pro Gly Gln Gly Ser Pro Gly Gly Asn Arg Tyr Pro Pro Gln Gly
            20                  25                  30

Gly Gly Gly Trp Gly Gln Pro His Gly Gly Gly Trp Gly Gln Pro His
        35                  40                  45

Gly Gly Gly Trp Gly Gln Pro His Gly Gly Gly Trp Gly Gln Pro His
    50                  55                  60

Gly Gly Gly Gly Trp Gly Gln Gly Gly Ser His Ser Gln Trp Asn Lys
65                  70                  75                  80

Pro Ser Lys Pro Lys Thr Asn Met Lys His Val Ala Gly Ala Ala Ala
                85                  90                  95

Ala Gly Ala Val Val Gly Gly Leu Gly Gly Tyr Met Leu Gly Ser Ala
            100                 105                 110

Met Ser Arg Pro Leu Ile His Phe Gly Asn Asp Tyr Glu Asp Arg Tyr
        115                 120                 125

Tyr Arg Glu Asn Met Tyr Arg Tyr Pro Asn Gln Val Tyr Tyr Arg Pro
    130                 135                 140

Val Asp Gln Tyr Ser Asn Gln Asn Asn Phe Val His Asp Cys Val Asn
145                 150                 155                 160

Ile Thr Val Lys Gln His Thr Val Thr Thr Thr Lys Gly Glu Asn
                165                 170                 175

Phe Thr Glu Thr Asp Ile Lys Ile Met Glu Arg Val Val Glu Gln Met
            180                 185                 190

Cys Ile Thr Gln Tyr Gln Arg Glu Ser Gln Ala Tyr Tyr Gln Arg Gly
        195                 200                 205

Ala

<210> SEQ ID NO 7
<211> LENGTH: 210
<212> TYPE: PRT
<213> ORGANISM: Cervus unicolor

<400> SEQUENCE: 7

Lys Lys Arg Pro Lys Pro Gly Gly Gly Trp Asn Thr Gly Gly Ser Arg
1               5                   10                  15

Tyr Pro Gly Gln Gly Ser Pro Gly Gly Asn Arg Tyr Pro Pro Gln Gly
            20                  25                  30

Gly Gly Gly Trp Gly Gln Pro His Gly Gly Gly Trp Gly Gln Pro His
        35                  40                  45

Gly Gly Gly Trp Gly Gln Pro His Gly Gly Gly Trp Gly Gln Pro His
    50                  55                  60

Gly Gly Gly Gly Trp Gly Gln Gly Gly Thr His Ser Gln Trp Asn Lys
65                  70                  75                  80
```

```
Pro Ser Lys Pro Lys Thr Asn Met Lys His Val Ala Gly Ala Ala Ala
            85                  90                  95

Ala Gly Ala Val Val Gly Gly Leu Gly Gly Tyr Met Leu Gly Ser Ala
            100                 105                 110

Met Ser Arg Pro Leu Ile His Phe Gly Asn Asp Tyr Glu Asp Arg Tyr
            115                 120                 125

Tyr Arg Glu Asn Met Tyr Arg Tyr Pro Asn Gln Val Tyr Tyr Arg Pro
        130                 135                 140

Val Asp Gln Tyr Asn Asn Gln Asn Thr Phe Val His Asp Cys Val Asn
145                 150                 155                 160

Ile Thr Val Lys Gln His Thr Val Thr Thr Thr Lys Gly Glu Asn
            165                 170                 175

Phe Thr Glu Thr Asp Ile Lys Met Met Glu Arg Val Val Glu Gln Met
            180                 185                 190

Cys Ile Thr Gln Tyr Gln Arg Glu Ser Gln Ala Tyr Tyr Gln Arg Gly
            195                 200                 205

Ala Ser
    210

<210> SEQ ID NO 8
<211> LENGTH: 240
<212> TYPE: PRT
<213> ORGANISM: Mesocricetus auratus

<400> SEQUENCE: 8

Met Trp Thr Asp Val Gly Leu Cys Lys Lys Arg Pro Lys Pro Gly Gly
1               5                   10                  15

Trp Asn Thr Gly Gly Ser Arg Tyr Pro Gly Gln Gly Ser Pro Gly Gly
            20                  25                  30

Asn Arg Tyr Pro Pro Gln Gly Gly Thr Trp Gly Gln Pro His Gly
            35                  40                  45

Gly Gly Trp Gly Gln Pro His Gly Gly Gly Trp Gly Gln Pro His Gly
        50                  55                  60

Gly Gly Trp Gly Gln Pro His Gly Gly Gly Trp Gly Gln Gly Gly Gly
65                  70                  75                  80

Thr His Asn Gln Trp Asn Lys Pro Ser Lys Pro Lys Thr Asn Met Lys
            85                  90                  95

His Met Ala Gly Ala Ala Ala Ala Gly Ala Val Val Gly Gly Leu Gly
            100                 105                 110

Gly Tyr Met Leu Gly Ser Ala Met Ser Arg Pro Met Met His Phe Gly
            115                 120                 125

Asn Asp Trp Glu Asp Arg Tyr Tyr Arg Glu Asn Met Asn Arg Tyr Pro
        130                 135                 140

Asn Gln Val Tyr Tyr Arg Pro Val Asp Gln Tyr Asn Asn Gln Asn Asn
145                 150                 155                 160

Phe Val His Asp Cys Val Asn Ile Thr Ile Lys Gln His Thr Val Thr
            165                 170                 175

Thr Thr Thr Lys Gly Glu Asn Phe Thr Glu Thr Asp Ile Lys Ile Met
            180                 185                 190

Glu Arg Val Val Glu Gln Met Cys Thr Thr Gln Tyr Gln Lys Glu Ser
            195                 200                 205

Gln Ala Tyr Tyr Asp Gly Arg Arg Ser Ser Ala Val Leu Phe Ser Ser
        210                 215                 220

Pro Pro Val Ile Leu Leu Ile Ser Phe Leu Ile Phe Leu Met Val Gly
225                 230                 235                 240
```

```
<210> SEQ ID NO 9
<211> LENGTH: 254
<212> TYPE: PRT
<213> ORGANISM: Mus musculus

<400> SEQUENCE: 9

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Trp Gly Gln Gly Gly Gly Thr His Asn
                85                  90                  95

Gln Trp Asn Lys Pro Ser Lys Pro Lys Thr Asn Leu Lys His Val Ala
                100                 105                 110

Gly Ala Ala Ala Ala Gly Ala Val Val Gly Gly Leu Gly Gly Tyr Met
            115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 10
<211> LENGTH: 253
<212> TYPE: PRT
<213> ORGANISM: Homo sapiens

<400> SEQUENCE: 10

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
```

```
                            85                  90                  95
Ser Gln Trp Asn Lys Pro Ser Lys Pro Lys Thr Asn Met Lys His Met
                100                 105                 110
Ala Gly Ala Ala Ala Gly Ala Val Val Gly Gly Leu Gly Gly Tyr
            115                 120                 125
Met Leu Gly Ser Ala Met Ser Arg Pro Ile Ile His Phe Gly Ser Asp
        130                 135                 140
Tyr Glu Asp Arg Tyr Tyr Arg Glu Asn Met His Arg Tyr Pro Asn Gln
145                 150                 155                 160
Val Tyr Tyr Arg Pro Met Asp Glu Tyr Ser Asn Gln Asn Asn Phe Val
                165                 170                 175
His Asp Cys Val Asn Ile Thr Ile Lys Gln His Thr Val Thr Thr Thr
                180                 185                 190
Thr Lys Gly Glu Asn Phe Thr Glu Thr Asp Val Lys Met Met Glu Arg
            195                 200                 205
Val Val Glu Gln Met Cys Ile Thr Gln Tyr Glu Arg Glu Ser Gln Ala
        210                 215                 220
Tyr Tyr Gln Arg Gly Ser Ser Met Val Leu Phe Ser Ser Pro Pro Val
225                 230                 235                 240
Ile Leu Leu Ile Ser Phe Leu Ile Phe Leu Ile Val Gly
                245                 250

<210> SEQ ID NO 11
<211> LENGTH: 253
<212> TYPE: PRT
<213> ORGANISM: Homo sapiens

<400> SEQUENCE: 11

Met Ala Asn Leu Gly Cys Trp Met Leu Val Leu Phe Val Ala Thr Trp
1               5                   10                  15
Ser Asp Leu Gly Leu Cys Lys Lys Arg Pro Lys Pro Gly Gly Trp Asn
                20                  25                  30
Thr Gly Gly Ser Arg Tyr Pro Gly Gln Gly Ser Pro Gly Gly Asn Arg
            35                  40                  45
Tyr Pro Pro Gln Gly Gly Gly Gly Trp Gly Gln Pro His Gly Gly Gly
        50                  55                  60
Trp Gly Gln Pro His Gly Gly Gly Trp Gly Gln Pro His Gly Gly Gly
65                  70                  75                  80
Trp Gly Gln Pro His Gly Gly Gly Trp Gly Gln Gly Gly Gly Thr His
                85                  90                  95
Ser Gln Trp Asn Lys Pro Ser Lys Pro Lys Thr Asn Met Lys His Met
                100                 105                 110
Ala Gly Ala Ala Ala Gly Ala Val Val Gly Gly Leu Gly Gly Tyr
            115                 120                 125
Val Leu Gly Ser Ala Met Ser Arg Pro Ile Ile His Phe Gly Ser Asp
        130                 135                 140
Tyr Glu Asp Arg Tyr Tyr Arg Glu Asn Met His Arg Tyr Pro Asn Gln
145                 150                 155                 160
Val Tyr Tyr Arg Pro Met Asp Glu Tyr Ser Asn Gln Asn Asn Phe Val
                165                 170                 175
His Asp Cys Val Asn Ile Thr Ile Lys Gln His Thr Val Thr Thr Thr
                180                 185                 190
Thr Lys Gly Glu Asn Phe Thr Glu Thr Asp Val Lys Met Met Glu Arg
            195                 200                 205
Val Val Glu Gln Met Cys Ile Thr Gln Tyr Glu Arg Glu Ser Gln Ala
```

```
                210                 215                 220
Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250
```

DETECTION OF INFECTIOUS PRION PROTEIN BY SEEDED CONVERSION OF RECOMBINANT PRION PROTEIN

PRIORITY

Benefit is claimed of U.S. Provisional Application 60/961,364, filed Jul. 20, 2007 and U.S. Provisional Application 61/021,865, filed Jan. 17, 2008. The disclosures of both of those provisional patent applications are incorporated by reference in their entirety.

FIELD OF THE DISCLOSURE

The present disclosure relates to methods and compositions for the detection of infectious proteins or prions in samples, including the diagnosis of prion related diseases.

BACKGROUND

Prion diseases, which are also called transmissible spongiform encephalopathies (TSEs), include a group of fatal infectious neurodegenerative diseases that include Creutzfeldt-Jakob disease (CJD), kuru, Gerstmann-Straussler Scheinker syndrome (GSS), fatal familial insomnia (FFI) and sporadic fatal insomnia (sFI) in humans, and scrapie, bovine spongiform encephalopathy (BSE) and chronic wasting disease (CWD) in animals. These diseases are characterized by brain vacuolation, astrogliosis, neuronal apoptosis, and the accumulation of misfolded prion protein (PrP-res, also known as $PrP^{Sc}$ and $PrP^{CJD}$) in the central nervous system. TSEs have incubation periods of months to years, but after the appearance of clinical signs they are rapidly progressive, untreatable, and invariably fatal. Attempts at TSE risk reduction have led to profound changes in the production and trade of agricultural goods, medicines, cosmetics, and biotechnology products.

The hallmark event of prion disease is the formation of an abnormally folded protein called $PrP^{Sc}$ (or PrP-res), which is a post-translationally modified version of a normal protein, termed $PrP^C$ (also known as PrP-sen). A prion detection method termed protein misfolding cyclic amplification (PMCA) is based on the ability of prions to replicate in vitro in cell lysates containing $PrP^C$ (see, for instance, WO0204954). However, the limitations of PMCA include the time required to achieve optimal sensitivity (~3 weeks) and the requirement for brain-derived PrP-sen as the amplification substrate.

Castilla et al., *Methods in Enzymology* 412:3-21 (2006) has stated that it has not been possible to use PMCA with highly purified prion proteins such as $PrP^C$. Although the reason for this limitation was unknown, it was believed that factors in brain homogenates were needed to catalyze prion propagation. Recombinant PrP-sen expressed from *E. coli* also lacks glycosylation and the glycophosphatidylinositol (GPI) anchor, which was additionally believed to contribute to the difficulty of using rPrP-sen in amplification reactions. Such rPrP-sen has been converted to protease-resistant forms with very limited yields when mixed with $PrP^{Sc}$ in the past.

Another problem with PMCA is that the formation of $PrP^{Sc}$ reaches a plateau as the number of amplification cycles increases. Castrillon et al. (US Patent Publication No. 2006/0263767) attempted to overcome this problem by serial amplification of prion protein by removing a portion of the reaction mix and incubating it with additional non-pathogenic protein. Although serial amplification PMCA (saPMCA) increases prion amplification and enhances the sensitivity of the assay, the necessity of performing multiple rounds of serial amplification has decreased the overall practicality of the process.

Supattapone and Deleault (PCT Publication No. WO 2007/082173) also note that efficiency of amplification may require a cellular factor other than PrP-sen. They disclose in vitro amplification of immunoaffinity or exchange chromatography purified PrP-sen in the presence of RNA, synthetic polyanions and partially purified substrates to increase the sensitivity of diagnostic methods for detecting PrP-res.

However, there continues to be a need for a more rapid method for the detection of PrP-res that is sensitive enough to detect low level prion contamination. The widespread public health concern about TSE diseases could be allayed by the development of such a test.

SUMMARY OF THE DISCLOSURE

Disclosed herein is an ultrasensitive method for detecting prion protein (for instance, PrP-res or $PrP^{Sc}$) that allows the use of recombinant PrP-sen (rPrP-sen) as a substrate for seeded polymerization. These methods include the use of an rPrP-res amplification assay, which includes methods such as rPrP-PMCA or QUIC, which differ in the method used to agitate the reaction. The rPrP-res amplification assays are surprisingly much faster than existing PMCA methods, yet it still retains sufficient sensitivity to detect extremely low levels of PrP-res. The surprising rapidity of the method permits the rapid identification and diagnosis of prion disease, which can limit the transmission of prion diseases, particularly through the food supply.

One embodiment of the disclosure is a method for detecting PrP-res ($PrP^{Sc}$) in a sample. The method includes the steps of (a) mixing the sample with purified rPrP-sen to make a reaction mix, and (b) performing an amplification reaction between PrP-res ($PrP^{Sc}$) and rPrP-sen in the mixture that results in the formation and amplification of one or more specific forms of recombinant PrP-res (for instance, $rPrP\text{-}res^{(Sc)}$). The amplification reaction includes the steps of (i) incubating the reaction mix to permit co-aggregation or co-polymerization of the rPrP-sen with the PrP-res that may be present in the reaction mix, and (ii) agitating any aggregates or multimers formed during step (i), for instance by shaking or sonication, and (iii) repeating steps (i) and (ii) one or more times. In step (i), aggregation of the rPrP-sen with any PrP-res that may be present in the sample results in a conversion of the rPrP-sen to $rPrP\text{-}res^{(Sc)}$. After the amplification reaction is carried out, $rPrP\text{-}res^{(Sc)}$ is detected in the reaction mix as an amplified indicator of any PrP-res originally present in the sample. This amplification procedure can be performed on an initial sample of interest, such that the method is preformed only as a single round of amplification. Optionally, a serial amplification reaction is carried out with the same steps as the first round reaction, except an aliquot of the amplified reaction mixture (instead of the original sample) is mixed with purified rPrP-sen.

In particular embodiments, the amplification reaction is carried out under conditions that inhibit production of spontaneously aggregated rPrP-res ($rPrP\text{-}res^{(spon)}$) that is independent of the presence of PrP-res in the sample, because that by-product has surprisingly been found to interfere with the desired aggregation reaction of rPrP with PrP-res and can complicate the detection of $rPrP\text{-}res^{(Sc)}$. Inhibiting the production of the by-product increases the speed, sensitivity, and reliability of the amplification reaction.

In the embodiment referred to as the QUIC assay, agitation of aggregates to disaggregate them is carried out in multiple-container trays that are physically shaken without sonication to transmit the disaggregating energy substantially equally to all the containers in the tray. The use of shaking instead of sonication has been found to provide a more easily duplicated and rapid test that retains a high degree of sensitivity.

The foregoing and other features and advantages of the disclosure will become more apparent from the following detailed description of several embodiments which proceeds with reference to the accompanying figures.

BRIEF DESCRIPTION OF THE FIGURES

FIG. 1 is a series of digital images of gels showing the comparison of hamster proteinase K resistant prion protein (HaPrP$^{Sc}$)-seeded and unseeded recombinant hamster proteinase K-sensitive prion protein (rHaPrP-sen) conversion reactions.

FIG. 2 is a pair of digital images of gels showing the detection limits of rPrP-protein misfolding cyclic amplification (rPrP-PMCA).

FIG. 3 is a pair of digital images of gels showing seeding competition between rHaPrP-res$^{(Sc)}$ and rHaPrP-res$^{(spon)}$. Purified HaPrP$^{Sc}$ and rHaPrP-res$^{(spon)}$ were each used to initiate three successive rounds of rPrP-PMCA. Aliquots of the third-round reactions containing similar amounts of either rHaPrP-res$^{(Sc)}$ and rHaPrP-res$^{(spon)}$ were used to seed fourth round reactions, which were subjected to sonication cycles over 24 hours as described in Example 2. The relative seed amounts of 1, 10 and 100 designate reactions seeded with 0.08, 0.8 or 8 µl, respectively, of the final third-round reaction volume. PK-treated reaction products of the third-round (FIG. 3A) and fourth-round (FIG. 3B) reactions were analyzed by immunoblotting with antiserum R20. The 17-kDa and 10-kDa bands specific for the rHaPrP-res$^{(Sc)}$- and rHaPrP-res$^{(spon)}$-seeded reactions, respectively, are marked with an open circle and a diamond, respectively. Positions of molecular mass markers are designated in kDa.

FIG. 5 is a pair of digital images of gels and a graph showing the generation of thioflavin-T positive, protease resistant recombinant mouse prion protein (rMoPrP) fragments by sonication.

FIG. 6 is a series of digital images of gels and graphs showing the results of seeding reactions with sonicated rPrP-res under unsonicated conditions.

FIG. 8 is a series of digital images of electron micrographs showing the ultrastructure of rHaPrP-res$^{(Sc)}$ (FIGS. 8A, 8C, 8E) and rHaPrP-res$^{(spon)}$ (FIGS. 8B, 8D, 8F). To further characterize the structure of rHaPrP-res$^{(Sc)}$ and rHaPrP-res$^{(spon)}$, the samples were examined with transmission electron microscopy. Electron micrographs of both samples prior to PK digestion revealed thick overlapping fibre bundles, the definition and edges of which were somewhat blurred (FIGS. 8A, 8B). After PK digestion (FIGS. 8C, 8D), the fibrils within these bundles were better resolved, indicating that the PK resistant cores of the fibrils are coated with PK sensitive material, either the rHaPrP-sen that has yet to convert to a more resistant structure, the flexible N-termini projecting outwards, or both. In some instances more separated fibrils could be detected, although their tendencies to cluster together gave false impressions of increased width when viewed without further magnification. Storing the material in water further dissociated the bundles, yielding more clearly defined fibril clusters for comparison (FIGS. 8E, 8F). Widths of fibrils at their thinnest were approximately 2-3 nm. The rHaPrP-res$^{(spon)}$ fibrils preferentially clustered in what appeared to be doublets, with total widths of 6-8 nm, while those of rHaPrP-res$^{(Sc)}$ formed larger side by side clusters of up to 36 nm in width. Bars designate 100 nm.

FIG. 10 is a series of digital images of gels showing that tube shaking supports ultra-sensitive prion-seeded conversions of rPrP-sen. Purified PrP$^{Sc}$ (FIG. 10A) or scrapie brain homogenate (FIG. 10B) were used to seed the conversion of rHaPrP-sen to protease-resistant forms in QUIC reactions performed in 0.1% sodium dodecyl sulfate (SDS) and 0.1% Triton X-100 ($C_{14}H_{22}O(C_2H_4O)_n$, also known as octylphenoxypolyethoxyethanol; Octoxynol-9; 4-octylphenol polyethoxylate; or polyethylene glycol p-(1,1,3,3-tetramethylbutyl)-phenyl ether, octyl phenol ethoxylate, polyoxyethylene octyl phenyl ether), in PBS. PK digestions and immunoblotting of reaction aliquots were performed as described in Example 8. The C-terminal polyclonal antibody R20 was used in the immunoblots. Circles designate the 17-kDa rHaPrP-res(Sc) band and brackets designate the position of the ≦13 kDa rHaPrP-res(Sc) bands. FIG. 10A shows a comparison of PK-resistant QUIC reaction products from duplicate 24-hour unshaken reactions and reactions shaken with or without 0.1 mm glass cell disruption beads (Scientific Industries). 50 µl reactions were seeded containing 0.1 mg/ml (4 µM) hamster rPrP-sen with 10 ng of purified hamster PrPSc and subjected the tubes to cycles of 2 minutes of shaking and 28 minutes without shaking at 37° C. Enhanced rHaPrP-res (Sc) formation was noted in the shaken reactions, but the beads were not influenced. 100 ng of rPrP-sen without PK-treatment is shown in lane 1. FIG. 10B shows 20-hour QUIC reactions performed with the designated rPrP-sen concentrations, reaction volumes, and seed amounts. The seed amounts indicate the estimated quantity of PrP$^{Sc}$ added in 2-µl aliquots of scrapie brain homogenate diluted in 1% normal brain homogenate. Lanes 6, 12, 18, and 24 received aliquots of only 1% normal brain homogenate. The tubes were subjected to cycles of 10 seconds of shaking and 110 seconds without shaking. The asterisk marks the position of rHaPrP-res(spon) bands.

FIG. 13 is a digital image of gels showing the results of seeding QUIC reactions with CSF. Aliquots (2 µl) of CSF taken from normal hamsters (n=3) or hamsters in the clinical phase of scrapie (n=6) were used to seed QUIC reactions using the conditions described for FIG. 12. Immunoblots of the PK-digested products of the first 48-hour round are shown in FIG. 13A. Ten percent of each first round reaction volume was used to seed a second 48-hour round of QUIC and the PK-digested products of the latter are shown in FIG. 13B. Antibodies R20 (top) and D13 (bottom) were used for the immunoblots. Lane 1 of each panel shows 100 ng HaPrP-sen without PK treatment. The positions of the 17-kDa rHaPrP-res$^{(Sc)}$ band are marked with a circle. The positions of molecular mass markers are designated in kDa on the left. These 37° C. reactions contained 0.05% SDS and 0.05% Triton X-100 in PBS and were shaken at 1500 rpm for 10 seconds every 2 minutes.

FIG. 14 is a digital image of gels showing ultrasensitive prion-seeded conversions of rPrP-sen in single-round 46-hour QUIC reactions at 45° C. Scrapie brain homogenate was used to seed the conversion of rHaPrP-sen to protease-resistant forms in QUIC reactions (0.1% SDS and 0.1% Triton X-100, in PBS). The reactions were shaken at 1500 rpm for 10 s every 2 min. PK digestions and immunoblotting of reaction aliquots were performed with the C-terminal antibody R20. Circles designate the 17-kDa rHaPrP-res (Sc) band and brackets designate the position of the $\leq$13 kDa rHaPrP-res(Sc) bands. FIG. 14A illustrates the sensitivity of the reaction with dilutions of normal brain homogenate (NBH) and scrapie brain homogenate (ScBH) as seeds. The ScBH seeds contained the designated amounts of PrPSc. The NBH was 0.00001% w/v in the reaction, which is equivalent to that of the ScBH seed dilution containing 1 pg of PrPSc. The NBH and ScBH samples were diluted to the designated levels in 1% N-2 supplement (Invitrogen), except in the lanes marked 1 pg*, which were diluted in 0.1% N-2. Either NBH or N-2 can be used as a diluent. FIG. 14B is an analysis of multiple negative controls under the reactions conditions of FIG. 14A. The ScBH seeds contained 1 pg of PrPSc while the NBH content in the negative controls are as designated. The lanes marked none were seeded with the diluent for the brain homogenates, i.e., N-2. Molecular mass markers are designated on the left.

FIG. 15 is a pair of digital images of gels showing that extended reactions can enhance QUIC sensitivity to small amounts of scrapie brain homogenate seed. In FIG. 15A, 40-hour QUIC reactions were performed with 0.1 mg/ml rPrP-sen and the designated reaction volumes and seed amounts using the shaking cycle and buffer conditions described for FIG. 10B. The upper and lower panels show immunoblots performed using antibody R20 and D13, respectively (PrP epitope residues shown in parentheses). In FIG. 15B, 65-hour (upper blot) and 95-hour (lower blot) QUIC reactions were performed as in FIG. 15A using 100-µl reaction volumes and dilutions of scrapie brain homogenate containing the designated amount of PrP$^{Sc}$. The lanes marked 'none' received comparable amounts of normal brain homogenate only. Antiserum R20 was used for these blots. Open circles designate the 17-kDa rHaPrP-res$^{(Sc)}$ band and brackets designate the positions of the 10-13 kDa rHaPrP-res$^{(Sc)}$ or rHaPrP-res$^{(spon)}$ bands. The positions of molecular mass markers are designated in kDa on the left. FIG. 11 and FIG. 15B provide results from the same experiment.

FIG. 16 is a series of digital images showing the effect of temperature on QUIC reaction products and kinetics. QUIC reactions were seeded at different temperatures and reaction times with scrapie brain homogenates (diluted in N2) containing the designated amount of PrP$^{Sc}$ or normal brain homogenate (NBH) at the dilution used for the 100-fg scrapie brain homogenate sample. The PK-digested products were immunoblotted with antibody R20. Rows FIGS. 16A, 16B, 16C, and 16D show reactions performed at 37° C., 45° C., 55° C. and 65° C., respectively. Successive columns of blots show reactions run for 4, 8 and 18 hours. All of the QUIC reactions were run in 0.1% SDS and 0.1% Triton X-100 in PBS with 0.1 mg/ml rPrP-sen with 60 seconds of shaking at 1500 rpm and 60 seconds of rest. The reaction products were digested with PK under the Sarkosyl-containing conditions described in Example 8. The positions of molecular mass markers are designated in kDa on the left in the first column or by corresponding tick marks by the other columns. The open circles designate the position of the 17 kDa band and the bracket the 10-13 kDa bands.

FIG. 17 illustrates the effect of shaking variations on the QUIC reaction. QUIC reactions were subjected to cycles of 10 seconds shaking and 110 seconds res (top panel) with reactions shaken for 60 seconds and rested for 60 seconds (bottom panel). These reactions were seeded with scrapie brain homogenate (NBH) at dilutions identical to that used for the 10 fg scrapie brain homogenate sample. The reaction temperature was 45° C. and the QUIC buffer conditions, PK-digestion and immunoblot protocols were as described for FIG. 18. The positions of molecular mass markers are designated in kDa on the left; the open circles designate the position of the 17 kDa band and the bracket the 10-13 kDa bands.

SEQUENCE LISTING

Figure 1A:
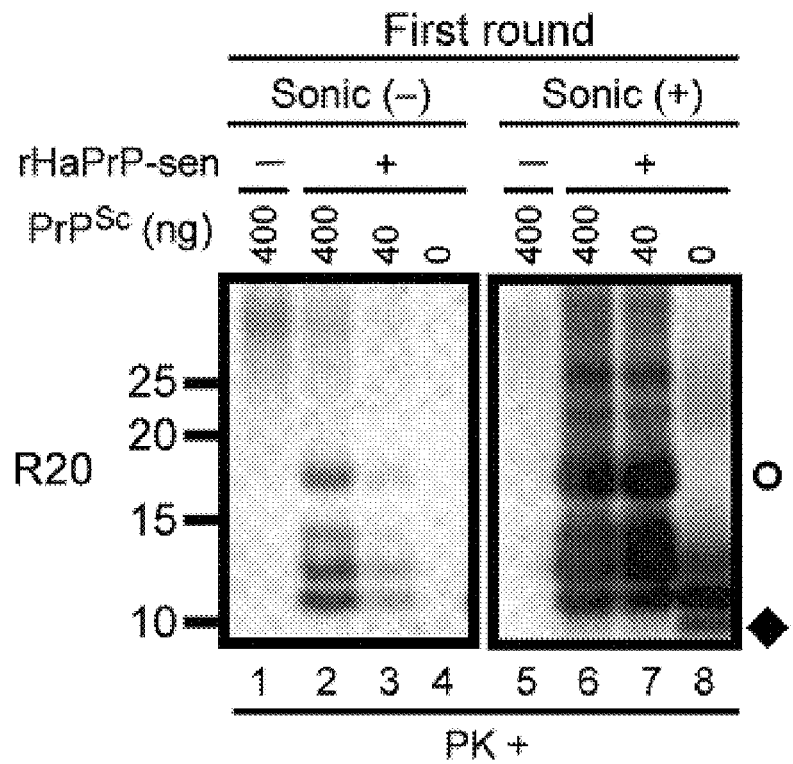
FIG. 1A is a digital image of a gel comparing the results of the assay when a designated amount of purified HaPrP$^{Sc}$ was incubated with 0.2 mg/ml rHaPrP-sen in 0.1% sodium dodecyl sulphate (SDS) and 0.1% TX-100 in phosphate buffered saline (PBS) for 24 hours, with (lanes 5-8) or without (lanes 1-4) periodic sonication (a 40-second pulse every hour). rHaPrP-sen was omitted from reactions shown in lanes 1 and 5. The reactions were digested with proteinase K (PK; 0.025:1 PK/rPrP weight/weight) and equivalent aliquots were subjected to immunoblotting using the polyclonal antibody R20, which was raised against prion protein residues 219-232. Open circles and black diamonds mark the 17- and 10-kDa fragments, respectively.
Figure 1B:
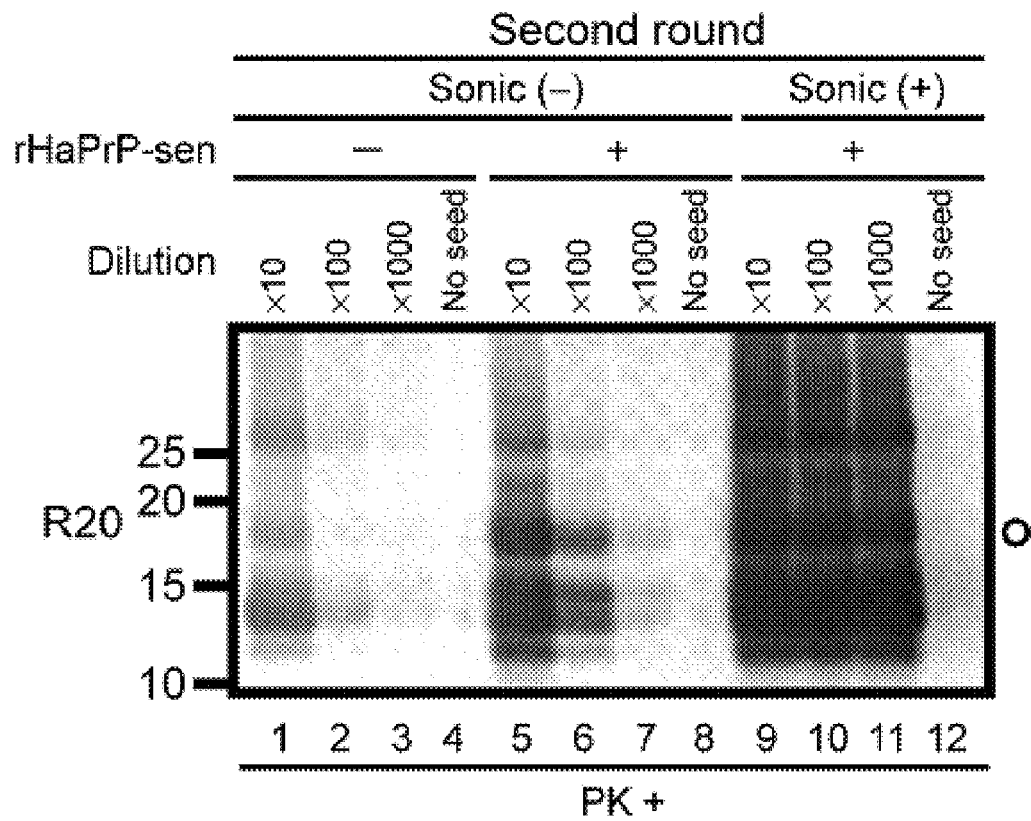
FIG. 1B is a digital image of a gel showing the results of the assay when aliquots of first round HaPrP$^{Sc}$-seeded, sonicated reaction products shown in lane 7 of FIG. 1A were diluted by the designated factors into fresh rHaPrP-sen and subjected to a second round of sonicated or unsonicated reactions and PK treatments as in FIG. 1A. Lanes designated "No seed" indicate reactions that were left unseeded.
Figure 1C:
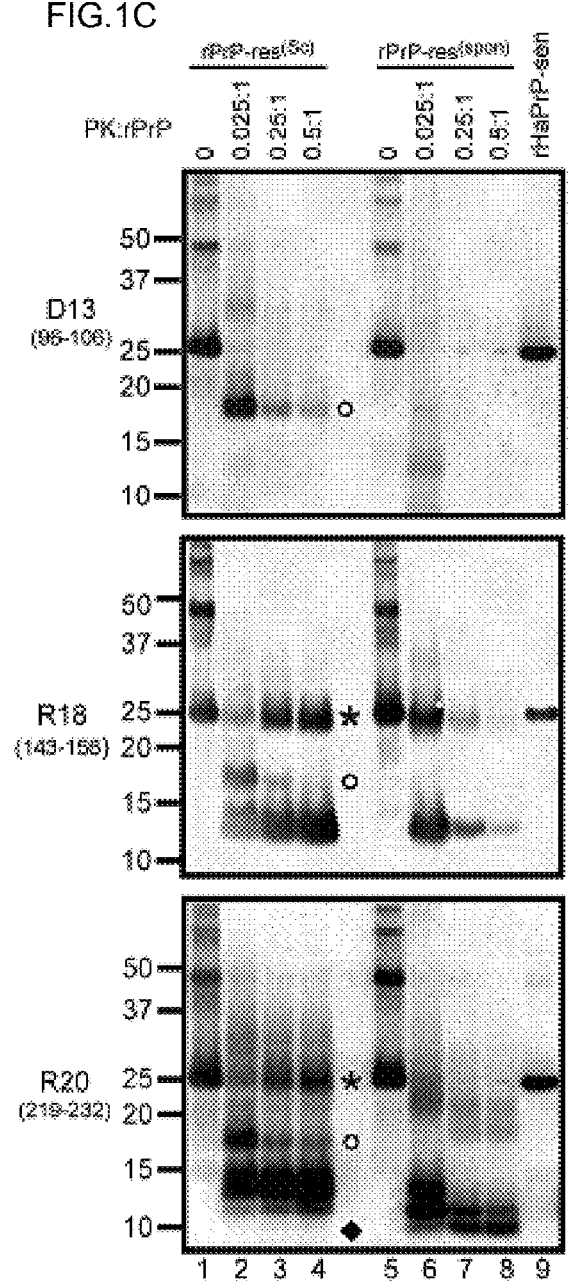
FIG. 1C is a series of digital images of three gels showing the antibody reactivity of PK-treated reaction products, which was determined after three sequential rounds of reactions seeded in the first round with 0 or 40 ng PrP$^{Sc}$. The reactions were diluted 100-fold into fresh rHaPrP-sen between each round. The third round reactions were digested with the designated PK:PrP ratios and analyzed by immunoblot with D13, R18 and R20 antibodies. The respective antibody epitopes are contained within the prion protein residues indicated in parentheses. Lanes 1 and 5 show 2 µl samples (400 ng of rHaPrP) without PK digestion. Lane 9 is 100 ng rHaPrP-sen without PK digestion. Asterisks indicate dimer formed from 12-13 kDa fragments, suggested by their size and lack of recognition by D13, an antibody which would react with full-length rPrP but not with a dimer of 13-kDa fragments containing the C-terminal epitope of R20.
Figure 1D:
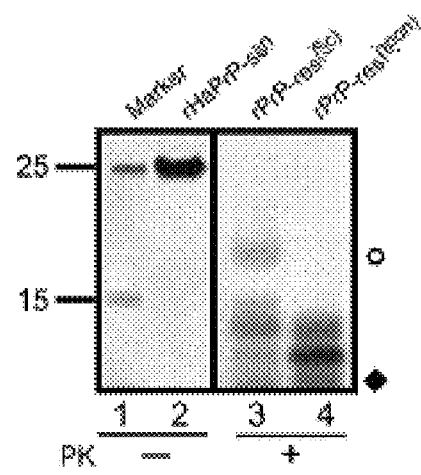
FIG. 1D is a digital image showing silver staining of rHaPrP-res$^{(Sc)}$ or unseeded (rHaPrP-res$^{(spon)}$) third-round after PK digestion (0.025:1 PK/rPrP). Positions of molecular mass markers are designated in kDa.
Figure 2A:
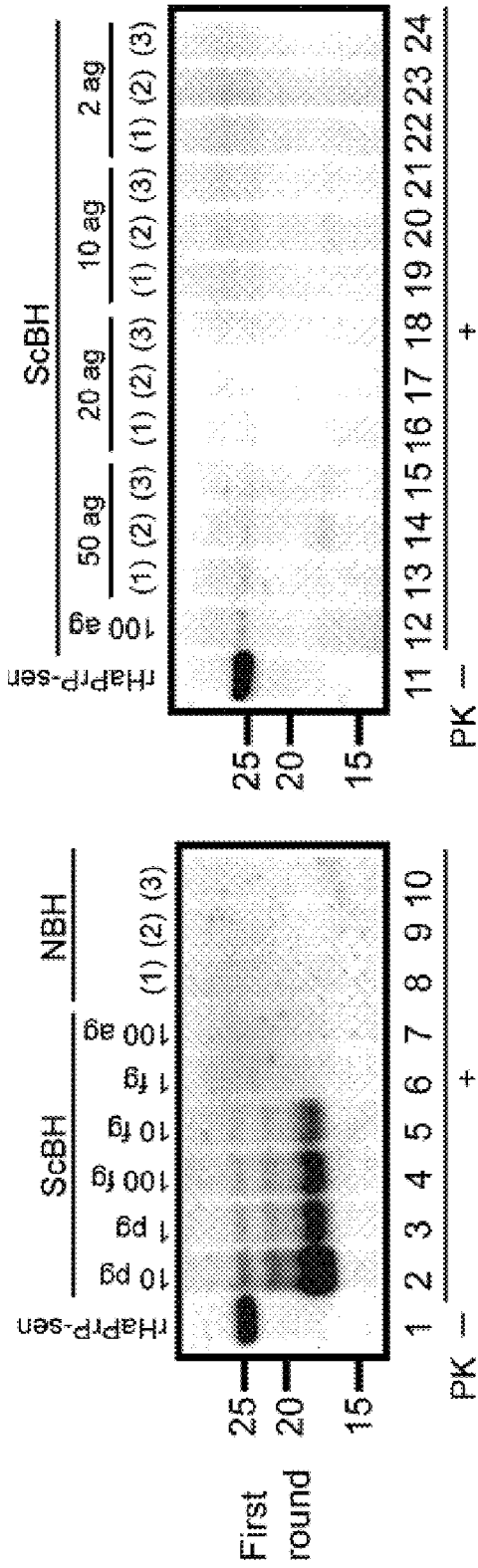
FIG. 2A is a pair of digital images showing the results of the first round of rPrP-PMCA. Serially diluted scrapie brain homogenate (ScBH) containing the designated amounts of PrP$^{Sc}$ was used as seeds. Normal brain homogenate (NBH) (1%) was used for negative controls (lanes 8-10) and as a diluent for the ScBH. The reactions seeded with 2-50 ag of PrP$^{Sc}$ or NBH were done in triplicate. Untreated rHaPrP-sen is shown in lanes 1 and 11. All other samples were treated with PK (0.025:1 PK/rPrP wt/wt ratio) for 1 hour at 37° C. Samples were probed with anti-PrP monoclonal antibody D13.
Figure 2B:
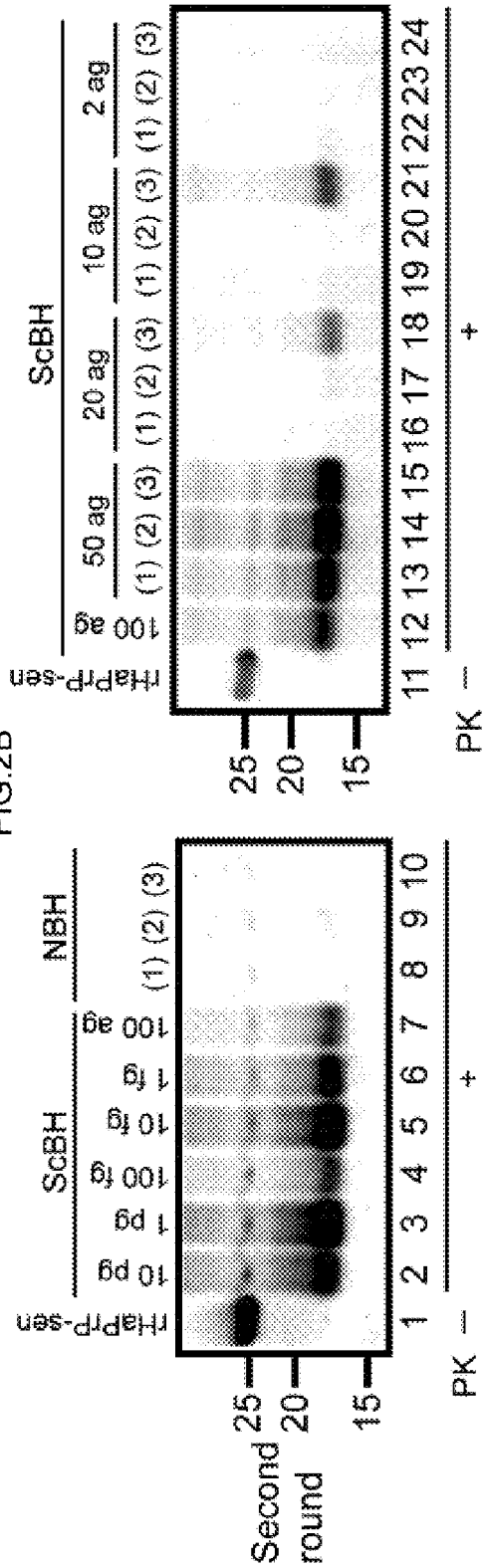
FIG. 2B is a pair of digital images showing the results of the second round of rPrP-PMCA. One tenth volume (8 µl) of the first round samples was transferred to a newly prepared substrate mixture. PK digestion and immunoblotting were done as described in Example 1. Similar results were obtained in another independent experiment. Positions of molecular mass markers are designated in kDa.

The Sequence Listing is submitted as an ASCII text file 4239-77856-04_Sequence_Listing.txt, Oct. 7, 2011, 21.8 KB], which is incorporated by reference herein.

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NO: 1 is an amino acid sequence of a recombinant Syrian golden hamster proteinase K-sensitive prion protein.
kkrpkpgg wntggsrypg qgspggnryp pqgggtwgqp hgggwgqphg ggwgqphggg wgqphgggwg qgggthnqwn kpnkpktsmk hmagaaaaga vvgglggyml gsamsrpmlh fgndwedryy renmnrypnq vyyrpvdqyn nqnnfvhdcv nitikqhtvt tttkgenfte tdvkmmervv eqmcvtqyqk esqayydgrr s SEQ ID NO: 2 is an amino acid sequence of a recombinant mouse (Prnp-a) proteinase K-sensitive prion protein.
kkrpkpgg wntggsrypg qgspggnryp pqggtwgqph gggwgqphgg swgqphggsw gqphgggwgq gggthnqwnk pskpktnlkh vagaaaagav vgglggymlg samsrpmihf gndwedryyr enmyrypnqv yyrpvdqysn qnnfvhdcvn itikqhtvtt ttkgenftet dvkmmervve qmcvtqyqke sqayydgrrs SEQ ID NO: 3 is an amino acid sequence of a recombinant human (129M) proteinase K-sensitive prion protein.
kkrpkpgg wntggsrypg qgspggnryp pqggggwgqp hgggwgqphg ggwgqphggg wgqphgggwg qgggthsqwn kpskpktnmk hmagaaaaga vvgglggyml gsamsrpiih fgsdyedryy renmhrypnq vyyrpmdeys nqnnfvhdcv nitikqhtvt tttkgenfte tdvkmmervv eqmcltqyer esqayyqrgs s SEQ ID NO: 4 is an amino acid sequence of a recombinant human (129V) proteinase K-sensitive prion protein.
kkrpkpgg wntggsrypg qgspggnryp pqggggwgqp hgggwgqphg ggwgqphggg wgqphgggwg qgggthsqwn kpskpktnmk hmagaaaaga vvgglggyvl gsamsrpiih fgsdyedryy renmhrypnq vyyrpmdeys nqnnfvhdcv nitikqhtvt tttkgenfte tdvkmmervv eqmcitqyer esqayyqrgs s SEQ ID NO: 5 is an amino acid sequence of a recombinant bovine (6-octarepeat) proteinase K-sensitive prion protein.
kkrpkp gggwntggsr ypgqgspggn ryppqggggw gqphgggwgq phgggwgqph gggwgqphgg gwgqphgggg wqggthgqw nkpskpktnm khvagaaaag avvgglggym lgsamsrpli hfgsdyedry yrenmhrypn qvyyrpvdqy snqnnfvhdc vnitvkehtv ttttkgenft etdikmmerv veqmcltqyq resqayyqrg as SEQ ID NO: 6 is an amino acid sequence of a recombinant ovine (136A 154R 171Q) proteinase K-sensitive prion protein.
kkrpkp gggwntggsr ypgqgspggn ryppqggggw

```
gqphgggwgq phgggwgqph gggwgqphgg ggwgqggshs qwnkpskpkt nmkhvagaaa agavvgglgg ymlgsamsrp lihfgndyed ryyrenmyry pnqvyyrpvd qysnqnnfvh dcvnitvkqh tvttttkgen ftetdikime rvveqmcitq yqresqayyq rga
```

SEQ ID NO: 7 is an amino acid sequence of a recombinant Deer (96G 132M 138S) proteinase K-sensitive prion protein.
```
kkrpkp gggwntggsr ypgqgspggn ryppqggggw gqphgggwgq phgggwgqph gggwgqphgg ggwgqggths qwnkpskpkt nmkhvagaaa agavvgglgg ymlgsamsrp lihfgndyed ryyrenmyry pnqvyyrpvd qynnqntfvh dcvnitvkqh tvttttkgen ftetdikmme rvveqmcitq yqresqayyq rgas
```

SEQ ID NO: 8 is an amino acid sequence of a full-length Syrian golden hamster proteinase K-sensitive prion protein.
```
mwtdvglckk rpkpggwntg gsrypgqgsp ggnryppqgg gtwgqphggg wgqphgggwg qphgggwgqp hgggwgqggg thnqwnkpsk pktnmkhmag aaaagavvgg lggymlgsam srpmmhfgnd wedryyrenm nrypnqvyyr pvdqynnqnn fvhdcvniti kqhtvttttk genftetdik imervveqmc ttqyqkesqa yydgrrssav lfssppvill isfliflmvg
```

SEQ ID NO: 9 is an amino acid sequence of a full-length mouse (Prnp-a) proteinase K-sensitive prion protein.
```
manlgywlla lfvtmwtdvg lckkrpkpgg wntggsrypg qgspggnryp pqggtwgqph gggwgqphgg swgqphggsw gqphgggwgq gggthnqwnk pskpktnlkh vagaaaagav vgglggymlg samsrpmihf gndwedryyr enmyrypnqv yyrpvdqysn qnnfvhdcvn itikqhtvtt ttkgenftet dvkmmervve qmcvtqyqke sqayydgrrs sstvlfsspp villisflif livg
```

SEQ ID NO: 10 is an amino acid sequence of a full-length human (129M) proteinase K-sensitive prion protein.
```
manlgcwmlv lfvatwsdlg lckkrpkpgg wntggsrypg qgspggnryp pqggggwgqp hgggwgqphg ggwgqphggg wgqphgggwg qgggthsqwn kpskpktnmk hmagaaaaga vvgglggyml gsamsrpiih fgsdyedryy renmhrypnq vyyrpmdeys nqnnfvhdcv nitikqhtvt tttkgenfte tdvkmmervv eqmcitqyer esqayyqrgs smvlfssppv illisflifl ivg
```

SEQ ID NO: 11 is an amino acid sequence of a full-length human (129V) proteinase K-sensitive prion protein.
```
manlgcwmlv lfvatwsdlg lckkrpkpgg wntggsrypg qgspggnryp pqggggwgqp hgggwgqphg ggwgqphggg wgqphgggwg qgggthsqwn kpskpktnmk hmagaaaaga vvgglggyvl gsamsrpiih fgsdyedryy renmhrypnq vyyrpmdeys nqnnfvhdcv nitikqhtvt tttkgenfte tdvkmmervv eqmcitqyer esqayyqrgs smvlfssppv illisflifl ivg
```

DETAILED DESCRIPTION OF SEVERAL EMBODIMENTS

I. Overview of Several Embodiments

Disclosed herein is an ultrasensitive method, termed rPrp-res amplification, for detecting PrP$^{Sc}$ that allows the use of purified recombinant rPrP-sen as a substrate for seeded polymerization. The resulting assay is much faster than previous PMCA methods, and the use of rPrP-sen facilitates improved prion assays and fundamental studies of structure and formation of PrP$^{Sc}$. These methods can be used to diagnose a variety of diseases in animal and human subjects, and reduce the time necessary for high sensitivity detection of PrP-res in samples. Thus, the present disclosure also enables high throughput, accurate and sensitive screening of samples, as well as diagnosis of clinical disease.

In certain embodiments, the methods are used to diagnose a prion disease or a disease induced by a protein conformation change, such as a conformational change in PrP-sen. The disease can be a transmissible spongiform encephalopathy, such as bovine spongiform encephalopathy (BSE) in a cow, whereas in sheep, the methods are used to diagnose scrapie, and in deer, elk, and moose the methods are used to diagnose CWD. The method also enables the rapid testing of live animals for infection to protect against unnecessary culling of herds or inadvertent introduction of prions into the food chain.

The disclosed methods also are used to diagnose humans and human diseases. Prion diseases that the methods detect in humans include but are not limited to Creutzfeldt-Jakob disease (CJD), kuru, fatal familial insomnia, Gerstmann-Straussler-Scheinker disease, and sporadic fatal insomnia. As when used for the diagnosis of animal diseases, the disclosed methods offer significant advantages over available methods for diagnosis of these neurologic disorders. For instance, cognitive tests and clinical signs currently used for diagnosis of CJD can only indicate a probable diagnosis, and conventional PMCA takes up to three weeks to perform, whereas the disclosed methods provide an objective method by which positive diagnosis can be made within 1-2 days with little chance of false positive or false negative results. Additionally, the sensitivity of the test enables the detection of disease from peripheral tissues, such as blood and cerebral spinal fluid (CSF), which is much less invasive and expensive than brain biopsy procedures. The methods also provide sensitivity that is sufficiently high to detect or diagnose disease prior to the onset of clinical symptoms.

One embodiment of the disclosure is a method for detecting PrP-res in a sample. The method includes (a) mixing the sample with purified rPrP-sen to make a reaction mix (b) performing a primary reaction that includes (i) incubating the reaction mix to permit the coaggregation of the rPrP-sen with the PrP-res that may be present in the reaction mix; (ii) agitating any aggregates formed during step (i); and (iii) repeating steps (i) and (ii) one or more times. In step (i) of the primary reaction, aggregation of the rPrP-sen with the PrP-res results in a conversion of the rPrP-sen to rPrP-res$^{(Sc)}$. These amplification steps are then followed by (c) detecting rPrP-res$^{(Sc)}$ in the reaction mix, wherein detection of rPrP-res$^{(Sc)}$ in the reaction mix indicates that PrP-res was present in the sample. In some examples, steps (b)(i) and (b)(ii) are repeated from about 1 to about 200 times. In other examples, serial amplification is performed by removing a portion of the reaction mix and incubating it with additional rPrP-sen.

The reaction can be carried out by maintaining incubation conditions to inhibit production of rPrP-res$^{(spon)}$ which in the past has competed with the desired reaction and may have contributed to the conclusion that cyclic amplification could not be carried out with rPrP-sen. The detailed description describes a number of ways to inhibit production of rPrP-res$^{(spon)}$, for example by one or more of (a) agitating the aggregates by shaking the reaction mix without sonication; (b) incubating the reaction mix in 0.05% to 0.1% of a detergent; (c) incubating the reaction mix at 37° C.-60° C.; or (d) incubating the reaction mix for no more than 2, 4, 6, 8, 16 or 20 hours at higher reaction temperatures. In certain examples, any combination of (a)-(d) or all of them are used to inhibit rPrP-res$^{(spon)}$ production, such that the amount of rPrP-res$^{(spon)}$ is less than 20% (or even less than 15% or 10%) of that of rPrP-res$^{(Sc)}$ generated (in reactions seeded with samples containing PrP-res). The detergent may be a mixture of detergents, such as a mixture of an anionic and nonionic detergent, such as SDS and Triton X-100.

In certain embodiments, the method also includes the step of performing a serial amplification reaction before detecting rPrP-res$^{(Sc)}$ in the reaction mix, wherein performing the serial reaction includes removing a portion of the reaction mix and incubating it with additional rPrP-sen. In other embodiments, detecting the PrP-resincludes detecting rPrP-res$^{(Sc)}$ aggregates in the reaction mix. Still other embodiments also include digesting the reaction mix with proteinase K prior to detecting rPrP-res$^{(Sc)}$ in the reaction mix. In certain examples, detecting rPrP-res$^{(Sc)}$ includes using an antibody that specifically binds to prion protein, for instance D13, R18, or R20 antibodies.

In some embodiments of the disclosure, the PrP-res includes mammalian prion protein, and in certain examples, the rPrP-sen includes a detectable label. In other embodiments, incubating the reaction mix includes incubating the reaction mix at about 25 to 70° C., and in particular examples incubating the reaction mix includes incubating the reaction mix at about 37 to 55° C., or 45 to 55° C. In some examples, incubating the reaction mix includes incubating the reaction mix between agitations for about 1 to about 180 minutes, and in particular examples incubating the reaction mix includes incubating the reaction mix for 1 min or for about 60 to about 120 minutes, such as about 60, about 70, about 80, about 90, about 100, about 110 or about 110 minutes, for example about 70 to about 100 minutes. In other examples, the reaction mix can be incubated for about 1, about 2, about 5, about 10, about 20, about 30, about 40 minutes between agitations. The total reaction time, including agitation and incubation can be about 2 to about 48 hours, such as about 4, about 6, about 8, about 16, about 20, about 24, about 36, about 42, or about 48 hours.

In some examples of rPrP-PMCA, agitating the aggregates includes sonicating the reaction mix, and in some examples, agitating the reaction mix includes sonicating the reaction mix for about 1-120 seconds, or in other examples, for about 40 seconds. In other embodiments, termed QUIC, agitating the reaction mix includes shaking the reaction mix for about 1-120 seconds, for instance for about 10 or 60 seconds. The primary reaction includes, in some embodiments, (a) incubating the reaction mix for approximately 60 minutes; and (b) sonicating the reaction mix for approximately 40 seconds. In some examples, steps (a) and (b) are repeated for approximately 1-48 hours.

In other examples, the reaction mixture further includes an ionic (such as an anionic) and a nonionic detergent, such as SDS and TRITON® (TX)-100, for example, from about 0.05% to about 0.1% SDS and from about 0.05% to about 0.1% TX-100. Other suitable non-ionic detergents include Bis(polyethylene glycol bis[imidazoyl carbonyl]), Decaethylene glycol monododecyl ether, N-Decanoyl-N-methylglucamine, n-Decyl a-D-glucopyranoside, Decyl b-D-maltopyranoside, n-Dodecanoyl-N-methylglucamide, n-Dodecyl a-D-maltoside, n-Dodecyl b-D-maltoside, n-Dodecyl b-D-maltoside, SigmaUltra, Heptaethylene glycol monodecyl ether, Heptaethylene glycol monododecyl ether, Heptaethylene glycol monotetradecyl ether, n-Hexadecyl b-D-maltoside, Hexaethylene glycol monododecyl ether, Hexaethylene glycol monohexadecyl ether, Hexaethylene glycol monooctadecyl ether, Hexaethylene glycol monotetradecyl ether, Methyl-6-O—(N-heptylcarbamoyl)-a-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-b-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, SPAN® (Nos. 20, 40, 60, 65, 80, or 85), Tergitol (Type 15-S-12, Type 15-S-30, Type 15-S-5, Type 15-S-7, Type 15-S-9, Type NP-10, Type NP-4, Type NP-40, Type NP-7, Type NP-9, MIN FOAM 1x, MIN FOAM 2x, Type TMN-10, Type TMN-6), Tetradecyl-b-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, TRITON® CF-21, TRITON® CF-32, TRITON® DF-12, TRITON® DF-16, TRITON® GR-5M, Triton X-100, Triton X-102, TRITON® X-15, TRITON® X-151, TRITON® X-207, TRITON® X-100, TRITON® X-114 TRITON® X-165, TRITON® X-305, TRITON® X-405, TRITON® X-45, TRITON® X-705-70, TWEEN® 20, TWEEN® 21, TWEEN® 40, TWEEN® 60, TWEEN® 6, TWEEN® 65, TWEEN® 80, TWEEN® 81, TWEEN® 85, Tyloxapol, and n-Undecyl b-D-glucopyranoside. Other suitable anionic detergents of use include Chenodeoxycholic acid, Chenodeoxycholic acid sodium salt, Cholic acid, ox or sheep bile, Dehydrocholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate (Glycodeoxycholic acid monohydrate, Glycodeoxycholic acid sodium salt, Glycolithocholic acid 3-sulfate disodium salt, Glycolithocholic acid ethyl ester), N-Lauroylsarcosine, Lithium dodecyl sulfate, Niaproof 4, TRITON® QS-15, TRITON® QS-44, 1-Octanesulfonic acid sodium salt, Sodium 1-butanesulfonate, Sodium 1-decanesulfonate, Sodium 1-dodecanesulfonate, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurodeoxycholic acid sodium salt monohydrate, Taurohyodeoxycholic acid sodium salt hydrate, Taurolithocholic acid 3-sulfate disodium salt Tauroursodeoxycholic acid sodium salt, TRITON® X-200M TRITON® XQS-20, TRIZMA® dodecyl sulfate, and Ursodeoxycholic acid. The anionic and inonic detergents can be used for example, at a concentration of 0.01% to 0.5%, such as 0.05% to 0.1%.

In some embodiments, the source of the recombinant rPrP-sen is the same species as the source of the sample or it is of a different species as the source of the sample. It has particularly been found that rHaPrP-sen is well suited to the amplification reaction, and can be used to amplify target protein in a target from species other than hamster. Some examples of the method include a rPrP-sen that is bovine, ovine, hamster, rat, mouse, canine, feline, cervid, human, or non-human primate rPrP-sen. In certain examples, the rPrP-sen includes amino acids 23-231 (SEQ ID NO: 1) of Syrian golden hamster prion protein (SEQ ID NO: 8), amino acids 23-231 (SEQ ID NO: 2) of mouse prion protein (SEQ ID NO: 9), amino acids 23-231 (SEQ ID NO: 3) of human (129M) prion protein (SEQ ID NO: 10), amino acids 23-231 (SEQ ID NO: 4) of human (129V) prion protein (SEQ ID NO: 11), amino acids 25-241 (SEQ ID NO: 5) of bovine (6-octarepeat) prion protein, amino acids 25-233 (SEQ ID NO: 6) of ovine (136A 154R 171Q) prion protein, or amino acids 25-234 (SEQ ID NO: 7) of deer (96G 132M 138S) prion protein. However, fragments of rPrP-sen can also be used, such as but not limited to a fragment comprising amino acids 23-231 of rPrP-sen. Fragments include amino acids 30-231, amino acids 40-231, amino acids 50-231, amino acids 60-231, amino acids 70-231, amino acids 80-231 or amino acids 90-231 of mouse, human, hamster, bovine, ovine or deer prion protein. A functional fragment of rPrP-sen can aggregate with PrP-res and result in a conversion of the rPrP-sen to rPrP-res$^{(Sc)}$. It should be noted that chimeric rPrP-sen, wherein a portion of the protein is from one species, and a portion of the protein is from another species, can also be utilized. In one example about 10 to about 90%, such as about 10%, about 20%, about 30%, about 40%, about 50%, about 60%, about 70% about 80% or about 90% of the rPrP-sen is from one species, and, correspondingly, about 90%, about 80%, about 70%, about 60%, about 50%, about 40%, about 30%, about 20% or about 10% is from another species. Chimeric proteins can include, for example, hamster rPrP-sen and rPrP-sen from another species, such as human PrP-sen.

Particular examples include a sample that is a tissue sample from an animal, for instance a brain sample, a peripheral organ sample, feces, urine, mucosal secretions, or a CSF sample. In even more particular examples, the peripheral organ sample includes blood, tonsil, nasal tissue, spleen, or another lymphoid organ.

Detecting PrP-res$^{(Sc)}$ in the reaction mix includes, in some embodiments, performing a Western blot, an ELISA assay, a CDI assay, a DELPHIA assay, a strip immuno-chromatographic assay, a spectroscopic assay, a fluorescence assay, or a radiometric assay. In certain examples, the ELISA assay is a two-site immunometric sandwich ELISA. In particular examples, the prion can be detected in a sample containing at least 1000 PrP$^{Sc}$ molecules. In still more particular examples, the method further includes inactivating residual PrP-res in the reaction mix. In yet other examples, the method is a method of diagnosing a prion disease.

Also disclosed herein are kits for detection of a prion in a sample that include rPrP-sen and at a reaction mix buffer. In some embodiments, the reaction mix buffer includes SDS and TX-100, and in other embodiments, the rPrP-sen is lyophilized. In certain examples, the kit also includes one or more of (a) a decontamination solution; (b) a positive control; (c) a negative control; or (d) reagents for the detection of rPrP-res$^{(Sc)}$. In particular examples, the reagents for detection of rPrP-res$^{(Sc)}$ include antibodies.

In yet other embodiments, a rPrP-res amplification method is disclosed for detecting PrP-res in a sample by (a) mixing the sample with purified rPrP-sen to make a reaction mix; and performing an amplification reaction in a single round without serial amplification, by incubating the reaction mixture to permit coaggregation of the rPrP-sen with the PrP-res that may be present in the reaction mix, wherein coaggregation of the rPrP-sen with the PrP-res results in a conversion of the rPrP-sen to the rPrP-res$^{(Sc)}$. Using this method it is possible to sensitively detect PrP-res in a sample under a variety of conditions, such as conditions (b) through (e) below:

(b) detecting PrP-res in a sample containing as little as 100 ag PrP-res by incubating the reaction mixture at 45° C. for about 46 hours and intermittently shaking the reaction mixture without sonication, and rPrP-res$^{(Sc)}$ is detected as an indicator of the initial presence of PrP-res;

(c) detecting PrP-res in a sample containing as little as 1 fg PrP-res by incubating the reaction mixture at 55° C. for about 18 hours and intermittently shaking the reaction mixture without sonication, and rPrP-res$^{(Sc)}$ is detected as an indicator of the initial presence of PrP-res;

(d) detecting PrP-res in a sample containing as little as 10 fg PrP-res by incubating the reaction mixture at 55° C. for about 8 hours and intermittently shaking the reaction mixture without sonication, and rPrP-res$^{(Sc)}$ is detected as an indicator of the initial presence of PrP-res; and (e) detecting PrP-res in a sample containing as little as 100 fg PrP-res by incubating the reaction mixture at 65° C. for about 4 hours and intermittently shaking the reaction mixture without sonication, and rPrP-res$^{(Sc)}$ is detected as an indicator of the initial presence of PrP-res.

II. Abbreviations

BH: brain homogenate
BSE: bovine spongiform encephalopathy
CJD: Creutzfeldt-Jakob disease
CSF: cerebral spinal fluid
CWD: chronic wasting disease
EEG: electroencephalogram
ELISA: enzyme linked immunosorbent assays
EUE: exotic ungulate encephalopathy
fCJD: familial Creutzfeldt-Jakob disease
FFI: fatal familial insomnia
GFP: green fluorescent protein
GSS: Gerstmann-Straussler Sheinker syndrome
GST: Glutathione S-transferase
HaPrP-res: hamster proteinase K resistant prion protein
HaPrP$^{Sc}$: hamster proteinase K resistant prion protein
HaPrP-sen: hamster proteinase K sensitive prion protein
iCJD: iatrogenic Creutzfeldt-Jakob disease MBP: Maltose binding protein
NBH: normal brain homogenate
PBS: phosphate buffered saline
PK: proteinase K
PMCA: protein misfolding cyclic amplification
PrP-res: proteinase K resistant prion protein
$PrP^{Sc}$: proteinase K resistant prion protein
PrP-sen: proteinase K sensitive prion protein
QUIC: quaking-induced conversion
RIA: radioimmunoassay
rHaPrP-res$^{(vCJD)}$: recombinant hamster proteinase K resistant prion protein, variant Creutzfeldt-Jakob disease that arises from seeding hamster PrP-res into a human sample
rPrP-res: recombinant proteinase K resistant prion protein
rPrP-res$^{(Sc)}$: recombinant proteinase K resistant prion protein seeded by $PrP^{Sc}$
rPrP-res$^{(spon)}$: recombinant proteinase K resistant prion protein that spontaneously arises without seeding (unseeded) by rPrP-res
rPrP-sen: recombinant proteinase K sensitive prion protein
ScBH: Scrapie brain homogenate
sCJD: sporadic Creutzfeldt-Jakob disease
SDS-PAGE: sodium dodecyl sulphate-polyacrylamide gel electrophoresis
sFI: sporadic fatal insomnia
TSE: transmissible spongiform encephalopathy
TX-100: Triton X-100
vCJD: variant Creutzfeldt-Jakob disease

III. Terms

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural references unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described herein. The term "comprises" means "includes."

In order to facilitate review of the various embodiments of this disclosure, the following explanations of specific terms are provided:

Aggregate: as used herein, includes aggregates, dimers, multimers, and polymers of prion proteins, for instance aggregates, dimers, multimers, and polymers of PrP-res, rPrP-res, or rPrP-res$^{(Sc)}$.

Agitation: includes introducing any type of turbulence or motion into a mixture or reaction mix, for examples by sonication, stirring, or shaking. In some embodiments, agitation includes the use of force sufficient to fragment rPrP-res$^{(Sc)}$ aggregates, which disperses rPrP-res$^{(Sc)}$ aggregates and/or polymers to facilitate further amplification. In some examples fragmentation includes complete fragmentation, whereas in other examples, fragmentation is only partial, for instance, a population of aggregates can be about 1%, 2%, 5%, 10%, 20%, 30%, 40%, 50%, 60%, 70%, 80%, 90%, or 100% fragmented by agitation. Exemplary agitation methods are described in the Examples section below.

Conservative variant: in the context of a prion protein, refers to a peptide or amino acid sequence that deviates from another amino acid sequence only in the substitution of one or several amino acids for amino acids having similar biochemical properties (so-called conservative substitutions). Conservative amino acid substitutions are likely to have minimal impact on the activity of the resultant protein. Further information about conservative substitutions can be found, for instance, in Ben Bassat et al. (*J. Bacteriol.,* 169:751-757, 1987), O'Regan et al. (*Gene,* 77:237-251, 1989), Sahin-Toth et al. (*Protein Sci.,* 3:240-247, 1994), Hochuli et al. (*Bio/Technology,* 6:1321-1325, 1988) and in widely used textbooks of genetics and molecular biology. In some examples, prion protein variants can have no more than 1, 2, 3, 4, 5, 10, 15, 30, 45, or more conservative amino acid changes. Conservative variants are discussed in greater detail in section IV F of the Detailed Description.

In one example, a conservative variant prion protein is one that functionally performs substantially like a similar base component, for instance, a prion protein having variations in the sequence as compared to a reference prion protein. For example, a prion protein or a conservative variant of that prion protein, will aggregate with rPrP-sen (or $PrP^{Sc}$), for instance, and will convert rPrP-sen to rPrP-res (or will be converted to rPrP-res). In this example, the prion protein and the conservative variant prion protein do not have the same amino acid sequences. The conservative variant can have, for instance, one variation, two variations, three variations, four variations, or five or more variations in sequence, as long as the conservative variant is still complementary to the corresponding prion protein.

In some embodiments, a conservative variant prion protein includes one or more conservative amino acid substitutions compared to the prion protein from which it was derived, and yet retains prion protein biological activity. For example, a conservative variant prion protein can retain at least 10% of the biological activity of the parent prion protein molecule from which it was derived, or alternatively, at least 20%, at least 30%, or at least 40%. In some preferred embodiments, a conservative variant prion protein retains at least 50% of the biological activity of the parent prion protein molecule from which it was derived. The conservative amino acid substitutions of a conservative variant prion protein can occur in any domain of the prion protein.

Disaggregate: To partially or complete disrupt an aggregate, such as an aggregate of PrP-res, rPrP-res, or rPrP-res$^{(Sc)}$.

Encode: any process whereby the information in a polymeric macromolecule or sequence is used to direct the production of a second molecule or sequence that is different from the first molecule or sequence. As used herein, the term is construed broadly, and can have a variety of applications. In some aspects, the term "encode" describes the process of semi-conservative DNA replication, wherein one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (for instance, by the process of transcription incorporating a DNA-dependent RNA polymerase enzyme). Also, an RNA molecule can encode a peptide, as in the process of translation. When used to describe the process of translation, the term "encode" also extends to the triplet codon that encodes an amino acid. In some aspects, an RNA molecule can encode a DNA molecule, for instance, by the process of reverse transcription incorporating an RNA-dependent DNA polymerase. In another aspect, a DNA molecule can encode a peptide, where it is understood that "encode" as used in that case incorporates both the processes of transcription and translation.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a prion protein-encoding RNA, or a prion protein-encoding DNA.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ and/or Mg++ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

In a particular example, stringent conditions are hybridization at 65° C. in 6×SSC, 5×Denhardt's solution, 0.5% SDS and 100 μg sheared salmon testes DNA, followed by 15 30-minute sequential washes at 65° C. in 2×SSC, 0.5% SDS, followed by 1×SSC, 0.5% SDS and finally 0.2×SSC, 0.5% SDS.

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

Nucleic acid molecule: A polymeric form of nucleotides, which can include both sense and anti sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single and double stranded forms of DNA. A nucleic acid molecule can include either or both naturally occurring and modified nucleotides linked together by naturally occurring and/or non naturally occurring nucleotide linkages.

Prion: a type of infectious agent composed mainly of protein. Prions cause a number of diseases in a variety of animals, including bovine spongiform encephalopathy (BSE, also known as mad cow disease) in cattle and Creutzfeldt-Jakob disease in humans. All known prion diseases affect the structure of the brain or other neural tissue, and all are untreatable and fatal.

Prions are believed to infect and propagate by refolding abnormally into a structure that is able to convert normal molecules of the protein into the abnormally structured (for instance, PrP-res or $PrP^{Sc}$) form. Most, if not all, known prions can polymerize into amyloid fibrils rich in tightly packed beta sheets. This altered structure renders them unusually resistant to denaturation by chemical and physical agents, making disposal and containment of these particles difficult.

In prion diseases, the pathological, protease-resistant form of prion protein, termed $PrP^{Sc}$ or PrP-res, appears to propagate itself in infected hosts by inducing the conversion of its normal host-encoded protease-sensitive precursor, PrP-sen, into $PrP^{Sc}$. PrP-sen is a monomeric glycophosphatidylinositol-linked glycoprotein that is low in β-sheet content, and highly protease-sensitive. Conversely, $PrP^{Sc}$ aggregates are high in β-sheet content and partially protease-resistant. Mechanistic details of the conversion are not well understood, but involve direct interaction between $PrP^{Sc}$ and PrP-sen, resulting in conformational changes in PrP-sen as the latter is recruited into the growing $PrP^{Sc}$ multimer (reviewed in Caughey & Baron (2006) *Nature* 443, 803-810). Accordingly, the conversion mechanism has been tentatively described as autocatalytic seeded (or nucleated) polymerization.

PMCA or Protein Misfolding Cyclic Amplification: A method for amplifying PrP-res in a sample by mixing Prp-sen with the sample, incubating the reaction mix to permit PrP-res to initiate the conversion of PrP-sen to aggregates of PrP-res, fragmenting any aggregates formed during the incubation step (typically by sonication), and repeating one or more cycles of the incubation and fragmentation steps.

QUIC or Quaking Induced Conversion: A particular type of rPrP-sen amplification assay, in which shaking of the reaction vessels is performed instead of sonication to disrupted aggregated PrP-sen and PrP-res.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences. Methods for aligning sequences for comparison are described in detail below, in section IV E of the Detailed Description.

Single Round: Performing a method wherein serial amplification is not performed. For example, PrP-res can be amplified in a sample, by mixing the sample with purified rPrP-sen to make a reaction mix; performing an amplification reaction that includes (i) incubating the reaction mix to permit coaggregation of the rPrP-sen with the PrP-res that may be present in the reaction mix, and maintaining incubation conditions that promote coaggregation of the rPrP-sen with the PrP-res and results in a conversion of the rPrP-sen to rPrP-res$^{(Sc)}$ while inhibiting development of rPrP-res$^{(spon)}$; (ii) agitating aggregates formed during step (i); (iii) optionally repeating steps (i) and (ii) one or more times. rPrP-res$^{(Sc)}$ is detected in the reaction mix, wherein detection of rPrP-res$^{(Sc)}$ in the reaction mix indicates that PrP-res was present in the sample. However, a portion of the reaction mix is not removed and incubated with additional rPrP-sen.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999).

IV. Detailed Description of Particular Embodiments

A. Overview of Prions and Prion Disease

The transmissible spongiform encephalopathies (TSEs, or prion diseases) are infectious neurodegenerative diseases of mammals that include (but are not limited to) scrapie in sheep, bovine spongiform encephalopathy (BSE; also known as mad cow disease) in cattle, transmissible mink encephalopathy (TME) in mink, chronic wasting disease (CWD) in elk, moose, and deer, feline spongiform encephalopathy in cats, exotic ungulate encephalopathy (EUE) in nyala, oryx and greater kudu, and Creutzfeldt-Jakob disease (CJD) and its varieties (iatrogenic Creutzfeldt-Jakob disease (iCJD), variant Creutzfeldt-Jakob disease (vCJD), familial Creutzfeldt-Jakob disease (fCJD), and sporadic Creutzfeldt-Jakob disease (sCJD)), Gerstmann-Sträussler-Scheinker syndrome (GSS), fatal familial insomnia (fFI), sporadic fatal insomnia (sFI), kuru, and Alpers syndrome in humans. TSEs have incubation periods of months to years, but after the appearance of clinical signs often are rapidly progressive, untreatable, and invariably fatal. Attempts at TSE risk reduction have led to profound changes in the production and trade of agricultural goods, medicines, cosmetics, and biotechnology products.

In TSEs the pathological, protease-resistant form of prion protein, termed PrP$^{Sc}$ or PrP-res, appears to propagate itself in infected hosts by inducing the conversion of its normal host-encoded precursor, PrP-sen, into PrP$^{Sc}$. PrP-sen is a monomeric glycophosphatidylinositol-linked glycoprotein that is low in β-sheet content, and highly protease-sensitive. Conversely, PrP$^{Sc}$ aggregates are high in β-sheet content and partially protease-resistant. Mechanistic details of the conversion are not well understood, but involve direct interaction between PrP$^{Sc}$ and PrP-sen, resulting in conformational changes in PrP-sen as the latter is recruited into the growing PrP$^{Sc}$ multimer (reviewed in Caughey & Baron (2006) Nature 443, 803-810). Accordingly, the conversion mechanism has been tentatively described as autocatalytic seeded (or nucleated) polymerization.

To better understand the mechanism of prion propagation, many attempts to recapitulate PrP$^{Sc}$ formation in cell-free systems have been made. Initial experiments showed that PrP$^{Sc}$ can induce the conversion of PrP-sen to PrP$^{Sc}$ with strain- and species-specificities, albeit with substoichiometric yields. More recently, it was shown that PrP$^{Sc}$ formation and TSE infectivity can be amplified indefinitely in crude brain homogenates, a medium containing numerous potential cofactors for conversion (Castilla et al., (2005) Cell 121, 195-206). Dissection of this "protein misfolding cyclic amplification" (PMCA) reaction showed that PrP$^{Sc}$ and prion infectivity also could be amplified using PrP-sen purified from brain tissue as long as polyanions such as RNA were added (Deleault et al., (2007) Proc Natl Acad Sci USA. 104 (23):9741-6). Recombinant PrP-sen (rPrP-sen) from E. coli lacks glycosylation and the GPI anchor and prior to this disclosure has not been used successfully as an amplification substrate in PrP$^{Sc}$-seeded PMCA reactions. In fact, it was previously reported that rPrP-sen does not work in the PMCA system (Nishina et al., (2006) Biochemistry 45(47):14129-39). However, rPrP-sen can be converted to protease-resistant forms with limited yields when mixed with PrP$^{Sc}$. rPrP-sen also can be induced to polymerize into amyloid fibrils spontaneously or when seeded by preformed rPrP fibrils. Although most rPrP amyloid preparations are not infectious, synthetic amyloid fibrils of mutant recombinant prion protein can cause or accelerate TSE disease in transgenic mice that vastly overexpress the same mutant prion protein construct (Legname et al. (2004) Science 305, 673-676). However, these "synthetic prions" were non-infectious for wild type mice, making them at least 108-fold less infectious than bona fide PrP$^{Sc}$. Thus, the basic structure and propagation mechanism of robust TSE infectivity (or prions) remains to be fully ascertained.

A key challenge in coping with TSEs is the rapid detection of low levels of TSE infectivity (prions) by rapid methods. The most commonly used marker for TSE infections is PrP$^{Sc}$, and the PMCA reaction allows extremely sensitive detection of PrP$^{Sc}$ at levels below single infectious units in infected tissue. However, as previously noted, current limitations of PMCA include the time required to achieve optimal sensitivity (~3 weeks) and the use of brain PrP-sen as the amplification substrate.

B. Transmissible Spongiform Encephalopathies (TSEs)

The most common TSE in animals is scrapie, but the most famous and dangerous TSE is BSE, which affects cattle and is known by its lay term "mad cow disease." In humans, the most common TSE is CJD, which occurs worldwide with an incidence of 0.5 to 1.5 new cases per one million people each year. Three different forms of CJD have been traditionally recognized: sporadic (sCJD; 85% of cases), familial (fCJD; 10%), and iatrogenic (iCJD; 5%). However, in 1996, a new variant form of CJD (vCJD) emerged in the UK that was associated with consumption of meat infected with BSE. In contrast with typical sCJD, vCJD affects young patients with an average age of 27 years, and causes a relatively long illness (14 months compared with 4.5 months for sCJD). Because of insufficient information available about the incubation time and the levels of exposure to contaminated cattle food products, it is difficult to predict the future incidence of vCJD. In animals, there is no evidence for inherited forms of the disease, and most cases appear to be acquired by horizontal or vertical transmission.

The clinical diagnosis of sCJD is based on a combination of rapidly progressive multifocal dementia with pyramidal and extrapyramidal signs, myoclonus, and visual or cerebellar signs, associated with a characteristic periodic electroencephalogram (EEG). A key diagnostic feature of sCJD that distinguishes it from Alzheimer's disease and other dementias is the rapid progression of clinical symptoms and the short duration of the disease, which is often less than 2 years. The clinical manifestation of fCJD is very similar, except that the disease onset is slightly earlier than in sCJD. Family history of inherited CJD or genetic screening for mutations in the prion protein gene are used to establish fCJD diagnosis, although lack of family history does not excludes an inherited origin.

Variant CJD appears initially as a progressive neuropsychiatric disorder characterized by symptoms of anxiety, depression, apathy, withdrawal and delusions, combined with persistent painful sensory symptoms and followed by ataxia, myoclonus, and dementia. Variant CJD is differentiated from sCJD by the duration of illness (usually longer than 6 months) and EEG analysis (vCJD does not show the atypical pattern observed in sCJD). A high bilateral pulvinar signal noted during MRI is often used to help diagnose vCJD. In addition, a tonsil biopsy can be used to help diagnose vCJD, based on a number of cases of vCJD have been shown to test positive for PrPSc staining in lymphoid tissue (such as tonsil and appendix). However, because of the invasive nature of this test, it is performed only in patients who fulfill the clinical criteria of vCJD where the MRI of the brain does not show the characteristic pulvinar sign.

GSS is a dominantly inherited illness that is characterized by dementia, Parkinsonian symptoms, and a relatively long duration (typically, 5-8 years). Clinically, GSS is similar to Alzheimer's disease, except that is often accompanied by ataxia and seizures. Diagnosis is established by clinical examination and genetic screening for prion protein mutations. FFI is also dominantly inherited and associated with prion protein mutations. However, the major clinical finding associated with FFI is insomnia, followed at late stages by myoclonus, hallucinations, ataxia, and dementia.

C. Protein Misfolding Cyclic Amplification (PMCA), and rPrP-res Amplification (rPrP-PMCA and QUIC)

The prion detection method termed protein misfolding cyclic amplification (PMCA) is based on the ability of prions to replicate in vitro in tissue homogenates containing PrP-sen (see, for instance, WO0204954). PMCA involves amplification of a PrP-res through incubation with a suitable prion protein substrate derived from brain tissue, serial amplification of the PrP-res, for instance by alternating incubation and sonication steps, and detection of the resulting PrP-res$^{(Sc)}$. In some instances, incubation and sonication are alternated over a period of approximately three weeks, and intermittently a portion of the reaction mix is removed and incubated with additional PrP-sen in order to serially amplify the PrP-res in the sample. Following the repeated incubation/sonication/dilution steps, the resulting PrP-res$^{(Sc)}$ is detected in the reaction mix. Although PMCA is a very sensitive assay for detecting PrP-res, it has a number of limitations, notably the time required to achieve optimal sensitivity (~3 weeks) and the requirement for brain-derived PrP-sen as the amplification substrate.

The development of more sensitive, rapid, and practical means for detection of PrP$^{Sc}$ and TSE infectivity is critical in addressing the challenges posed by prion diseases. Such a test could be used to identify sources of TSE infection in agriculture and the environment to reduce risks to humans and animals. Moreover, the ability to diagnose infections in humans long before the appearance of clinical signs would greatly improve the chances of treating these otherwise fatal diseases. Indeed, drug treatments in animals tend to be much more effective when treatments are initiated within the first two thirds of the incubation period Caughey et al. (2006) *Accts. Chem. Res.* 39, 646-653; Trevitt & Collinge (2006) *Brain* 129, 2241-2265).

Disclosed herein is an improved prion assay, termed rPrP-res amplification assay (including rPrP-PMCA and QUIC), that differs from the PMCA PrP$^{Sc}$ amplification method (Saa et al., (2006) *J. Biol. Chem.* 281, 35245-35252; Saa et al., (2006) *Science* 313, 92-94). rPrP-PMCA greatly improves the practicality of the basic PMCA approach in several significant ways. First, instead of prion protein substrate derived from brain tissue, rPrP-PMCA and QUIC (when agitation is performed by shaking) makes use of bacterially-expressed rPrP-sen as a substrate, which can be obtained rapidly in high purity and in large amounts, whereas purification of PrP-sen from brain tissue is difficult and gives much lower yields (Deleault et al. (2005) *J. Biol. Chem.* 280, 26873-26879; Pan et al. (1993) *Proc. Natl. Acad. Sci. USA* 90, 10962-10966; Hornemann et al., (2004) EMBO Rep. 5, 1159-1164). Furthermore, unlike PrP-sen in brain homogenates or purified from brain, rPrP-sen can be easily mutated or strategically labeled with probes to simplify and accelerate the detection of relevant rPrP-PMCA products.

There are two types of rPrP-res amplification methods that utilize rPrP-sen, one that uses sonication (rPrP-PMCA) and one that utilizes shaking (QUIC). These methods facilitate fundamental studies of the structure and conversion mechanism of PrP$^{Sc}$. Site-directed mutations can allow precise labeling of rPrP-sen with a variety of probes that can report on conformational changes, and both inter-molecular and intra-molecular distances within rPrP-res aggregates.

The rPrP-PMCA and QUIC methods generally involve mixing a sample (for example a tissue sample or CSF sample that is suspected of containing PrP-res) with purified rPrP-sen to make a reaction mix, and performing a primary reaction to form and amplify specific forms of rPrP-res in the mixture. This primary reaction includes incubating the reaction mix to permit the PrP-res to initiate the conversion of rPrP-sen to specific aggregates or polymers of rPrP-res; fragmenting any aggregates or polymers formed during the incubation step; and repeating the incubation and fragmentation steps one or more times, for instance from about 10 to about 50 times. In some embodiments of the method, serial amplification is carried out by removing a portion of the reaction mix and incubating it with additional rPrP-sen. Following amplification, the prion-initiated rPrP-res$^{(Sc)}$ in the reaction mix is detected, for example using an antibody. In some examples, the reaction mix is digested with proteinase K (which digests the remaining rPrP-sen in the reaction mix) prior to detection of the rPrP-res$^{(Sc)}$. Two types of mis-folded prion protein can be generated in rPrP-PMCA (or QUIC) reactions, one occurring spontaneously (rPrP-res$^{(spon)}$) and the other initiated by the presence of prions (rPrP-res$^{(Sc)}$) in the test sample. Thus, it is often necessary to discriminate between the former and the latter to interpret the rPrP-PMCA assay. For instance, this can be done on the basis of differing protein fragment sizes generated upon exposure to proteinase K. An unexpectedly superior decrease in the amount of rPrP-res$^{(spon)}$) formed is achieved with the QUIC assay.

The use of recombinant prion protein as a substrate for the QUIC reaction instead of PrP-sen contained in, or isolated from, brain homogenates (which is the source of substrate in conventional PMCA) confers several advantages. For instance, successful expression and folding of rPrP enables the generation of large amounts of highly purified and concentrated substrate, which is not possible when the only available source of substrate is brain tissue. Additionally and surprisingly, the use of concentrated recombinant prion protein promotes far faster amplification reactions than does PrP-sen in brain homogenate. It is this surprising functionality of the rPrP that reduces the time required for the reaction from up to three weeks to about 1-2 days, or even less than a day.

All of the methods disclosed herein, such as QUIC, will work under a variety of conditions. In several embodiments, optimal conditions that support specific PrP$^{Sc}$-seeded QUIC include the use of a detergent, such as both an ionic and a non-ionic detergent. The conditions can include the combination of about 0.05-0.1% of an ionic detergent such as SDS and about 0.05-0.1% of a nonionic detergent such as TX-100 in the reaction mix. Other preferred conditions include the use of shaking instead of sonication (the so-called QUIC reaction), and the use of cycles of shaking/rest that are about 1:1 in duration. Reactions have also been found to be particularly efficient at 37-60° C., for example 45-55° C. These conditions are particularly effective at promoting the formation of rPrP-res$^{(Sc)}$ (notably the 17 kDa PK-resistant species), while reducing rPrP-res$^{(spon)}$ formation within the first 24 hours of unseeded reactions. However, longer amplification reactions of more than 24 hours, such as at least 45 hours or even 65 or 96 hours, can also provide excellent results.

The sensitivity of the assay has been found to be degraded (and potential false positive results are obtained) by the production of rPrP-res$^{(spon)}$ in the use of rPrP-sen seeded reactions. To help avoid this problem, conditions are selected to inhibit the formation of the rPrP-res$^{(spon)}$ byproduct. In some examples, assays (such as QUIC) are performed to test assay conditions to determine if the assay conditions increase or decrease rPrP-res$^{(spon)}$ byproduct formation, and assay conditions are selected that minimize the byproduct formation. The recognition of this previously unappreciated obstacle to the use of amplification assays has also helped provide a much faster and more sensitive assay to address this substantial public health concern.

The sensitivity achieved with rPrP-PMCA (and QUIC) is of considerable utility because it is very sensitive. For example, the assay allows consistent detection of HaPrP$^{Sc}$ levels (50 ag) that are >100-fold lower than those typically associated with a lethal intracerebral dose of 263K strain scrapie infectivity in Syrian golden hamsters. Although this detection limit is not quite as low as that reported for the conventional PMCA (1.2 ag PrP$^{Sc}$; Saa et al., (2006) *J. Biol. Chem.* 281, 35245-35252), it can be achieved in two rPrP-PMCA rounds of amplification over a total of about two days, whereas conventional PMCA requires seven rounds over a total of about 21 days (Saa et al., (2006) J. Biol. Chem. 281, 35245-35252). A single 50-hour round of conventional PMCA takes about the same time as two rounds of rPrP-PMCA, but has a 32,000-fold higher detection limit (1.6 pg; Saa et al., (2006) *J. Biol. Chem.* 281, 35245-35252). Without being bound by theory, it is believed that the more rapid rPrP-PMCA reaction is facilitated in-part by the higher concentration of rPrP-sen relative to that of PrP-sen in brain homogenates.

It has also been found that the rPrP-PMCA/QUIC assay can perform cross-species amplification of target PrP-res. In fact, rHaPrP-PMCA/QUIC provides a particularly suitable form of rPrP-res that promotes formation of PrP aggregates when incubated with a sample that contains PrP-res. rHaPrP appears to have a structure that promotes the formation of these aggregates with minimal formation of rPrP-res$^{(spon)}$ byproduct. Hence rHaPrP can be used to amplify target PrP in a sample taken from a species other than a hamster, such as a sample taken from a human, sheep, cow or cervid.

Another advantage of the rPrP-PMCA and QUIC assays is the ability to discriminate between scrapie-infected and uninfected hamsters using 2-μl CSF samples (see FIG. 4). Because CSF is more accessible in live individuals than is brain tissue, it is an attractive biopsy specimen for rPrP-PMCA- and QUIC-based diagnostic tests.

D. Recombinant Prion Protein

As described herein, the PrP-sen in used in rPrP-res PMCA reaction is recombinant prion protein, for example prion protein from cells engineered to over express the protein. Any prion protein sequence can be used to generate the rPrP-sen, for instance: *Xenopus laevis* (Genbank Accession No: NP001082180), *Bos Taurus* (Genbank Accession No: CAA39368), *Danio verio* (Genbank Accession No: NP991149), *Tragelaphus strepsiceros* (Genbank Accession No: CAA52781), *Ovis aries* (Genbank Accession No: CAA04236), *Trachemys scripta* (Genbank Accession No: CAB81568), *Gallus gallus* (Genbank Accession No: AAC28970), *Rattus norvegicus* NP036763), *Mus musculus* (Genbank Accession No: NP035300), *Monodelphis domestica* (Genbank Accession No: NP001035117), *Homo sapiens* (Genbank Accession No: BAA00011), *Giraffa camelopardalis* (Genbank Accession No: AAD13290), *Oryctolagus cuniculus* (Genbank Accession No: NP001075490), *Macaca mulatta* (Genbank Accession No: NP001040617), *Bubalus bubalus* (Genbank Accession No: AAV30514), *Tragelaphus imberbis* (Genbank Accession No: AAV30511), *Boselaphus tragocamelus* (Genbank Accession No: AAV30507), *Bos garus* (Genbank Accession No: AAV 30505), *Bison bison* (Genbank Accession No: AAV30503), *Bos javanicus* (Genbank Accession No: AAV30498), *Syncerus caffer caffer* (Genbank Accession No: AAV30492), *Syncerus caffer nanus* (Genbank Accession No: AAV30491), and *Bos indicus* (Genbank Accession No: AAV30489). In some embodiments, only a partial prion protein sequence is expressed as rPrP-sen. For instance, in certain examples rPrP-sen includes amino acids 23-231 (SEQ ID NOS: 1, 2) of the hamster (SEQ ID NO: 8) or mouse (SEQ ID NO: 9) prion protein sequences, or the corresponding amino acids of other prion protein sequences, for instance amino acids 23-231 (SEQ ID NO: 3) of human (129M) prion protein (SEQ ID NO: 10), amino acids 23-231 (SEQ ID NO: 4) of human (129V) prion protein (SEQ ID NO: 11), amino acids 25-241 (SEQ ID NO: 5) of bovine (6-octarepeat) prion protein, amino acids 25-233 (SEQ ID NO: 6) of ovine (136A 154R 171Q) prion protein, or amino acids 25-234 (SEQ ID NO: 7) of deer (96G 132M 138S) prion protein. In general, the partial prion protein sequence expressed as rPrP-sen corresponds to the polypeptide sequences of the natural mature full-length PrP$^C$ molecule, meaning that the rPrP-sen polypeptide lacks both the amino-terminal signal sequence and carboxy-terminal glycophosphatidylinositol-anchor attachment sequence. In another example, amino acids 30-231, 40-231, 50-231, 60-231, 70-231, 80-231, or 90-231 of any one of human, human 129V, bovine, ovine, or deer are utilized in the assays described herein. One of skill in the art can readily produces these polypeptides using the sequence information provided in SEQ ID NOs: 1-11, or using information available in GEN-BANK® (as available on Jul. 20, 2007).

The rPrP-sen can be a chimeric rPrP-sen, wherein a portion of the protein is from one species, and a portion of the protein is from another species, can also be utilized. In one example about 10 to about 90%, such as about 10%, about 20%, about 30%, about 40%, about 50%, about 60%, about 70% about 80% or about 90% of the rPrP-sen is from one species, and, correspondingly, about 90%, about 80%, about 70%, about 60%, about 50%, about 40%, about 30%, about 20% or about 10% is from another species. Chimeric proteins can include, for example, hamster rPrP-sen and rPrP-sen from another species, such as human PrP-sen.

In some embodiments, host cells are transformed with a nucleic acid vector that expresses the rPrP-sen, for example human, cow, sheep or hamster rPrP-sen. These cells can be mammalian cells, bacterial cells, yeast cells, insect cells, whole organisms, such as transgenic mice, or other cells that can serve as source of the PrP-sen. In particular examples the cell is a bacterial cell, such as an *E. coli* cell. Raw cell lysates or purified rPrP-sen from rPrP-sen expressing cells can be used as the source of the non-pathogenic protein.

In some embodiments the recombinant protein is fused with an additional amino acid sequence. For example, over expressed protein can be tagged for purification or to facilitate detection of the protein in a sample. Some possible fusion proteins that can be generated include histidine tags, Glutathione S-transferase (GST), Maltose binding protein (MBP), green fluorescent protein (GFP), and Flag and myc-tagged rPrP. These additional sequences can be used to aid in purification and/or detection of the recombinant protein, and in some cases are subsequently removed by protease cleavage. For example, coding sequence for a specific protease cleavage site can be inserted between the PrP-sen coding sequence and the purification tag coding sequence. One example for such a sequence is the cleavage site for thrombin. Thus, fusion proteins can be cleaved with the protease to free the PrP-sen from the purification tag.

Any of the wide variety of vectors known to those of skill in the art can be used to over-express rPrP-sen. For example, plasmids or viral vectors can be used. These vectors can be introduced into cells by a variety of methods including, but not limited to, transfection (for instance, by liposome, calcium phosphate, electroporation, particle bombardment, and the like), transformation, and viral transduction.

Recombinant PrP-sen also can include proteins that have amino sequences containing substitutions, insertions, deletions, and stop codons as compared to wild type sequences. In certain embodiment, a protease cleavage sequence is added to allow inactivation of protein after it is converted into prion form. For example, cleavage sequences recognized by Thrombin, Tobacco Etch Virus (Life Technologies, Gaithersburg, Md.) or Factor Xa (New England Biolabs, Beverley, Mass.) proteases can be inserted into the sequence. In some embodiments, inactivation of protein after it is converted into prion form is unnecessary because the rPrP-res$^{(Sc)}$ resulting from the reaction has little or no infectivity.

Changes also can be made in the pPrP-sen protein coding sequence, for example in the coding sequence for mouse, human, bovine, sheep, goat, deer and/or elk prion protein (GENBANK® accession numbers NM_011170, NM_183079, AY335912, AY723289, AY723292, AF156185 and AY748455, respectively, all of which are incorporated herein by reference, Jul. 20, 2007). For example, mutations can be made to match a variety of mutations and polymorphisms known for various mammalian prion protein genes (see, for instance, Table 1). Furthermore, chimeric PrP molecules comprising sequences from two or more different natural PrP sequences (for instance from different host species or strains) can be expressed from vectors with recombinant PrP gene sequences, and such chimeras can be used for rPrP-PMCA and QUIC detection of prion from various species. Cells expressing these altered prion protein genes can be used as a source of the rPrP-sen, and these cells can include cells that endogenously express the mutant rPrP gene, or cells that have been made to express a mutant rPrP protein by the introduction of an expression vector. Use of a mutated rPrP-sen can be advantageous, because some of these proteins are more easily or specifically converted to protease-resistant forms, and thus can further enhance the sensitivity of the method.

In certain embodiments, cysteine residues are placed at positions 94 and 95 of the hamster prion protein sequence in order to be able to selectively label the rPrP at those sites using sulfhydryl-reactive labels, such as pyrene and fluorescein linked to maleimide-based functional groups. In certain embodiments, these tags do not interfere with conversion but allow much more rapid, fluorescence-based detection of the rPrP-PMCA reaction product. In one example, pyrenes in adjacent molecules of rPrP-res are held in close enough proximity to allow eximer formation, which shifts the fluorescence emission spectrum in a distinct and detectable manner. Free pyrenes released from, or on, unconverted rPrP-sen molecules are unlikely to form eximer pairs. Thus, the rPrP-PMCA reaction can be run in a multiwell plate, digested with proteinase K, and then eximer fluorescence can be measured to rapidly test for the presence of rPrP-res$^{(Sc)}$. Sites 94 and 95 were chosen for the labels because the PK-resistance in this region of PrP-res distinguishes rPrP-res$^{(Sc)}$ from rPrP-res$^{(spon)}$, giving rise to the 17 kDa rPrP-res band. Other positions in the PK-resistant region(s) that distinguish the 17-kDa rHaPrP-res$^{(Sc)}$ fragment from all rHaPrP-res$^{(spon)}$ fragments also can work for this purpose.

TABLE 1

| Pathogenic human mutations | Human polymorphisms | Ovine polymorphisms | Bovine polymorphisms |
|---|---|---|---|
| 2 octarepeat insert | Codon 129 Met/Val | Codon 171 Arg/Glu | 5 or 6 octarepeats |
| 4-9 octarepeat insert | Codon 219 Glu/Lys | Codon 136 Ala/Val | |
| Codon 102 Pro-Leu | | | |
| Codon 105 Pro-Leu | | | |
| Codon 117 Ala-Val | | | |
| Codon 145 Stop | | | |
| Codon 178 Asp-A | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

E. Variant Prion Protein Sequences

As any molecular biology textbook teaches, a peptide of interest is encoded by its corresponding nucleic acid sequence (for instance, an mRNA or genomic DNA). Accordingly, nucleic acid sequences encoding prion proteins are contemplated herein, at least, to make and use the prion proteins of the disclosed compositions and methods.

In one example, in vitro nucleic acid amplification (such as polymerase chain reaction (PCR)) can be utilized as a method for producing nucleic acid sequences encoding prion proteins. PCR is a standard technique that is described, for instance, in *PCR Protocols: A Guide to Methods and Appli-* cations (Innis et al., San Diego, Calif.: Academic Press, 1990), or *PCR Protocols, Second Edition* (*Methods in Molecular Biology*, Vol. 22, ed. by Bartlett and Stirling, Humana Press, 2003).

A representative technique for producing a nucleic acid sequence encoding a prion protein by PCR involves preparing a sample containing a target nucleic acid molecule that includes the prion protein-encoding sequence. For example, DNA or RNA (such as mRNA or total RNA) can serve as a suitable target nucleic acid molecule for PCR reactions. Optionally, the target nucleic acid molecule can be extracted from cells by any one of a variety of methods well known to those of ordinary skill in the art (for instance, Sambrook et al., *Molecular Cloning: A Laboratory Manual*, Cold Spring Harbor Laboratory Press, New York, 1989; Ausubel et al., *Current Protocols in Molecular Biology*, Greene Publ. Assoc. and Wiley-Intersciences, 1992). Prion proteins are expressed in a variety of mammalian cells. In examples where RNA is the initial target, the RNA is reverse transcribed (using one of a myriad of reverse transcriptases commonly known in the art) to produce a double-stranded template molecule for subsequent amplification. This particular method is known as reverse transcriptase (RT)-PCR. Representative methods and conditions for RT-PCR are described, for example, in Kawasaki et al. (In *PCR Protocols, A Guide to Methods and Applications*, Innis et al. (eds.), 21-27, Academic Press, Inc., San Diego, Calif., 1990).

The selection of amplification primers will be made according to the portion(s) of the target nucleic acid molecule that is to be amplified. In various embodiments, primers (typically, at least 10 consecutive nucleotides of prion-encoding nucleic acid sequence) can be chosen to amplify all or part of a prion-encoding sequence. Variations in amplification conditions may be required to accommodate primers and amplicons of differing lengths and composition; such considerations are well known in the art and are discussed for instance in Innis et al. (PCR Protocols, A Guide to Methods and Applications, San Diego, Calif.: Academic Press, 1990). From a provided prion protein-encoding nucleic acid sequence, one skilled in the art can easily design many different primers that can successfully amplify all or part of a prion protein-encoding sequence.

As described herein, a number of prion protein-encoding nucleic acid sequences are known. Though particular nucleic acid sequences are disclosed, one of skill in the art will appreciate that also provided are many related sequences with the functions described herein, for instance, nucleic acid molecules encoding conservative variants of a prion protein. One indication that two nucleic acid molecules are closely related (for instance, are variants of one another) is sequence identity, a measure of similarity between two nucleic acid sequences or between two amino acid sequences expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=-3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 50%, at least 60%, at least 70%, at least 80%, at least 85%, at least 90%, at least 95%, at least 98%, or at least 99% sequence identity to the sequence of interest.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, r at least 98%, or at least 99% sequence identity to the prion sequence of interest.

Another indication of sequence identity is nucleic acid hybridization. In certain embodiments, prion protein-encoding nucleic acid variants hybridize to a disclosed (or otherwise known) prion protein-encoding nucleic acid sequence, for example, under low stringency, high stringency, or very high stringency conditions. Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, although wash times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

The following are representative hybridization conditions and are not meant to be limiting.

| Very High Stringency (detects sequences that share at least 90% sequence identity) | |
| --- | --- |
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share at least 80% sequence identity) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share at least 50% sequence identity) | |
| Hybridization: | 6x SSC at RT to 55° C. for 16-20 hours |
| Wash at least twice: | 2x-3x SSC at RT to 55° C. for 20-30 minutes each. |

F. Prion Proteins

This disclosure further provides compositions and methods involving wild type and recombinant prion proteins. In some embodiments, prion protein variants include the substitution of one or several amino acids for amino acids having similar biochemical properties (so-called conservative substitutions). Conservative amino acid substitutions are likely to have minimal impact on the activity of the resultant protein, such as it's ability to convert PrP-sen to PrP-res. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. In some examples, prion protein variants can have no more than 3, 5, 10, 15, 20, 25, 30, 40, or 50 conservative amino acid changes. The following table shows exemplary conservative amino acid substitutions that can be made to a prion protein, for instance the recombinant prion proteins shown in SEQ ID NOs: 1-7.

TABLE 2

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

G. Purification of Recombinant Prion Protein

To purify PrP-sen from recombinant (or natural) sources, the composition is subjected to fractionation to remove various other components from the composition. Various techniques suitable for use in protein purification are well known. These include, for example, precipitation with ammonium sulfate, PTA, PEG, antibodies and the like, or by heat denaturation followed by centrifugation; chromatography steps such as metal chelate, ion exchange, gel filtration, reverse phase, hydroxylapatite, lectin affinity, and other affinity chromatography steps; isoelectric focusing; gel electrophoresis; and combinations of such and other techniques.

H. Sources of Samples for rPrP-res Amplification Assays, Such as rPrP-PMCA and QUIC Assays The samples analyzed using the methods described herein can include any composition capable of being contaminated with a prion. Such compositions can include tissue samples or bodily fluids including, but not limited to, blood, lymph nodes, brain, spinal cord, tonsils, spleen, skin, muscles, appendix, olfactory epithelium, cerebral spinal fluid, urine, feces, milk, intestines, tears and/or saliva. Other compositions from which samples can be taken for analysis, for instance, include food stuffs, drinking water, forensic evidence, surgical implements, and/or mechanical devices.

I. Methods for Detecting rPrP-res$^{(Sc)}$ in rPrP-res Amplification Mixes, Such as rPrP-PMCA and QUIC Reaction Mixes Once rPrP-res$^{(Sc)}$ has been generated using rPrP-res amplification, such as using rPrP-PMCA (such as the QUIC assay), rPrP-res$^{(Sc)}$ can be detected in the reaction mix. Direct and indirect methods can be used for detection of rPrP-res$^{(Sc)}$ in a reaction mix or serial reaction mix. For methods in which rPrP-res$^{(Sc)}$ is directly detected, separation of newly-formed rPrP-res$^{(Sc)}$ from remaining rPrP-sen usually is required. This typically is accomplished based on the different natures of rPrP-res$^{(Sc)}$ versus rPrP-sen. For instance, rPrP-res$^{(Sc)}$ typically is highly insoluble and resistant to protease treatment. Therefore, in the case of rPrP-res$^{(Sc)}$ and rPrP-sen, separation can be by, for instance, protease treatment.

When rPrP-res$^{(Sc)}$ and rPrP-sen are separated by protease treatment, reaction mixtures are incubated with, for example, Proteinase K (PK). An exemplary protease treatment includes digestion of the protein, for instance, rPrP-sen, in the reaction mixture with 1-20 µg/ml of PK for about 1 hour at 37° C. Reactions with PK can be stopped prior to assessment of prion levels by addition of PMSF or electrophoresis sample buffer. Depending on the nature of the sample, incubation at 37° C. with 1-50 µg/ml of PK generally is sufficient to remove rPrP-sen.

rPrP-res$^{(Sc)}$ also can be separated from the rPrP-sen by the use of ligands that specifically bind and precipitate the misfolded form of the protein, including conformational antibodies, certain nucleic acids, plasminogen, PTA and/or various peptide fragments.

1. Western Blot

In some examples, reaction mixtures fractioned or treated with protease to remove rPrP-sen are then subjected to Western blot for detection of rPrP-res$^{(Sc)}$ and the discrimination of rHaPrP-res$^{(Sc)}$ from rHaPrP-res$^{(spon)}$. Typical Western blot procedures begin with fractionating proteins by sodium dodecyl sulfate-polyacrylamide gel electrophoresis (SDS-PAGE) under reducing conditions. The proteins are then electroblotted onto a membrane, such as nitrocellulose or PVDF and probed, under conditions effective to allow immune complex (antigen/antibody) formation, with an anti-prion protein antibody. Exemplary antibodies for detection of prion protein include the 3F4 monoclonal antibody, monoclonal antibody D13 (directed against residues 96-106 (Peretz et al. (2001) *Nature* 412, 739-743)), polyclonal antibodies R18 (directed against residues 142-154), and R20 (directed against C-terminal residues 218-232) (Caughey et al. (1991) *J. Virol.* 65, 6597-6603).

Following complex formation, the membrane is washed to remove non-complexed material. An exemplary washing procedure includes washing with a solution such as PBS/Tween, or borate buffer. The immunoreactive bands are visualized by a variety of assays known to those in the art. For example, the enhanced chemoluminesence assay (Amersham, Piscataway, N.J.) can be used.

If desired, prion protein concentration can be estimated by Western blot followed by densitometric analysis, and comparison to Western blots of samples for which the concentration of prion protein is known. For example, this can be accomplished by scanning data into a computer followed by analysis with quantitation software. To obtain a reliable and robust quantification, several different dilutions of the sample generally are analyzed in the same gel.

2. ELISA, Immunochromatographic Strip Assay, and Conformation Dependent Immunoassay As described above, immunoassays in their most simple and direct sense are binding assays. Specific non-limiting immunoassays of use include various types of enzyme linked immunosorbent assays (ELISAs), immunochromatographic strip assays, radioimmunoassays (RIA), and specifically conformation-dependent immunoassays.

In one exemplary ELISA, anti-PrP antibodies are immobilized onto a selected surface exhibiting protein affinity, such as a well in a polystyrene microtiter plate. Then, a reaction mixture suspected of containing prion protein antigen is added to the wells. After binding and washing to remove non-specifically bound immune complexes, the bound prion protein can be detected. Detection generally is achieved by the addition of another anti-PrP antibody that is linked to a detectable label. This type of ELISA is a simple "sandwich ELISA." Detection also can be achieved by the addition of a second anti-PrP antibody, followed by the addition of a third antibody that has binding affinity for the second antibody, with the third antibody being linked to a detectable label.

In another exemplary ELISA, the reaction mixture suspected of containing the prion protein antigen is immobilized onto the well surface and then contacted with the anti-PrP antibodies. After binding and washing to remove non-specifically bound immune complexes, the bound anti-prion antibodies are detected. Where the initial anti-PrP antibodies are linked to a detectable label, the immune complexes can be detected directly. Again, the immune complexes can be detected using a second antibody that has binding affinity for the first anti-PrP antibody, with the second antibody being linked to a detectable label.

Another ELISA in which protein of the reaction mix is immobilized involves the use of antibody competition in the detection. In this ELISA, labeled antibodies against prion protein are added to the wells, allowed to bind, and detected by means of their label. The amount of prion protein antigen in a given reaction mix is then determined by mixing it with the labeled antibodies against prion before or during incubation with coated wells. The presence of prion protein in the sample acts to reduce the amount of antibody against prion available for binding to the well and thus reduces the ultimate signal. Thus, the amount of prion in the sample can be quantified.

Irrespective of the format employed, ELISAs have certain features in common, such as coating, incubating or binding, washing to remove non-specifically bound species, and detecting the bound immune complexes. These are described below.

In coating a plate with either antigen or antibody, one generally incubates the wells of the plate with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antibodies. These include bovine serum albumin, casein, and solutions of milk powder. The coating allows for blocking of nonspecific adsorption sites on the immobilizing surface, and thus reduces the background caused by nonspecific binding of antibodies onto the surface.

It is customary to use a secondary or tertiary detection means rather than a direct procedure with ELISAs, though this is not always the case. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin, milk proteins, and phosphate buffered saline (PBS)/Tween. These added agents also tend to assist in the reduction of nonspecific background. "Suitable" conditions also mean that the incubation is at a temperature and for a period of time sufficient to allow effective binding. Incubation steps are typically from about 1 to 2 to 4 hours, at temperatures preferably on the order of 25° C. to 27° C., or can be overnight at about 4° C. or so.

Following all incubation steps in an ELISA, the contacted surface is washed so as to remove non-complexed material. An exemplary washing procedure includes washing with a solution such as PBS/Tween or borate buffer. Following the formation of specific immune complexes between the test sample and the originally bound material, and subsequent washing, the occurrence of even minute amounts of immune complexes can be determined.

To provide a detecting means, the second or third antibody generally will have an associated label to allow detection. In some examples, this is an enzyme that will generate color development upon incubating with an appropriate chromogenic substrate. Thus, for example, the first or second immune complex is contacted and incubated with a urease, glucose oxidase, alkaline phosphatase or hydrogen peroxidase-conjugated antibody for a period of time and under conditions that favor the development of further immune complex formation (for instance, incubation for two hours at room temperature in a PBS-containing solution such as PBS-Tween).

After incubation with the labeled antibody, and subsequent to washing to remove unbound material, the amount of label is quantified, for instance, by incubation with a chromogenic substrate such as urea and bromocresol purple or 2,2'-azino-di-(3-ethyl-benzthiazoline-6-sulfonic acid) and $H_2O_2$, in the case of peroxidase as the enzyme label. Quantification is then achieved by measuring the degree of color generation, for instance, using a visible spectra spectrophotometer.

J. rPrP-sen Labeling

In certain embodiments, the recombinant PrP-sen substrate protein can be labeled to enable high sensitivity of detection of protein that is converted into rPrP-res$^{(Sc)}$. For example, rPrP-sen can be radioactively labeled, epitope tagged, or fluorescently labeled. The label can be detected directly or indirectly. Radioactive labels include, but are not limited to $^{125}$I, $^{32}$P, $^{33}$P, and $^{35}$S.

The mixture containing the labeled protein is subjected to an rPrP-Res amplification assay, such as rPrP-PMCA or QUIC, and the product detected with high sensitivity by following conversion of the labeled protein after removal of the unconverted protein for example by proteolysis. Alternatively, the protein can be labeled in such a way that a signal can be detected upon the conformational changes induced during conversion. An example of this is the use of FRET technology, in which the protein is labeled by two appropriate fluorophores, which upon refolding become close enough to exchange fluorescence energy (see for example U.S. Pat. No. 6,855,503).

In certain embodiments, cysteine residues are placed at positions 94 and 95 of the hamster prion protein sequence in order to be able to selectively label the rPrP-sen at those sites using sulfhydryl-reactive labels, such as pyrene and fluorescein linked to maleimide-based functional groups. In certain embodiments, these tags do not interfere with conversion but allow much more rapid, fluorescence-based detection of the rPrP-PMCA reaction product. In one example, pyrenes in adjacent molecules of rPrP-res are held in close enough proximity to allow eximer formation, which shifts the fluorescence emission spectrum in a distinct and detectable manner. Free pyrenes released from, or on, unconverted rPrP-sen molecules are unlikely to form eximer pairs. Thus, the rPrP-Res amplification reaction can be run in a multiwell plate, digested with proteinase K, and then eximer fluorescence can be measured to rapidly test for the presence of rPrP-res$^{(Sc)}$. Sites 94 and 95 are chosen for the labels because the PK-resistance in this region of PrP-res distinguishes rPrP-res$^{(Sc)}$ from rPrP-res$^{(spon)}$, giving rise to the 17 kDa rPrP-res band. Other positions in the PK-resistant region(s) that distinguish the 17-kDa rHaPrP-res$^{(Sc)}$ fragment from all rHaPrP-res$^{(spon)}$ fragments also can work for this purpose.

In certain other embodiments, the use of a fluorescently-tagged rPrP-sen substrate for the reaction is combined with the use an immunochromatographic strip test with an immobilized rPrP-res specific antibody (for example, from Prionics AG, Schlieren-Zurich, Switzerland). Binding of the rPrP-res to the antibody is then detected with a fluorescence detector.

K. Antibody Generation

In certain embodiments, the present disclosure involves antibodies, such as antibodies that recognize PrP proteins. For example, antibodies are used in many of the methods for detecting prions (for instance, Western blot and ELISA). In addition to antibodies generated against full length proteins, antibodies also can be generated in response to smaller constructs comprising epitopic core regions, including wild-type and mutant epitopes.

As used herein, the term "antibody" is intended to refer broadly to any immunologic binding agent such as IgG, IgM, IgA, IgD and IgE. Generally, IgG and/or IgM are used because they are the most common antibodies in the physiological situation and because they are most easily made in a laboratory setting. Monoclonal antibodies are recognized to have certain advantages, for instance reproducibility and large-scale production. The monoclonal antibodies can be of human, murine, monkey, rat, hamster, rabbit and even chicken origin.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known. Means for preparing and characterizing antibodies are also well known.

mAbs can be prepared through use of well-known techniques, such as those exemplified in U.S. Pat. No. 4,196,265. mAbs can be further purified, if desired, using filtration, centrifugation and various chromatographic methods such as HPLC or affinity chromatography. Fragments of the monoclonal antibodies of the disclosure can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer. It also is contemplated that a molecular cloning approach can be used to generate mAbs.

L. Screening for Modulators of Prion Function

The disclosed assay also can be used to identify compounds that modify the ability of prions to replicate, such as compounds that would be candidates for the treatment of prion diseases. Thus, the method for screening compounds includes performing an rPrP-Res amplification assay on control reaction mixtures, and reaction mixtures including the test compound are accessed for levels of rPrP-res$^{(Sc)}$ following amplification. When a difference between the levels of rPrP-res$^{(Sc)}$ in the test versus control reaction mixtures is detected, compounds could be identified that either enhance or inhibit conversion of rPrP-sen to rPrP-res$^{(Sc)}$. These assays can include random screening of large libraries of candidate substances; alternatively, the assays can be used to focus on particular classes of compounds selected with an eye towards structural attributes that are believed to make them more likely to modulate the function of prions.

By function, it is meant that one can determine the efficiency of conversion by assaying conversion of a standard amount of rPrP-sen into rPrP-res$^{(Sc)}$ by a known amount of prion. This can be determined by, for instance, quantitating the amount of rPrP-res$^{(Sc)}$ in a reaction mix following a certain number of cycles of rPrP-PMCA or QUIC.

As used herein, the term "candidate substance" refers to any molecule that potentially can inhibit or enhance prion function activity. The candidate substance can be a protein or fragment thereof, a small molecule, a polymer or even a nucleic acid molecule. The most useful pharmacological compounds can be compounds that are structurally related to prion protein or prion protein ligands. Using lead compounds to help develop improved compounds is known as "rational drug design," and includes not only comparisons with known inhibitors and activators, but predictions relating to the structure of target molecules. The goal of rational drug design is to produce structural analogs of biologically active polypeptides or target compounds. By creating such analogs, it is possible to fashion drugs that are more active or stable than the natural molecules, and that have different susceptibility to alteration or which can affect the function of various other molecules. In one approach, one generates a three-dimensional structure for a target molecule, or a fragment thereof, for instance by x-ray crystallography, computer modeling, or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of an anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes can be generated using the methods described herein for producing antibodies, using an antibody as the antigen.

Alternatively, small molecule libraries can be acquired that are believed to meet the basic criteria for useful drugs in an effort to identify useful compounds by large-scale screening. Screening of such libraries, including combinatorially generated libraries (for instance, peptide libraries), is a rapid and efficient way to screen large number of related (and unrelated) compounds for activity. Combinatorial approaches also lend themselves to rapid evolution of potential drugs by the creation of second, third and fourth generation compounds modeled on active, but otherwise undesirable compounds.

Candidate compounds can include fragments or parts of naturally-occurring compounds, or can be found as active combinations of known compounds, which are otherwise inactive. Compounds isolated from natural sources, such as animals, bacteria, fungi, plant sources, including leaves and bark, and marine samples, can be assayed as candidates for the presence of potentially useful pharmaceutical agents. It will be understood that the pharmaceutical agents to be screened also could be derived or synthesized from chemical compositions or man-made compounds. Thus, it is understood that the candidate substance identified by the present disclosure can be peptide, polypeptide, polynucleotide, glycans, synthetic polymers, small molecule inhibitors or any other compound(s) that can be designed through rational drug design starting from known inhibitors or stimulators. Other suitable modulators include antibodies (including single chain antibodies), each of which would be specific for the target molecule. Such compounds are described in greater detail above.

In addition to the modulating compounds initially identified, other sterically similar compounds can be formulated to mimic the key portions of the structure of the modulators. Such compounds, which can include peptidomimetics of peptide modulators, can be used in the same manner as the initial modulators. Preferred modulators of prion replication would have the ability to cross the blood-brain barrier since a large number of prion manifest themselves in the central nervous system.

An inhibitor can be one that exerts its activity directly on the PrP-res, on the PrP-sen, or on factors required for the conversion of PrP-sen to PrP-res. Regardless of the type of inhibitor or activator identified by the present screening methods, the effect of the inhibition or activation by such a compound results in altered prion amplification or replication as compared to that observed in the absence of the added candidate substance.

M. Kits

Any of the compositions described herein can be included in a kit for carrying out rPrP-PCMA or QUIC. In a non-limiting example, recombinant PrP-sen, prion conversion factors, decontamination solution, and/or conversion buffer with a metal chelator are provided in a kit. The kit further can include reagents for expressing or purifying rPrP-sen. The kit also can include pre-labeled rPrP-sen or reagents that can be used to label the rPrP-sen, with for example, radio isotopes or fluorophores.

In some embodiments, kits are provided for amplification and detection of prion in a sample. In these embodiments, a kit can include, in suitable container, one or more of the following: 1) a conversion buffer; 2) decontamination solution; 3) a positive control, prion containing sample; 4) a negative control sample, not containing prion; or 5) reagents for detection of rPrP-res.

Regents for the detection of prions can include one or more of the following: pre coated microtiter plates for ELISA and/or CDI detection of rPrP-res; or antibodies for use in ELSA, CDI, strip immunochromatography or Western blot detection methods.

Additionally, kits of the disclosure can contain one or more of the following: protease free water; copper salts for inhibiting rPrP-res amplification; EDTA solutions for enhancing prion replication; Proteinase K for the separation of rPrP-res from rPrP-sen; fractionation buffers for the separation of rPrP-res from rPrP-sen, modified, or labeled proteins (to increase sensitivity of detection); or conversion factors (to enhance efficiency of amplification).

In certain embodiments, the conversion buffer is supplied in a "ready for amplification format" where it is allocated in a microtiter plate such that the sample and rPrP-sen can be added to first well, and subjected to primary reaction and amplification. Thereafter a portion of the reaction mix is moved to an adjacent well with additional rPrP-sen added for serial rPrP-res amplification. These steps can be repeated across the microtiter plate for multiple serial amplifications.

The components of the kits can be packaged either in aqueous media or in lyophilized form. The container means of the kits will generally include at least one vial, test tube, plate, flask, bottle, syringe or other container, into which a component can be placed, and optionally, suitably aliquoted. Where there is more than one component in the kit (labeling reagent and label can be packaged together), the kit also generally will contain a second, third or other additional container into which the additional components can be separately placed. However, various combinations of components can be included in a vial. The kits also typically will include a means for containing proteins, and any other reagent containers in close confinement for commercial sale. Such containers can include injection or blow-molded plastic containers into which the desired vials are retained.

When components of the kit are provided in one and/or more liquid solutions, the liquid solution is typically an aqueous solution that is sterile and proteinase free. In some cases protein-based compositions are lyophilized to prevent degradation and/or the kit or components thereof can be stored at a low temperature (for instance, less than about 4° C.). When reagents and/or components are provided as a dry powder and/or tablets, the powder can be reconstituted by the addition of a suitable solvent. It is envisioned that the solvent also can be provided in another container means.

N. rPrP-Res Amplification Assays (rPrP-PMCA/QUIC Assays) Using Samples from Humans, Bovines, and Other Species As described above, it is desirable to carry out rPrP-PMCA and/or QUIC assays in a variety of species. For instance, the assays are useful in screening bovine, sheep, and cervid individuals or populations for prion diseases, for example to ensure the safety of the food supply. In some instances, rPrP-PMCA/QUIC assays are useful for diagnosing prion disease in a human or veterinary subject.

The rPrP-sen chosen may be chosen from the same species as the test sample, or it may be of a different species. For example, a hamster or mouse rPrP-sen can be used to amplify a human or sheep test sample. In particular examples hamster rPrP (rHaPrP) is used because it is particularly effective in amplification reactions, (such as QUIC) not only of hamster PrP-res but of PrP-res from humans and sheep as well. For those embodiments in which the rPrP-sen is from the same species as the test sample, it is also desirable to create rPrP-sen from a variety of species that may be tested. As described above in greater detail, in general, the partial prion protein sequence expressed as rPrP-sen corresponds to the polypeptide sequences of the natural mature full-length $PrP^C$ molecule, meaning that the rPrP-sen polypeptide lacks both the amino-terminal signal sequence and carboxy-terminal glycophosphatidylinositol-anchor attachment sequence. Thus, in some embodiments, a hamster rPrP includes amino acids 23-231 (SEQ ID NO: 1) of hamster prion protein sequence (SEQ ID NO: 8), a bovine rPrP-sen includes amino acids 25-241 (SEQ ID NO: 5) of a bovine prion protein sequence, whereas a human rPrP-sen includes amino acids 23-231 (SEQ ID NOs: 3, 4) of a human prion protein sequence (SEQ ID NOs: 10, 11), an ovine rPrP-sen includes amino acids 25-233 (SEQ ID NO: 6) of an ovine prion protein sequence, and a cervid rPrP-sen includes amino acid residues 25-234 (SEQ ID NO: 7) of a cervid prion protein sequence or residues 90-231 of the hamster sequence (SEQ ID NO: 8). However, the rPrP protein is not limited to these particular portions of each sequence. Other exemplary portions are disclosed above.

As described above in greater detail, the test sample can be any tissue sample from a human or veterinary subject, for instance a brain sample, peripheral organ sample (such as blood, tonsil, spleen, or another lymphoid organ), various excretia or a CSF sample. In the case of living subjects, blood, excretia, or CSF samples are easily obtained with relatively non-invasive techniques. In the case of samples from deceased subjects, brain or other tissue samples are easily obtained.

Once the rPrP-sen and test samples have been obtained, an rPrP-PMCA or QUIC assay is performed as described in detail above. Results generally are available within 24-72 hours, which greatly speeds diagnosis, treatment, and/or disease containment/decontamination efforts.

The following Examples are provided to illustrate certain particular features and/or embodiments. These Examples should not be construed to limit the disclosure to the particular features or embodiments described.

EXAMPLES

Example 1

Materials and Methods

This example describes materials and methods used to carry out Examples 2-8. Although particular methods are described, it is understood that other methods can be used.

Recombinant Prion Protein Expression and Purification

DNA sequences coding for hamster (GENBANK® Accession No. M14054) and mouse (GENBANK® Accession No. BC006703) prion protein residues 23-230 or 90-230 were amplified by standard PCR, ligated into the Kanamycin selective pET41 vector (EMD Biosciences) as NdeI/HindIII inserts, and their sequences were verified. After transforming the plasmids into *E. coli* Rosetta cells (EMD Biosciences), the rPrP-sen was expressed using the Overnight Express Autoinduction system according to the instructions from the manufacturer (EMD Biosciences). A typical mass of wet cell paste was 8-9 grams per Liter of Luria-Bertani media. Cell pellets were lysed with BugBuster™ and Lysonase™ (EMD Biosciences). Approximately 25 mL of BugBuster™ with 50 μL of lysonase and one Complete EDTA-free protease inhibitor tablet (Roche) was used for each gram of harvested bacterial cells. This lysis mixture was stirred with the bacterial cells in an ice bath. This mixture was then subjected to periodic sonication (15 pulses of 15 seconds over ~30 minutes at full power) to facilitate lysis. Inclusion bodies containing rPrP-sen were isolated by centrifugation and then were twice washed with 0.1× BugBuster™ and pelleted by centrifugation in 50 mL centrifuge tubes. The enriched rPrP was further purified by modifications to the method of Zahn et al., (1997) *FEBS Lett.* 417, 400-404. The washed inclusion bodies were then suspended in aqueous 8 M Guanidine hydrochloride and this mixture was pelleted by centrifugation to remove cell debris. The supernatant containing denatured rPrP-sen was stirred with Ni-NTA Superflow (Qiagen) resin and then loaded onto an XK16/20 column (GE Healthcare) and then washed with denaturing buffer (6 M Guanidine hydrochloride, 100 mM sodium phosphate, 10 mM Tris, pH 8.0) and refolded with a linear gradient over 6 hours at a flow rate of 0.75 to 1 mL/minute using an AKTA Explorer 10. The protein was then eluted with 100 mM sodium phosphate (pH 5.8), 500 mM imidazole, 10 mM Tris. Pooled fractions were diluted to 0.2 mg/ml with water, filtered and dialyzed against 10 mM phosphate. The 10 mM phosphate dialysis buffer was diluted from a 1 M stock of the same buffer (pH 5.8) immediately prior to dialysis. After dialysis against a total of 4 L (2×2 L) at 4° C., with the second treatment overnight, the protein solution was sterile filtered through a 0.22 μm 150 mL filter unit (Millipore) and the protein concentration of rPrP was determined by the method of Bradford or by $A_{280nm}$. Purity of the final protein preparations was estimated at ≧99% when analyzed by SDS-PAGE, immunoblotting and MALDI mass spectrometry.

Differences of this method to that of Zahn et al. include the isolation of inclusion bodies that were not isolated in Zahn et al., lysis in non-denaturing Bug Buster instead of lysis in a denaturing buffer, the elimination of the use of a glutathione denaturing buffer, and the elimination of the histidine tag.

rPrP-PMCA rPrP-PMCA reactions were prepared in 0.2 ml PCR tubes as 80 μl solutions containing PBS, pH 7.4, containing 0.05% (w/v) SDS and 0.05% TritonX-100 (TX-100), except as shown in FIG. 1, where 0.1% of each detergent was used. rHaPrP-sen was present at 0.1 mg/ml (4 μM). The reactions were seeded with brain homogenate from Syrian golden hamsters affected with the 263K scrapie strain (ScBH) or purified $PrP^{Sc}$ ($HaPrP^{Sc}$) from the same source (Raymond & Chabry in *Techniques in Prion Research* (eds. Lehmann & Grassi) 16-26 (Birkhauser Verlag, Basel, 2004)). The $PrP^{Sc}$ concentration in the ScBH was estimated by semiquantitative immunoblotting against purified $HaPrP^{Sc}$ standards. Reactions were immersed in water at 37° C. and subjected to repeated cycles of sonication (Misonix Model 3000), based on previous methods (see, for instance, Saa et al., (2006) *J. Biol. Chem.* 281, 35245-35252) with minor modifications. In brief, sonication was performed over 24 hours (constituting one round) with 40 second pulses every 60 minutes at maximum power. Unsonicated controls were incubated at 37° C.

Although rPrP-PMCA will work under a variety of conditions, the optimal conditions that supported specific $PrP^{Sc}$-seeded rPrP-PMCA include the combination of about 0.05-0.1% of an anionic detergent such as SDS and about 0.05-0.1% of a nonionic detergent such as TX-100. These conditions are particularly effective at promoting the formation of $rHaPrP\text{-}res^{(Sc)}$ (notably the 17 kDa PK-resistant species), while reducing $rHaPrP\text{-}res^{(spon)}$ formation within the first 24 hours of unseeded reactions. Previous studies showed that prion protein aggregation can be prompted by low concentrations of anionic detergents (Xiong et al., (2001) *J. Neurochem.* 79, 669-678). Other conditions can promote the spontaneous formation of rPrP-res that includes a ~17-kDa fragment (Bocharova et al. (2006) *J. Biol. Chem.* 281, 2373-2379), so seeding with $PrP^{Sc}$ is not always required for the formation of rPrP-res with a banding pattern like that of $rHaPrP\text{-}res^{(Sc)}$. However, under the rPrP-PMCA conditions set forth in this example, PrP$^{Sc}$ seeding is required, allowing for clear and consistent discrimination between HaPrP$^{Sc}$-seeded and unseeded reactions. Without being bound by theory, it is believed that these specific detergent conditions can partially unfold rPrP-sen, allowing productive contacts between PrP$^{Sc}$ and rPrP-sen that would not otherwise occur spontaneously between rPrP-sen molecules.

QUIC

A different method from PMCA uses Quaking Induced Conversion (QUIC), in which shaking of the reaction mixture replaces sonication for disaggregating aggregates formed during cyclic amplification. Of course both shaking and sonication can be used in an amplification reaction, for example in alternating cycles. In the particular examples of QUIC disclosed herein only shaking of reaction vessels is used.

Either purified PrP$^{Sc}$ or scrapie brain homogenate were used to seed the conversion of rPrP-sen to protease-resistant forms in reactions performed in 0.1% sodium dodecyl sulfate and 0.1% Triton X-100, in PBS at 37° C. in 0.5 ml tubes. Tube shaking was done at 1500 rpm in an Eppendorf Thermomixer R. Proteinase K digestions and immunoblotting were performed as described in the step-by-step protocol, below.

For comparing PK-resistant QUIC reaction products, 24-hour unshaken reactions and reactions were shaken with or without 0.1 mm glass cell disruption beads (Scientific Industries). These reactions were seeded with 10 ng of purified hamster PrP$^{Sc}$ with 0.2 mg/ml hamster rPrP-sen and a 50 µl reaction volume. The tubes were subjected to cycles of 2 minutes of shaking and 28 minutes without shaking. C-terminal antibody R20 was used for the immunoblot.

For 20-hour QUIC reactions performed with the varying rPrP-sen concentrations, reaction volumes, and seed amounts, the seed amounts approximate the estimated quantity of PrP$^{Sc}$ added in 2-µl aliquots dilutions of scrapie brain homogenate (in 1% normal brain homogenate). The tubes were subjected to cycles of 10 seconds of shaking and 110 seconds without shaking. R20 was used for the immunoblot. For extended reactions to QUIC sensitivity to small amounts of scrapie brain homogenate seed, 65-hour and 95-hour QUIC reactions were carried out as described above, and 0.2 mg/ml rPrP-sen, were used for 100-µl reaction volumes. Scrapie brain homogenate seed dilutions containing the designated amount of PrP$^{Sc}$, were subjected to cycles of 10 seconds shaking and 110 seconds without shaking.

In other examples, 48-hour reaction times were used with reduced detergent concentrations (0.05% SDS and 0.05% Triton X-100). For the second round, 10% of the volume of the first round reaction products were diluted into 9 volumes of reaction buffer containing fresh rPrP-sen. PK-digestions and immunoblotting using either R20 or D13 primary antibodies were performed as described below.

For seeding with CSF samples, aliquots (2 µl) of CSF taken from normal hamsters (n=3) or hamsters in the clinical phase of scrapie (n=6) were used to seed QUIC reactions using the conditions, and immunoblots were carried out using the PK-digested products of the first 48-hour round. Ten percent of each first round reaction volume was used to seed a second 48-hour round of QUIC. Antibodies R20 and D13 were used for the immunoblots.

CSF Collection

Hamsters were heavily sedated with isofluorane and exsanguinated using cardiac puncture. Skin and muscles at the back of the neck were dissected away avoiding blood vessels and meninges. A small hole was made at the medial aperture in the meninges using a 26¾ G needle and a Drummond micropipette was quickly inserted into the hole. CSF filled the micropipette by capillary action. Rocky Mountain Laboratories is an AALAC-accredited facility, and all animal procedures were approved by the institution's Animal Use and Care Committee.

At the end of the reaction, 5 µl of the reaction sample (1 µg of rPrP) was diluted five-fold in PBS with 0.1% SDS and digested with the specified PK:rHaPrP ratio (0.025:1=1 µg/ml of PK, 0.25:1=10 µg/ml of PK, or 0.5:1=20 µg/ml of PK) for 1 hour at 37 C. PEFABLOC® (4-(2-Aminoethyl)-benzensulfonyl fluoride (Roche) was then added to a final concentration of 4 mM. For those samples analyzed by western blotting, 20 µg of thyroglobulin was added and the protein was precipitated with 4 volumes of methanol and stored at −20° C. prior to centrifugation and aspiration of the methanol. Pellets were suspended in sample buffer (4 M urea, 4% SDS, 2% β-mercaptoethanol, 8% glycerol, 0.02% bromophenol blue and 50 mM Tris-HCl pH6.8), subjected to SDS-PAGE using 10% BisTris NUGPAGE® (polyacrylamide) gels (Invitrogen), and transferred to IMMOBILON™ P membrane (Millipore). The membrane was probed with D13 (Peretz et al. (2001) *Nature* 412, 739-743), R20 (Caughey et al., (1991) *J. Virol.* 65, 6597-6603), or R18 antibodies at 1:10,000 dilutions as specified, and visualized by ATTOPHOS® AP Fluorescent Substrate System (2'-[2-benzothiazoyl]-6'-hydroxy-benzothiazole phosphate [BBTP]) (Promega) according to the manufacturer's recommendations. For silver staining, methanol precipitation was omitted and the PK-digested samples were mixed with 5x sample buffer, boiled, and analyzed by SDS-PAGE.

Electron Microscopy rHaPrP-res$^{(spon)}$ and rHaPrP-res$^{(Sc)}$ from fourth round reactions were treated with PK (PK:PrP ratio of 0.025:1) at 37° C. for one hour, after which 5 mM PEFABLOC® (4-(2-Aminoethyl)-benzensulfonyl fluoride was added. These and PK untreated samples were pelleted by centrifugation for 30 minutes at 16,100 g, washed twice with PBS or water, and sonicated for one minute. The samples were then settled onto Formvar-coated grids for 15 minutes, washed three times with sterile water, and stained with methylamine tungstate for one minute. Excess stain was removed by filter paper and the samples were dried at room temperature. Images were obtained with an 80 kV in a Hitachi H-7500 electron microscope and an AMT XR-100 digital camera system (Advanced Microscopy Techniques, Danvers, Mass.).

Spectral Analysis rHaPrP-res$^{(spon)}$ and rHaPrP-res$^{(Sc)}$ (seeded with purified HaPrP$^{Sc}$) from third round reactions were pelleted by centrifugation for 30 minutes at 16,100 g and twice washed in 10 µl of sterile water. Slurried pellets were applied to a Golden Gate Single Reflection Diamond Attenuated Total Reflectance unit purged with dehydrated air and dried under a stream of nitrogen. Data collection was performed using a System 2000 IR instrument (Perkin-Elmer) with a liquid nitrogen cooled nbl MCT detector and the following parameters: 20° C., 1 cm$^{-1}$ resolution, 5 cm/s optical path difference velocity, 500 scans 1800-1400 cm$^{-1}$ scan range, and 0.5 cm$^{-1}$ data interval. Primary spectra were obtained by subtracting the corresponding buffer and water vapor spectra. Fourier-self deconvoluted spectra were calculated from the primary difference spectra using a gamma of 19.5 and a smoothing length of 95%. The software used for spectral analyses was Spectrum v2.00 (Perkin-Elmer).

Example 2

Spontaneous Conversion of rPrP-sen

This Example describes the identification of an exemplary set of reaction conditions that allow clear discrimination between PrP$^{Sc}$-seeded and unseeded reaction products. Although particular reaction conditions are specified, one will recognize that other reaction conditions can be used.

Figure 5A:
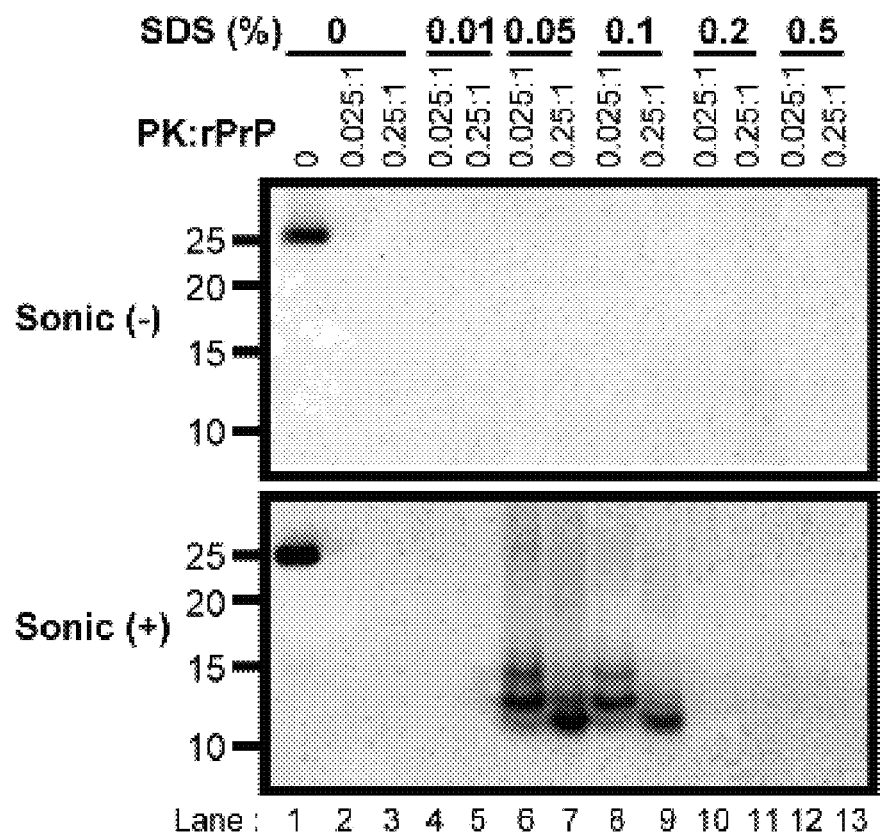
FIG. 5A is a pair of digital images of gels showing the results of rPrP-PMCA. Solutions of rMoPrP (0.4 mg/ml, 16 µM) in PBS pH 7.4, and SDS (0-0.5%) were prepared in 100 µL volumes. The tubes were incubated at 37° C. in a cuphorn sonicator bath. The samples were then subjected to repeated cycles of 9 minutes of incubation followed by 1 minute of sonication at 100% power. After 18 hours, the samples were treated with PK. PK-digested samples were immunoblotted with antibody R20. Upper and lower panels correspond to incubations without and with sonication, respectively. Lane 1 of each panel shows 100 ng of rHaPrP-sen without PK digestion. Molecular mass markers are indicated in kilodaltons on the left side.
Figure 5B:
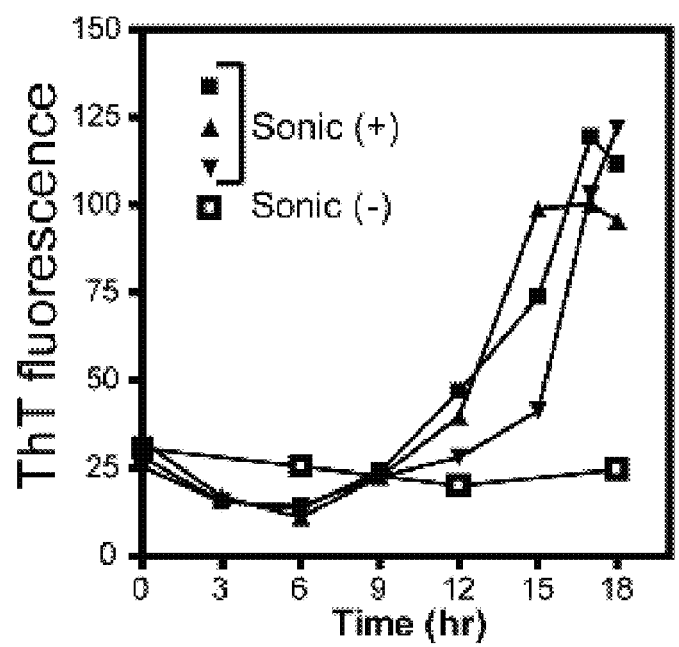
FIG. 5B is a graph showing the kinetics of increase in the fluorescence of the amyloid stain thioflavin T when combined with sonicated or unsonicated samples of rMoPrP in 0.1% SDS as in FIG. 5A. Thioflavin T (ThT) fluorescence typically increases upon interaction with amyloid fibrils (Prusiner (1998) *Proc. Natl. Acad. Sci. U.S.A.* 95, 13363-13383). Aliquots (5 µl) were withdrawn at each time point and diluted into 10 µM thioflavin T, 50 mM glycine pH 8.5 to a volume of 100 µl. Fluorescence emission was measured at 482 nm with excitation at 445 nm. Three independent reactions with sonication are shown relative to a single control reaction done without sonication.
Figure 6A:
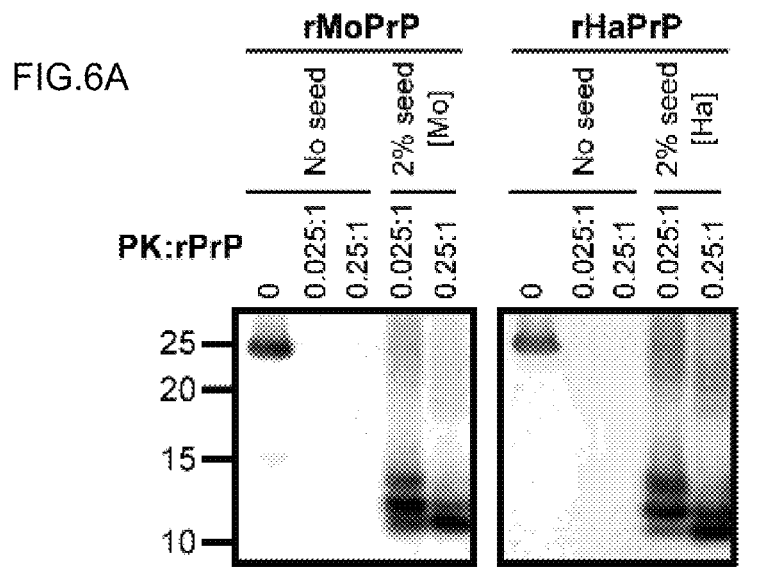
FIG. 6A is a pair of digital images of immunoblots showing products of unsonicated conversion reactions that were either unseeded or seeded with 1.6 µl aliquots of sonicated reactions containing rMoPrP-res$^{(spon)}$ ([Mo]) or rHaPrP-res$^{(spon)}$ ([Ha]) and total prion protein concentrations of 0.4 mg/ml. The seed volumes were added to 80 µL 0.4 mg/ml rMoPrP-sen or rHaPrP-sen in 0.1% SDS, 10 µM thioflavin T (ThT) and PBS, pH 7.4, in 96-well assay plates. The reactions were incubated for 96 hours without sonication. Aliquots were digested with PK at the designated PK:rPrP ratio and analyzed by immunoblotting with antibody R20. The first lane of each panel shows 100 ng of rPrP-sen without PK treatment.
Figure 6B:
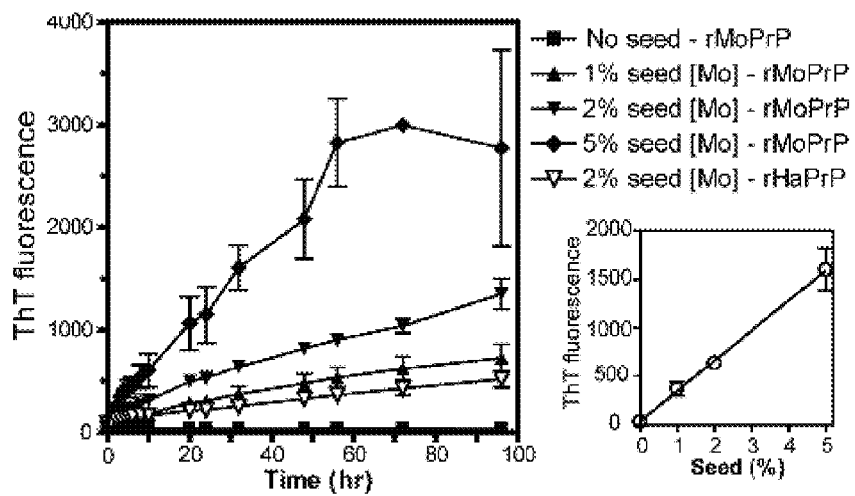
FIG. 6B is a pair of graphs showing the kinetics of reactions seeded with the designated % volumes of rMoPrP-res$^{(spon)}$-containing reaction products, followed by monitoring ThT fluorescence at 482 nm (left graph; data points are means±SD, n=3). The results of heterologous reactions in which rMoPrP-res(spon) was used to seed the conversion of rHaPrP-sen are also shown. The right graph shows the linear relationship between seed concentration and ThT fluorescence (r2=0.998) after 32 hours under these unsonicated reaction conditions.
Figure 6C:
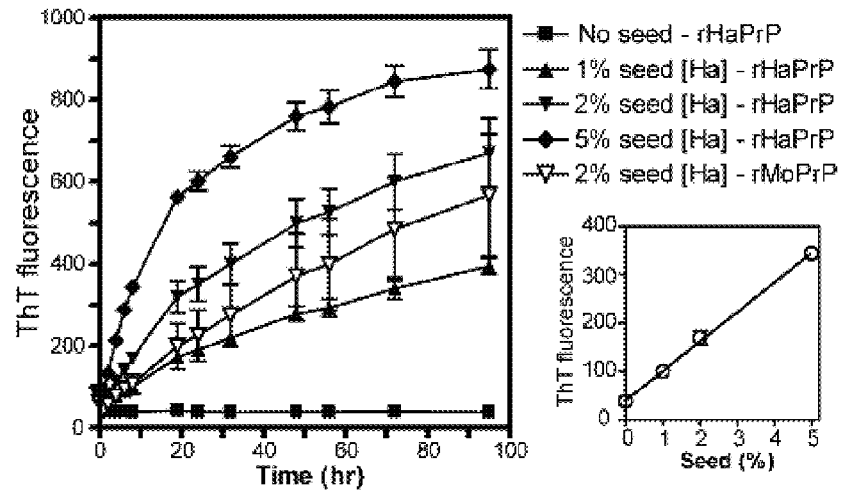
FIG. 6C is a pair of graphs showing the kinetics of analogous homologous and heterologous reactions seeded with rHaPrP-res$^{(spon)}$-containing reaction products. The right graph shows the linear relationship between the amount of seed and ThT fluorescence after 8 hours (r2=0.997).
Figure 7:
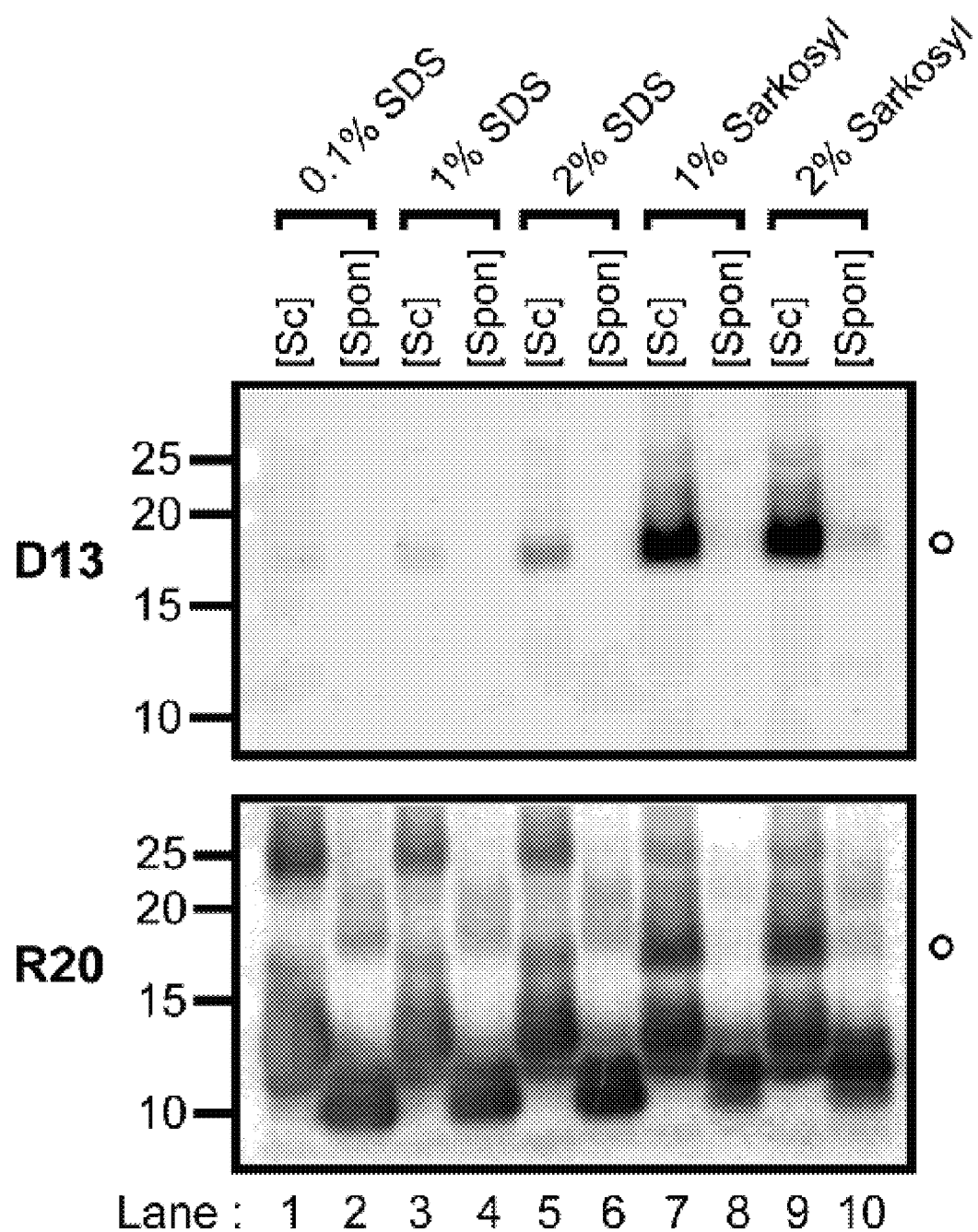
FIG. 7 is a pair of digital images of gels showing the effects of SDS and Sarkosyl upon treatment of rPrP-PMCA reaction products with high concentrations of PK. Aliquots of third round PrP$^{Sc}$-seeded or unseeded rPrP-PMCA reaction products containing either rHaPrP-res$^{(Sc)}$ (Sc) or rHaPrP-res (spon) (spon) were treated with 20 µg/ml PK (PK:PrP ratio=0.5:1) as described in Example 1 except for the addition of the designated concentrations of SDS or Sarkosyl. This PK concentration is 20-fold higher than used in most of the other experiments described herein. This stronger PK treatment in 0.1-2% SDS severely reduced the relative recovery of the characteristic 17 kDa rHaPrP-res$^{(Sc)}$ band (compare to FIG. 5B, lanes 2-7, for example). However, 1-2% Sarkosyl strongly enhanced the recovery of the 17-kDa rHaPrP-res$^{(Sc)}$ band while retaining striking differences between the banding profiles of rHaPrP-res$^{(Sc)}$ and rHaPrP-res$^{(spon)}$. Therefore, the addition of Sarkosyl together with higher concentrations of PK can provide rPrP-PMCA digestion conditions that are more robust and less sensitive to minor variations in PK activity or total protein concentrations of the reaction mixtures.

Development of a PMCA-like reaction for PrP$^{Sc}$ amplification using rPrP-sen as a substrate requires conditions that allow for clear discrimination between PrP$^{Sc}$-seeded and unseeded reaction products. Initial trials revealed that in 0.1% SDS with periodic sonications, bacterially expressed recombinant mouse PrP-sen (rMoPrP-sen; FIG. 5) and hamster PrP-sen (rHaPrP-sen) converted spontaneously to thioflavin T-positive, proteinase K (PK)-resistant forms designated rMoPrP-res$^{(spon)}$ and rHaPrP-res$^{(spon)}$, respectively. The fragments generated by PK-digestion of rMoPrP-res$^{(spon)}$ and rHaPrP-res$^{(spon)}$ were 10-12 kDa, that is, much smaller than the ~17-19 kDa fragment typical of unglycosylated scrapie PrP$^{Sc}$ and PrP$^{Sc}$-induced rPrP-res$^{8-10}$. When seeded into fresh solutions of rMoPrP-sen and rHaPrP-sen, respectively, rMoPrP-res$^{(spon)}$ and rHaPrP-res$^{(spon)}$ elicited more thioflavin T-positive rPrP-res$^{(spon)}$, even without sonication (FIG. 6). However, the addition of 0.1% TX-100 to the 0.1% SDS permitted seeded rPrP-res$^{(spon)}$ accumulation, but often delayed its spontaneous formation for >24 hours even in sonicated reactions. Thus, these conditions were selected for subsequent attempts to seed rHaPrP-sen conversion with PrP$^{Sc}$.

Example 3

Seeding of rPrP-sen Conversion by PrP$^{Sc}$

This example demonstrates that scrapie PrP$^{Sc}$ can seed the conversion of rPrP-sen to rPrP-res.

Scrapie PrP$^{Sc}$ purified from hamster brains (HaPrP$^{Sc}$; Raymond & Chabry in *Techniques in Prion Research* (eds. Lehmann & Grassi) 16-26 (Birkhauser Verlag, Basel, 2004)) was used to seed the conversion of rHaPrP-sen. PK-resistant fragments seeded by PrP$^{Sc}$ (rHaPrP-res$^{(Sc)}$, where $^{(Sc)}$ refers to seeding by PrP$^{Sc}$) were generated with seed-to-substrate ratios of 1:100 (400 ng $HaPrP^{Sc}$) and 1:1,000 (40 ng $HaPrP^{Sc}$) in both the unsonicated and sonicated reactions, but, when sonicated were much more abundant and less dependent on the amount of seed (FIG. 1A). When analyzed by immunoblotting using an anti-PrP antibody R20 directed toward C-terminal residues 219-232, rHaPrP-$res^{(Sc)}$ consisted of 4 PK-resistant fragments (11, 12, 13 and 17 kDa). In contrast, and as expected, the unseeded reactions gave either no PK-resistant bands (FIG. 1A) or, more rarely, rHaPrP-$res^{(spon)}$ with only the smaller 10-, 11- and 12-kDa fragments (FIG. 1A). The 17-kDa rHaPrP-$res^{(Sc)}$ band also was not observed in the absence of rHaPrP-sen substrate, demonstrating that the $HaPrP^{Sc}$ seed itself did not display this band (FIG. 1A). Collectively, these data demonstrate that $HaPrP^{Sc}$-seeded rPrP-sen conversion reactions can be distinguished from unseeded reactions by immunoblot comparison of the PK-resistant banding patterns. Most notable was the formation of the 17 kDa-band in the $HaPrP^{Sc}$-seeded reactions as has been observed previously in substoichiometric conversion reactions with rPrP-sen (Iniguez et al., (2000) *J. Gen. Virol.* 81, 2565-2571; Kirby et al., (2003) *J. Gen. Virol.* 84, 1013-1020; Eiden et al., (2006) *J. Gen. Virol.* 87, 3753-3761).

The ability of rHaPrP-$res^{(Sc)}$ to seed additional rounds of rHaPrP-$res^{(Sc)}$ amplification was tested by diluting products of the first-round $HaPrP^{Sc}$-seeded reaction seeded (FIG. 1A) into fresh rHaPrP-sen substrate. For brevity, the term "rPrP-PMCA" is used when referring to the use of rPrP-sen as a substrate in combination with periodic sonication and (optionally) cyclic dilutions of reaction products into fresh substrate to detect $PrP^{Sc}$ and amplify rHaPrP-$res^{(Sc)}$. Without sonication, the rHaPrP-$res^{(Sc)}$ produced in both the first and second rounds decreased with dilution of the seed (FIGS. 1A, 1B). With sonication, the yield was less dependent upon seed concentration, with similarly high levels of rHaPrP-$res^{(Sc)}$ produced at each dilution (FIGS. 1A, 1B). Similar levels of rHaPrP-$res^{(Sc)}$ were produced in each of five consecutive rounds of amplification with the products of each round diluted 1,000-fold into newly prepared rHaPrP-sen. Overall, periodic sonication reduced the amount of $HaPrP^{Sc}$ required to initiate robust rHaPrP-$res^{(Sc)}$ generation.

To further clarify the difference in the PK susceptibility between rHaPrP-$res^{(Sc)}$ and rHaPrP-$res^{(spon)}$, immunoblots were performed with additional antibodies (FIG. 1C). Monoclonal antibody D13 (directed against residues 96-106 (Peretz et al. (2001) *Nature* 412, 739-743)) specifically recognized the $PrP^{Sc}$-induced 17 kDa band but not the lower molecular weight fragments. In contrast, the polyclonal antibody R18 (directed against residues 142-154 (Peretz et al. (2001) *Nature* 412, 739-743)) recognized 17 kDa, 13 kDa and 12 kDa fragments in rHaPrP-$res^{(Sc)}$ and 12 kDa fragments in rHaPrP-$res^{(spon)}$. The C-terminal antibody R20 reacted with all of the rHaPrP-res fragments, including the shortest 10 kDa fragment that appears to be specific for rHaPrP-$res^{(spon)}$, indicating these fragments differed primarily at their N-termini. Distinct fragment patterns were observed for rHaPrP-$res^{(Sc)}$ and rHaPrP-$res^{(spon)}$ over a wide range of PK:rPrP ratios (FIG. 1C) and detergent compositions (FIG. 7). In agreement with the R20 immunoblots (FIG. 1C), silver-stained SDS-PAGE gels of PK-digested third-round reaction products confirmed that rHaPrP-$res^{(Sc)}$ comprised primarily the 11, 12, 13 and 17 kDa bands while rHaPrP-$res^{(spon)}$ comprised the 10, 11 and 12 kDa bands (FIG. 1D). Thus, $PrP^{Sc}$-seeded and non-seeded reaction products differed in their susceptibility to proteolytic cleavage, providing compelling evidence for fundamental differences in conformation.

Example 4

Ultrasensitive Detection of $PrP^{Sc}$

To determine the minimum amount of $PrP^{Sc}$ detectable by rPrP-PMCA, scrapie brain homogenates (ScBH) were diluted serially with 1% normal brain homogenate (NBH) and were used to seed rPrP-PMCA reactions. The PK-treated products were analyzed by immunoblotting with D13 antibody. After a single round, the 17-kDa rHaPrP-$res^{(Sc)}$ band was detected in reactions seeded with a $6\times10^{-8}$ dilution of ScBH containing $\geqq$10 fg ($10^{-15}$ g) of $PrP^{Sc}$ (FIG. 2A). With a second round of amplification seeded with 10% of the first round reaction products, the sensitivity improved, allowing consistent detection of dilutions of ScBH containing ~50 ag ($5\times10^{-17}$ g), or ~1,000 molecules, of the original $HaPrP^{Sc}$ seed (FIG. 2B). This amount of ScBH typically would contain an average of 0.003 i.c. $LD_{50}$ (a dose lethal to 50% of inoculated hamsters) of scrapie infectivity according to 3 independent end-point dilution bioassays of other brain homogenates stocks prepared from Syrian hamsters in the clinical phase of scrapie (Silveira et al. (2005) *Nature* 437, 257-261). A subset of replicate reactions were positive with further dilutions of ScBH containing ~10-20 ag (nominally) of $HaPrP^{Sc}$. However, none of the NBH controls or samples seeded with more dilute ScBH gave detectable 17-kDa bands. Further rounds of rPrP-PMCA did not increase the sensitivity of $PrP^{Sc}$ detection. These results indicate that rPrP-PMCA can detect sublethal amounts of scrapie-infected tissue.

Example 5

Electron Microscopy and Fourier Transform Infrared Spectroscopy (FTIR)

This Example describes electron microscopy and Fourier transform infrared spectroscopy of rHaPrP-res$^{(Sc)}$ and rHaPrP-res$^{(spon)}$.

Negative-stained transmission electron microscopy of rHaPrP-res$^{(Sc)}$ and rHaPrP-res$^{(spon)}$ revealed that both contained short bundles of fibrillar aggregates, which were especially apparent after PK treatments (FIG. 8). However, other than a tendency of rHaPrP-res$^{(Sc)}$ to be bundled laterally more than rHaPrP-res$^{(spon)}$, we observed no consistent ultrastructural differences between the two types of fibrils.

Figure 9B:
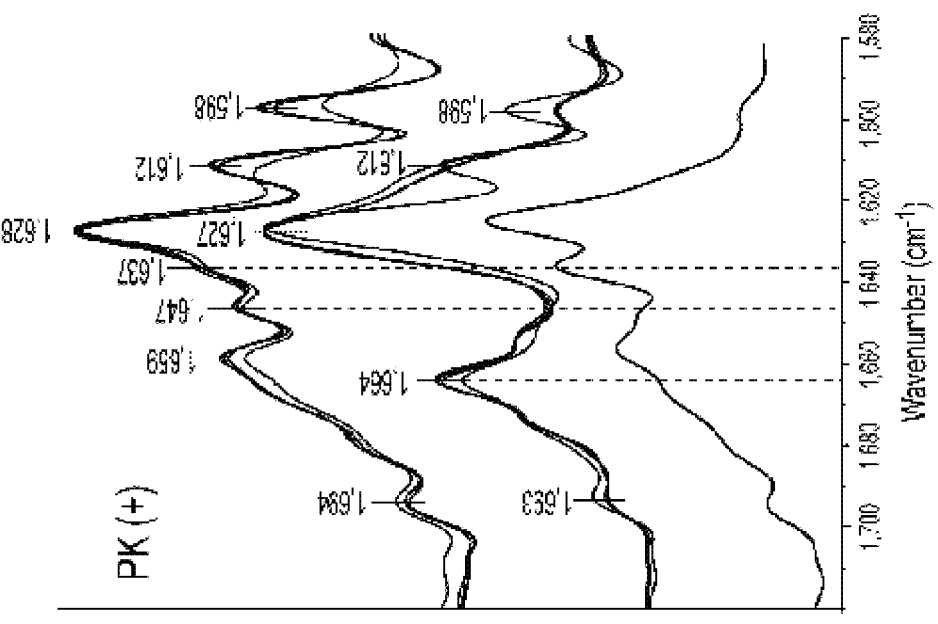
FIG. 9 is a series of graphs showing Fourier transform infrared spectroscopy (FTIR) spectroscopy of rHaPrP-res$^{(Sc)}$ and rHaPrP-res$^{(spon)}$. To compare the secondary structures of rHaPrP-res$^{(Sc)}$ and rHaPrP-res$^{(spon)}$, samples were prepared using three sequential rounds of rPrP-PMCA so that the original HaPrP$^{Sc}$ remaining in the seeded sample was <0.0001% of the total prion protein analyzed. Portions of each sample were left undigested (FIG. 9A) or digested with PK (FIG. 9B) and analyzed by FTIR. The spectrum of the rHaPrP-sen substrate is shown for comparison. Overlaid spectra are from independent preparations. As expected, rHaPrP-sen had an absorbance maximum at ~1652 cm$^{-1}$, consistent with prominent α-helical and/or disordered secondary structures. In contrast, both rHaPrP-res$^{(Sc)}$ and rHaPrP-res$^{(spon)}$ displayed prominent bands at lower wavenumbers (1615-1628 cm$^{-1}$), indicating higher proportions of β-sheet. However, the location of the bands differed between the two types of rHaPrP-res. Without PK treatment, the rHaPrP-res$^{(Sc)}$ had maxima at 1628 and 1615 cm$^{-1}$, whereas rHaPrP-res$^{(spon)}$ peaked at 1625 cm$^{-1}$. After PK digestion of both types of rHaPrP-res, the intensities of bands in the region associated with the α-helix and/or disordered structures were attenuated. Prominent differences remained between rHaPrP-res$^{(Sc)}$, with maxima at 1659, 1647, 1637 and 1628 cm$^{-1}$, and rHaPrP-res$^{(spon)}$, with maxima at 1664 and 1627 cm$^{-1}$. These spectral differences could be due to differences in conformation, PK-resistant polypeptide chain length, or both. Precise assignments of these bands are uncertain, but the 1664 cm$^{-1}$ band is often associated with turns, and the 1659 and 1647 cm$^{-1}$ bands with loops or helices, and disordered structures, respectively. Of particular interest is the 1637 cm$^{-1}$ band of PK-digested rHaPrP-res$^{(Sc)}$. This band also features prominently in the spectrum of 263K HaPrP$^{Sc}$ (spectrum of PK-treated sample is shown in FIG. 9B) and is absent from the spectrum of the DY strains of HaPrP$^{Sc}$, indicating that strain-dependent structure associated with the 1637 cm$^{-1}$ band in 263K HaPrP$^{Sc}$ was replicated in rHaPrP-res$^{(Sc)}$. This provides further evidence of the conformational fidelity of rPrP-PMCA amplification.
Figure 9A:
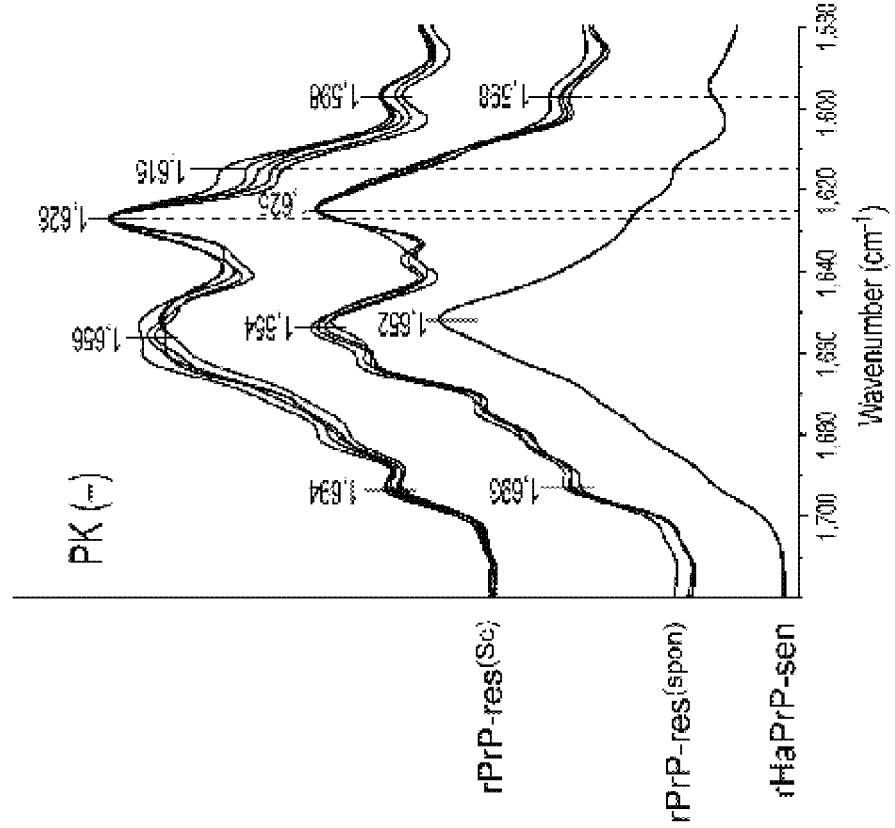

Comparisons of the secondary structures of rHaPrP-res$^{(Sc)}$ and rHaPrP-res$^{(spon)}$ by FTIR provided additional evidence that they differ in conformation (FIG. 9). The value of rHaPrP-res$^{(Sc)}$ as a PrP$^{Sc}$ surrogate will depend in part upon the extent to which it mimics PrP$^{Sc}$ conformationally. Comparison of rHaPrP-res$^{(Sc)}$ versus rHaPrP-res$^{(spon)}$ showed that the former has a distinct PK-resistant fragmentation pattern and an FTIR band at 1637 cm$^{-1}$ (FIG. 9) that is reminiscent of 263K HaPrP$^{Sc}$ itself[23,24]. There are also differences between the rPrP-res fragment pattern and FTIR spectra of rHaPrP-res$^{(Sc)}$ and HaPrP$^{Sc}$. These differences could either be due to fundamental conformational differences or to the lack of GPI anchor, N-linked glycans, brain-derived ligands, or impurities in the rPrP-res. Furthermore, it is not known whether rHaPrP-res$^{(Sc)}$ is infectious, so caution should be used in interpreting conformational analyses of rHaPrP-res$^{(Sc)}$. Nonetheless, the data indicate that rHaPrP-res$^{(Sc)}$ is more closely related to bona fide HaPrP$^{Sc}$ than is rHaPrP-res$^{(spon)}$.

Example 6

Competition Between rHaPrP-res$^{(Sc)}$ and rHaPrP-res$^{(spon)}$

This Example describes the competition between rHaPrP-res$^{(Sc)}$ and rHaPrP-res$^{(spon)}$ seen when reactions are seeded with both rHaPrP-res$^{(Sc)}$ and rHaPrP-res$^{(spon)}$.

The effects of dual seeding of rPrP-PMCA reactions with both rHaPrP-res$^{(Sc)}$ and rHaPrP-res$^{(spon)}$ were tested using different seed ratios (FIG. 3). When the amounts of each seed were equivalent, a mixture of the expected rHaPrP-res$^{(Sc)}$ and rHaPrP-res (spon) reaction products was observed. However, when one seed concentration was kept constant, addition of the other seed reduced the formation of products expected from the first type of seed. Excesses of 10- to 100-fold of one seed type nearly eliminated the seeding activity of the other. This competition and/or interference between the two types of seed makes it unlikely that, once either rHaPrP-res$^{(Sc)}$ or rHaPrP-res$^{(spon)}$ fibrils are prevalent in a reaction, the other could overtake the reaction. This effect is probably due to competition for the rPrP-sen substrate between mutually exclusive types of fibrils.

Example 7

Seeding with Cerebral Spinal Fluid (CSF)

This example demonstrates that CSF samples can be used to discriminate uninfected and scrapie-affected hamsters by rPrP-PMCA.

Figure 4B:
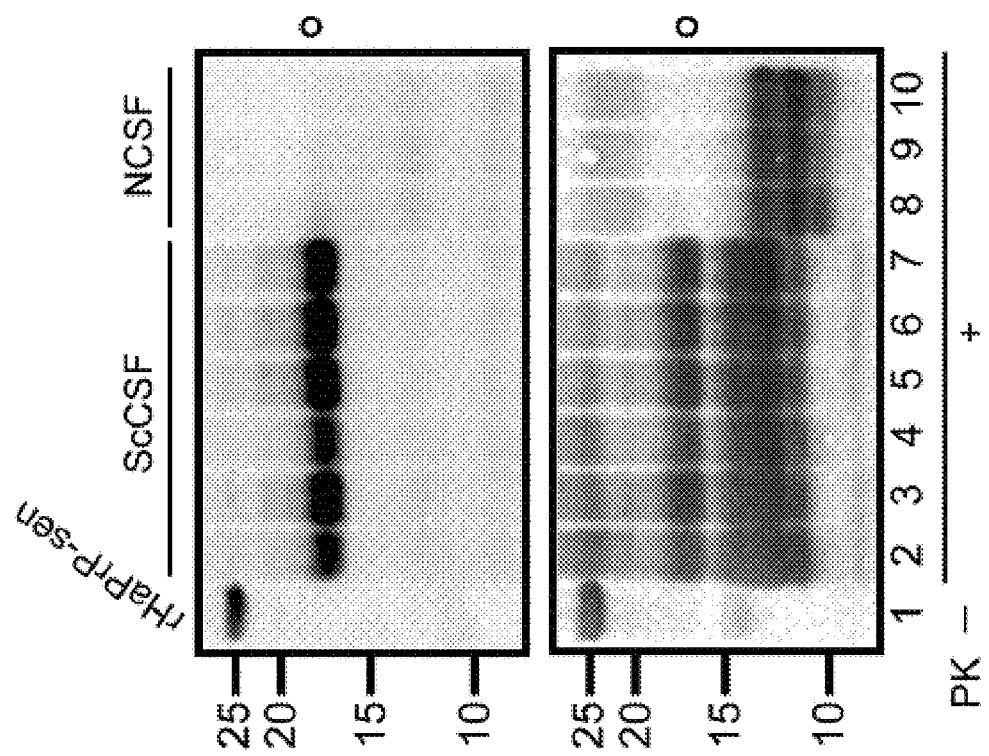
FIG. 4 is a pair of digital images of gels showing the results of seeding rPrP-PMCA with cerebrospinal fluid (CSF). Aliquots (2 µl) of CSF taken from normal hamsters (n=3) or hamsters in the clinical phase of scrapie (n=6) were used to seed rPrP-PMCA reactions. Immunoblots of the PK-digested products of the first 24-hour round are shown in FIG. 4A. Ten percent of each first round reaction volume was used to seed a second 24-hour round of rPrP-PMCA and the PK-digested products of the latter are shown in FIG. 4B. Antisera D13 and R20 were used for the immunoblots. Lane 1 of each panel shows 100 ng HaPrP-sen without PK treatment. The rPrP-PMCA reaction products were digested with a PK:PrP ratio of 0.025:1 (w/w). The positions of the 17-kDa rHaPrP-res$^{(Sc)}$ band are marked with a circle.
Figure 4A:
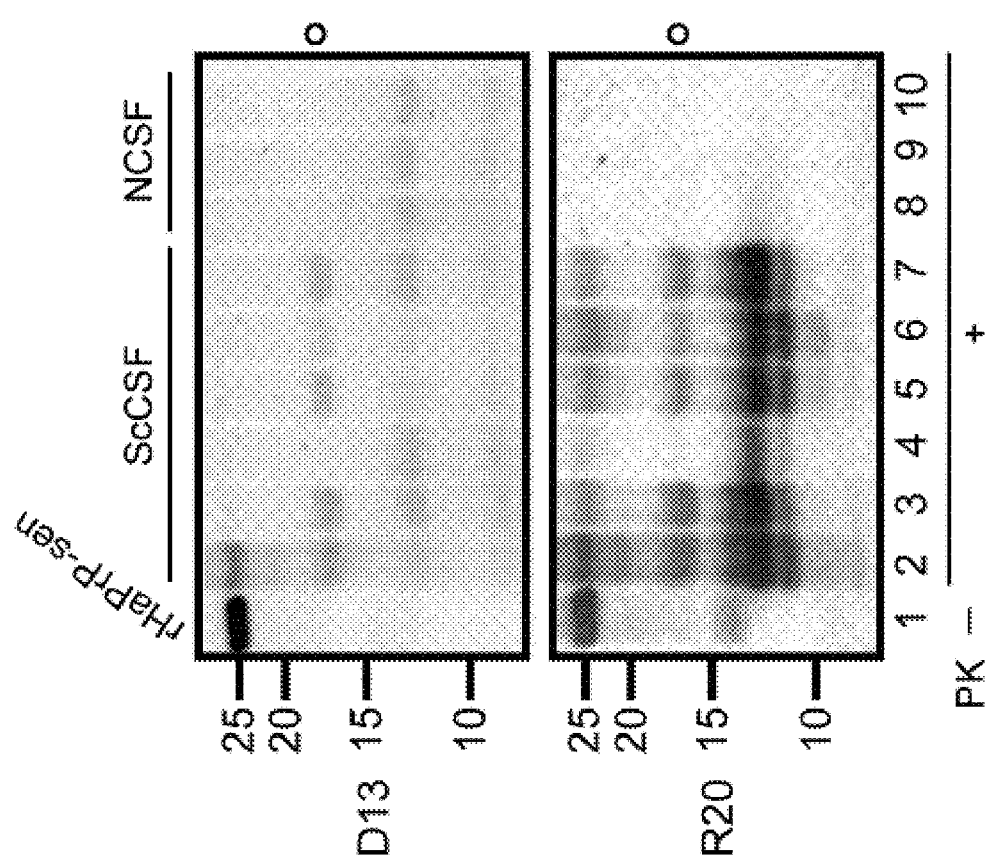

Because CSF is more accessible than brain tissue, rPrP-PMCA seeding activity was compared in CSF samples collected from six hamsters showing clinical signs of scrapie and three uninfected control animals (all male). After one 24-hour round, no rHaPrP-res was observed in the control reactions. However, all of the scrapie CSF reactions produced the typical rHaPrP-res$^{(Sc)}$ banding pattern with variable intensities (FIG. 4A). After second reactions seeded with 10% of the volume of the first round reactions, the control reactions each showed typical rHaPrP-res$^{(spon)}$ patterns, while the scrapie-seeded reactions produced strong rHaPrP-res$^{(Sc)}$ patterns of relatively uniform intensity (FIG. 4B). Analysis of CSF samples from 11 additional uninfected control hamsters (2 females and 9 males) in a 2-round rPrP-PMCA gave either no rHaPrP-res or the rHaPrP-res$^{(spon)}$ pattern. Thus, CSF samples can be used to discriminate uninfected and scrapie-affected hamsters by rPrP-PMCA.

Example 8

QUIC

This Example demonstrates that rPrP-PMCA can be carried out in the form of an alternative assay referred to herein as QUIC (quaking-induced conversion). In a QUIC assay, aggregates are disrupted with periodic shaking of the reaction mix, rather than (or in addition to) sonication.

Some laboratories have found the classical PMCA reaction to be challenging to duplicate consistently, apparently due primarily to difficulties in preparing the required brain homogenate substrate preparations and delivering consistent sonication energy to multiple reactions. To circumvent the aforementioned problems with sonication, the QUIC assay was developed as a simplified and more easily replicable method for sensitive PrP$^{Sc}$ and/or prion detection. Like rPrP-PMCA, QUIC uses rPrP-sen as a substrate, but substitutes periodic shaking for sonications. Even with this modification, QUIC still can be approximately 10 times faster than the current PMCA method that used brain homogenate as a source of PrP-sen. The QUIC method is able to detect about 1 lethal intracerebral scrapie dose within about 8 hours, and subinfections doses with longer protocols. Under cell-free conditions with intermittent shaking, sub-fentogram amounts of PrP$^{Sc}$ in brain homogenate and 2 μl cerebral spinal fluid (CSF) from scrapie-affected hamsters seeded the conversion of recombinant prion protein into easily detectable quantities of specific protease-resistant isoforms.

A solution of 0.2 mg/ml full-length bacterially expressed hamster rPrP-sen (residues 23-231) was seeded with 10 ng of purified hamster PrP$^{Sc}$ (263K strain) and the reaction incubated for 25 hours with or without periodic shaking (FIG. 10A). Treatment of the reaction products with proteinase K (PK) and immunoblotting using an antiserum (R20) raised against a C-terminal PrP epitope revealed PrP$^{Sc}$-seeded PK-resistant conversion products (rPrP-res$^{(Sc)}$). Consistent with previous observations with sonicated (rPrP-PMCA) reactions (described herein), QUIC reactions produced prominent rPrP-res$^{(Sc)}$ bands of 17, 13, 12 and 10 kDa. Without shaking, the same rPrP-res$^{(Sc)}$ bands were produced, but were much less intense.

Figure 11:
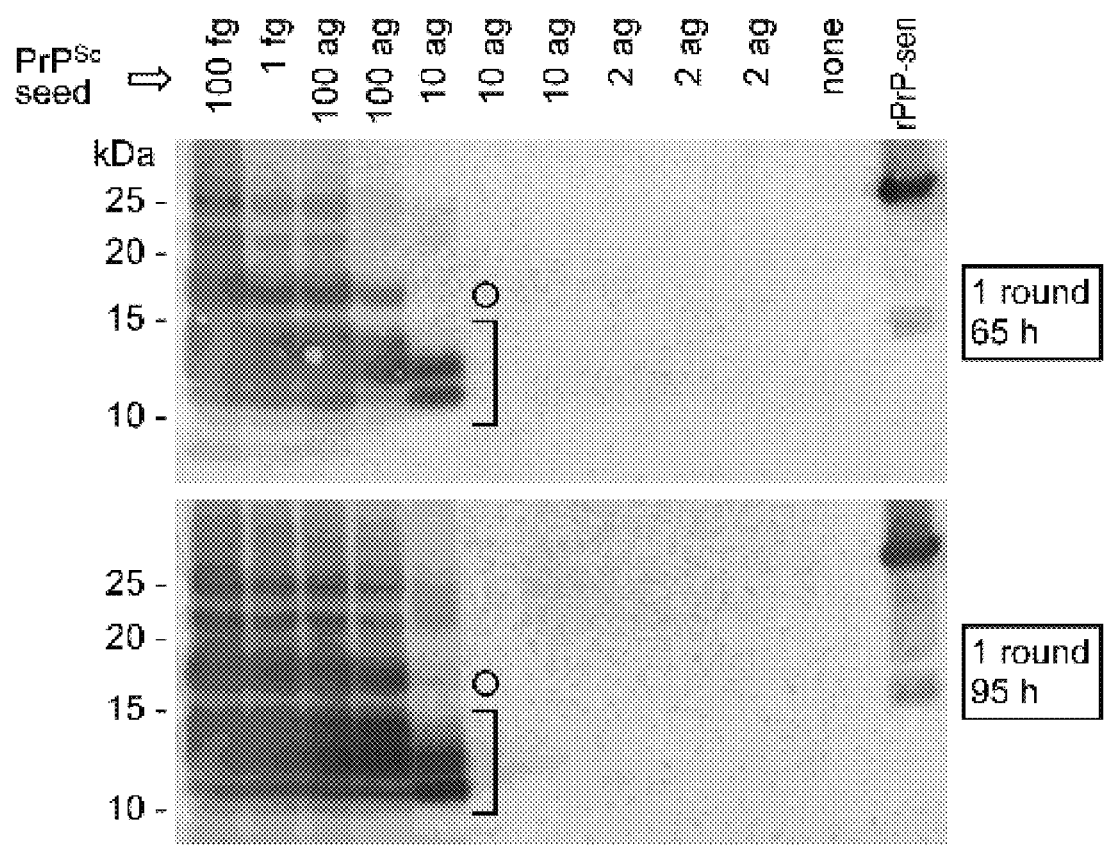
FIG. 11 is a pair of digital images of gels showing that extended reactions can enhance QUIC sensitivity to small amounts of scrapie brain homogenate seed. QUIC reactions were performed with 0.1 mg/ml rPrP-sen and the designated reaction volumes and seed amounts using the shaking cycle and buffer conditions described for FIG. 10B. Two digital images are shown, 65-hour (upper blot) and 95-hour (lower blot) QUIC reactions were performed as using 100-µl reaction volumes and dilutions of scrapie brain homogenate containing the designated amount of PrP$^{Sc}$. The lanes marked 'none' received comparable amounts of normal brain homogenate only. Antiserum R20 was used for these blots. Open circles designate the 17-kDa rHaPrP-res$^{(Sc)}$ band and brackets designate the positions of the 10-13 kDa rHaPrP-res$^{(Sc)}$ or rHaPrP-res$^{(spon)}$ bands. The positions of molecular mass markers are designated in kDa on the left.

Dilutions of scrapie brain homogenate were then seeded in normal brain homogenate and the rPrPsen concentration and reaction volume were varied (FIG. 10B). In 20-hour reactions, 100 μl reactions with 0.2 mg/ml rPrP-sen produced the most intense rPrP-res$^{(Sc)}$ bands using seed dilutions containing as little as 10 fg PrP$^{Sc}$. Reactions seeded with only normal brain homogenate produced either no PK-resistant products or a spontaneously arising product(s), rPrP-res$^{(spon)}$, that gives a set of 10-13 kD PK-resistant bands. The latter were similar to those observed previously in unseeded rPrP-PMCA assays as described herein. With 48-hour incubations at 0.2 mg/ml rPrP-sen, still smaller amounts of scrapie brain homogenate seeded detectable rPrP-res$^{(Sc)}$ in both 50- and 100-μl reactions, with the latter being more sensitive (FIG. 11A). Similar to previous findings with rPrP-PMCA reactions, when the blot was probed with an antibody to an epitope within PrP residues 96-106 (D13), the 17-kDa band was stained preferentially. This indicated that the smaller 10-13 kDa bands that stained with the C-terminal antibody R20 were C-terminal fragments that lacked the D13 epitope. With 65- and 95-hour incubations of 100 μl reactions, seed dilutions containing as little as 100 ag PrP$^{Sc}$ produced strong rPrP-res$^{(Sc)}$ signals (FIG. 11).

Figure 12:
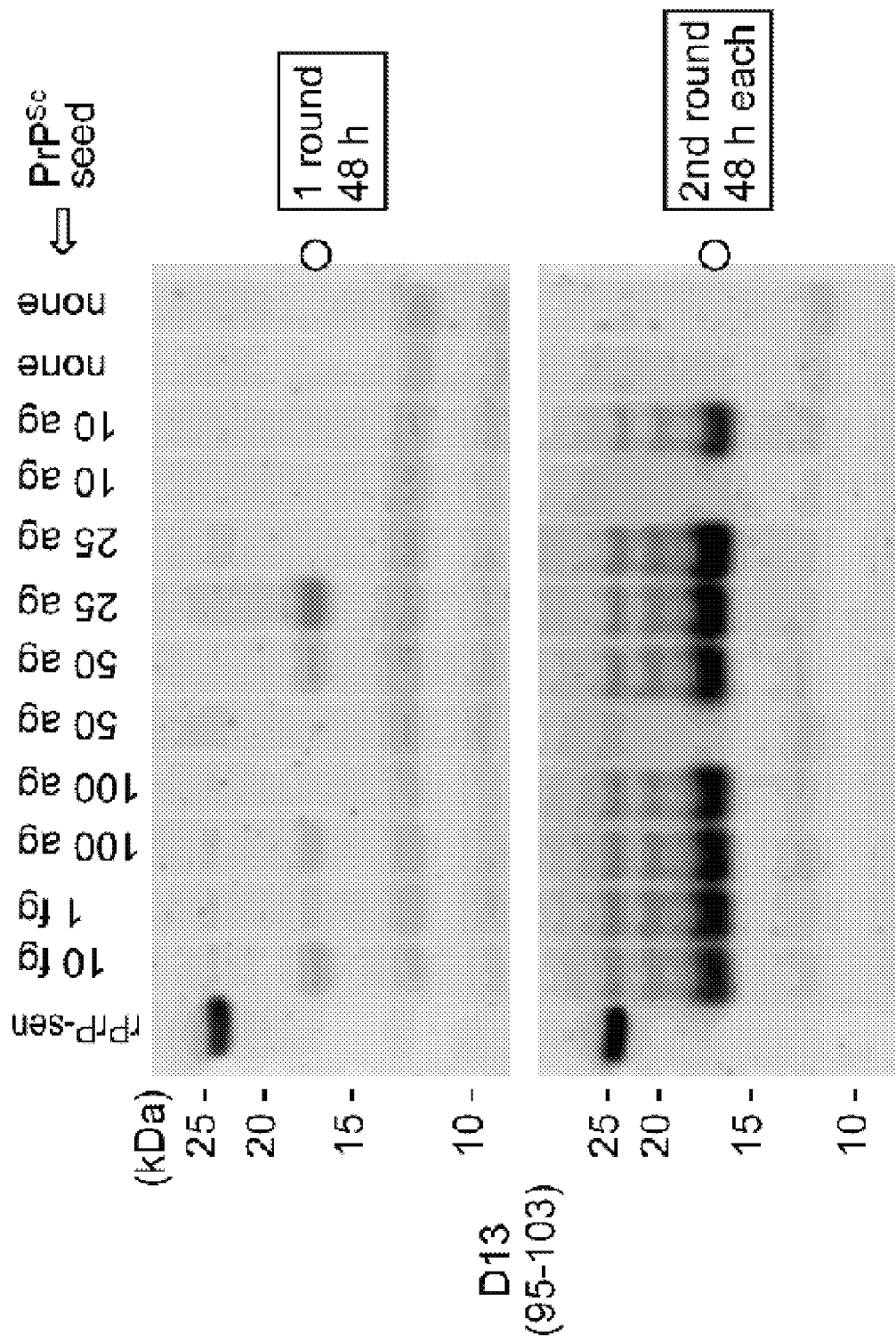
FIG. 12 is a digital image of a gel showing the results of serial QUIC reactions. For the first round, QUIC reactions were performed under the conditions described in the brief description of FIG. 11B, except for the use of 48-hour reaction times and reduced detergent concentrations (0.05% SDS and 0.05% Triton X-100). For the second round, 10% of the volume of the first round reaction products were diluted into 9 volumes of reaction buffer containing fresh rPrP-sen. PK-digested products were immunoblotted using D13 primary antibody. Open circles designate the 17-kDa rHaPrP-res$^{(Sc)}$ band. The positions of molecular mass markers are designated in kDa on the left.

In order to further improve sensitivity, two serial rounds of QUIC reactions were performed in which products of a first 48-hour round were diluted into fresh rPrP-sen for a second-round reaction (FIG. 12). In the first round, seeds nominally containing as little as 25-50 ag of PrP$^{Sc}$ were frequently positive. After second reactions seeded with 10% of the volume of the first round reactions, more consistent detection of sub-femptogram amounts of PrP$^{Sc}$ was observed with one of the 10-ag seeded samples being positive for rPrP-res$^{(Sc)}$.

Figure 13A:
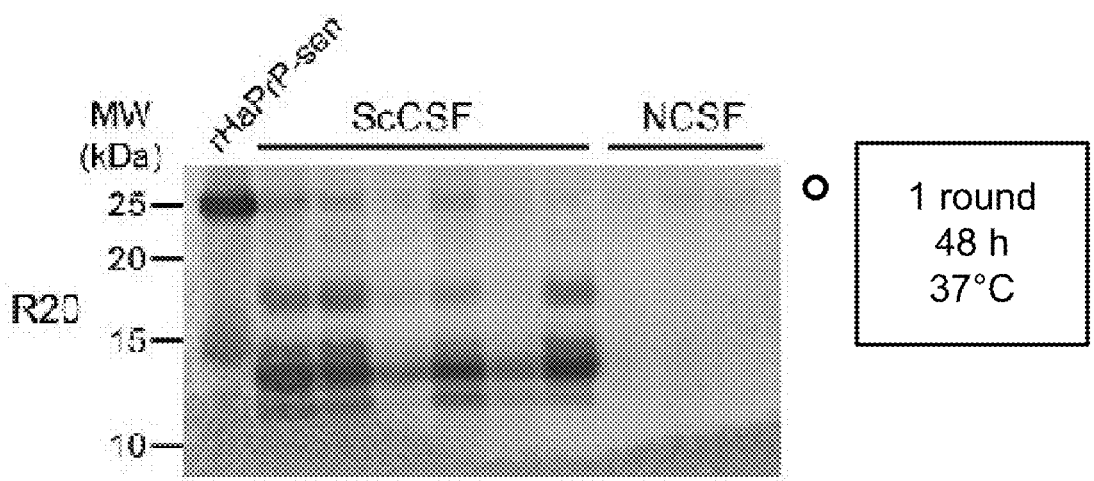
FIG. 13A shows immunoblots with antibody R20 of the PK-digested products of the first 48-h round.
Figure 13B:
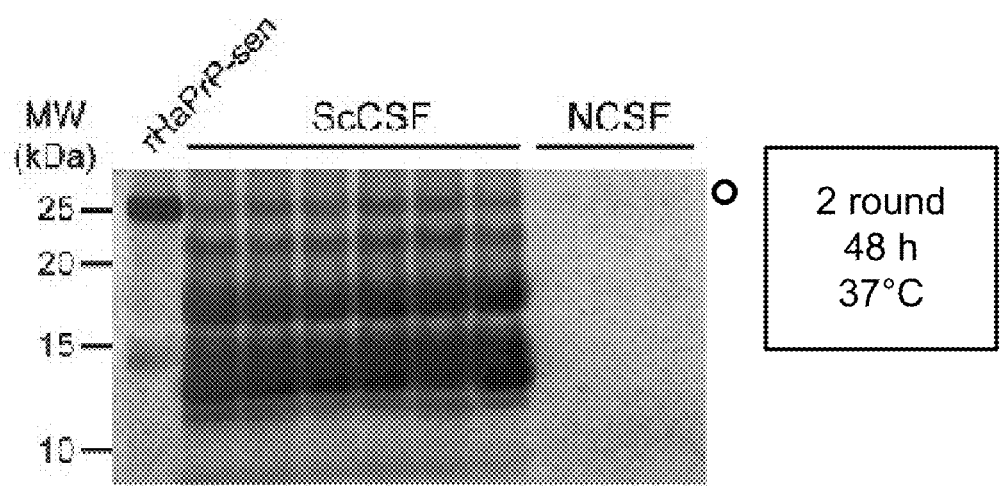
FIG. 13B is an R20 immunoblot showing products of second-round reactions seeded with 10% of each first round reaction volume.

Because cerebral spinal fluid (CSF) is a more accessible biopsy specimen than brain, rPrP-PMCA seeding activity was compared in CSF samples collected from both hamsters showing clinical signs of scrapie and uninfected control animals. After one 48-hour round, no rHaPrP-res was observed in the control reactions. However, all of the scrapie CSF reactions produced the typical rHaPrP-res$^{(Sc)}$ banding pattern with variable intensities (FIG. 13). After the second serial reaction rounds, the control reactions still lacked rPrP-res, while the reactions seeded with scrapie CSF produced strong rHaPrP-res$^{(Sc)}$ patterns of relatively uniform intensity. Thus, QUIC reactions seeded with CSF samples can discriminate between uninfected and scrapie-affected hamsters.

Thus, QUIC provides a simple and easily duplicated alternative to sonication for supporting an ultra-sensitive assay for prions. With sonication of reaction tubes in cuphorn probes, the delivery of vibrational energy to samples can vary substantially and unpredictably with tube position, tube construction, probe age, bath volume, and the redistribution of samples within the tubes by sonication-induced atomization and condensation. In contrast, when a group of sample tubes are shaken in a rack, each tube is subjected to the same motion, making it easier to treat all reactions equivalently. The sonicated rPrP-PMCA reactions is somewhat faster and more sensitive than the shaken QUIC reactions when both are performed at 37° C., but elevating the temperature of the QUIC reactions improves the speed of the reaction and can shorten the overall assay length.

The observation that the QUIC assay can discriminate between CSF samples taken from control and scrapie-affected hamsters indicates that a diagnostic test for prion infections based on CSF samples, as opposed to brain tissue, is feasible.

Figure 18:
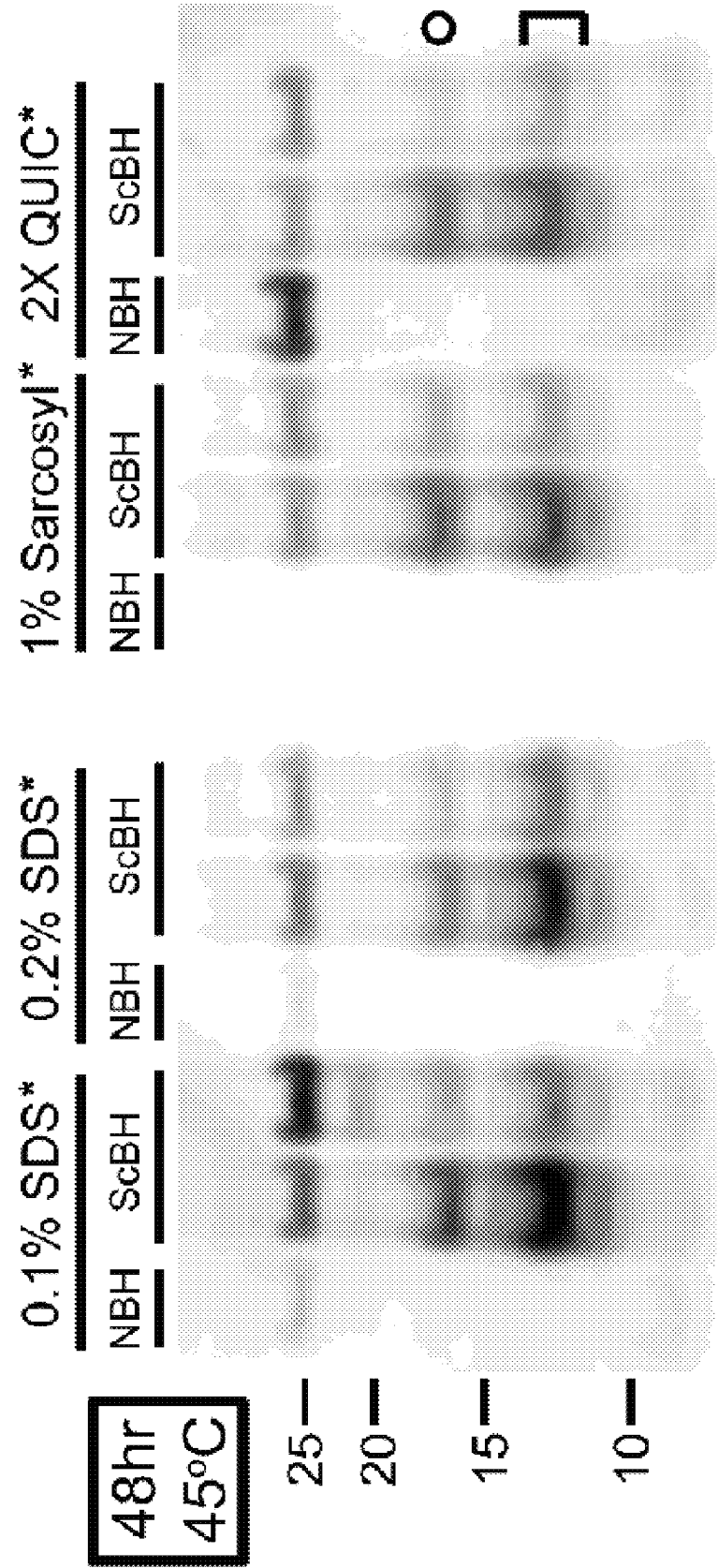
FIG. 18 illustrates the effect of detergent conditions on PK digestion of QUIC reaction products. QUIC reactions performed at 45° C. were seeded with scrapie brain homogenates (diluted in N2) containing 100 fg of PrP$^{Sc}$ or the same dilution of normal brain homogenate (NBH). The shaking cycle was 10 seconds on and 110 second off, and the buffer conditions were as described in connection with FIG. 16. 10-μl aliquots of the reaction products were mixed with 4 μl of the designated detergent solutions and digested with 7 μg/ml PK (final concentration) for 60 minutes at 37° C. The samples were then immunoblotted using R20 antibody. The positions of molecular mass markers are designated in kDa on the left; the open circles designate the position of the 17 kDa band and the bracket the 10-13 kDa bands. The upper band represents residual full length rPrP molecules.
Figure 19:
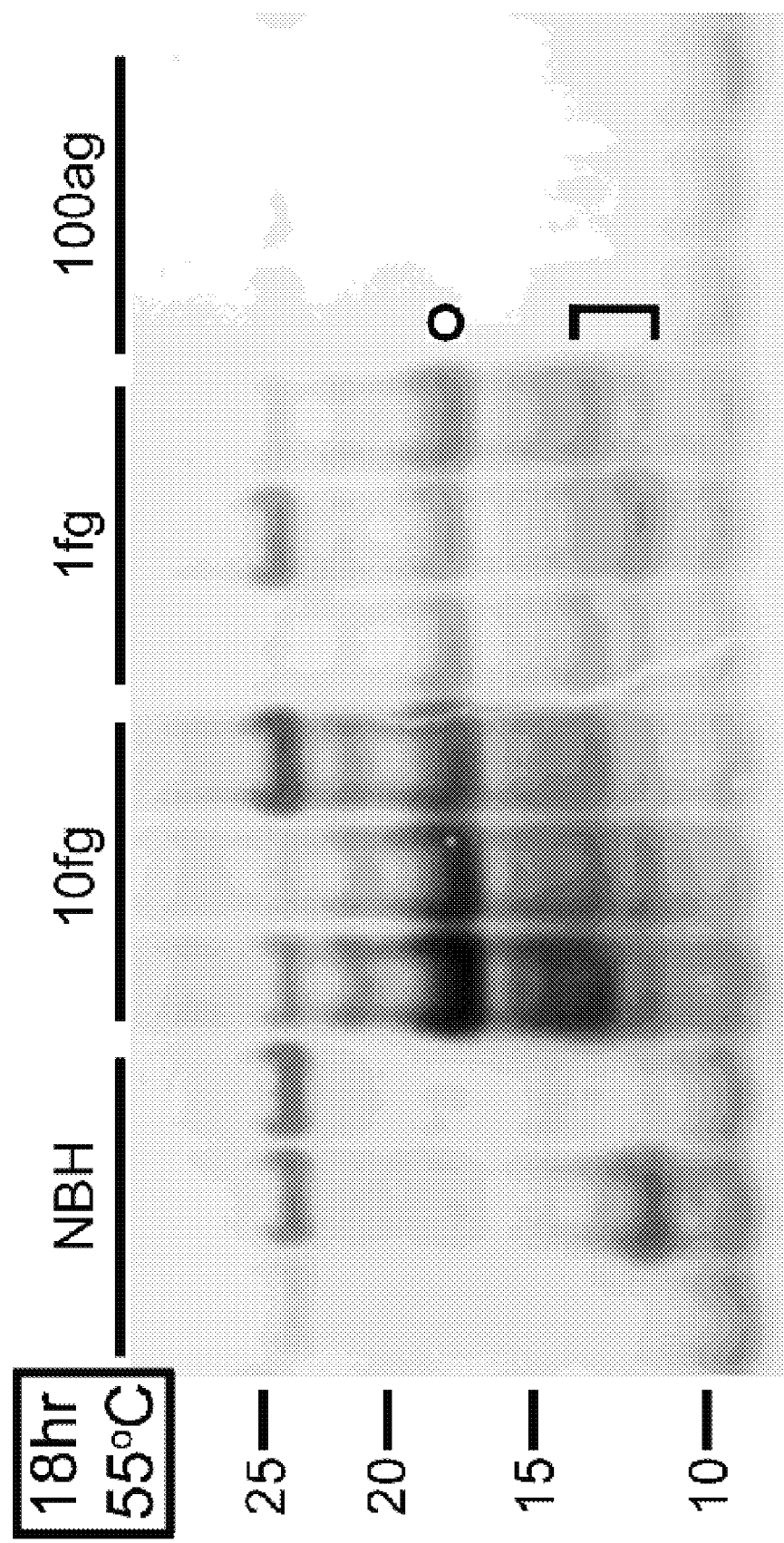
FIG. 19 is a digital image of a blot showing the sensitivity of an 18-hour QUIC reaction at 55° C. QUIC reactions were seeded with scrapie brain homogenates (diluted in N2) containing the designated amount of PrP$^{Sc}$ or normal brain homogenate (NBH) at the dilution used for the 10-fg scrapie brain homogenate sample. Reaction buffer constituents, PK-digestion conditions, and immunoblotting were as described in the legend to FIG. 12. The positions of molecular mass markers are designated in kDa on the left. The open circles designate the position of the 17 kDa band and the bracket the 10-13 kDa bands.
Figure 20:
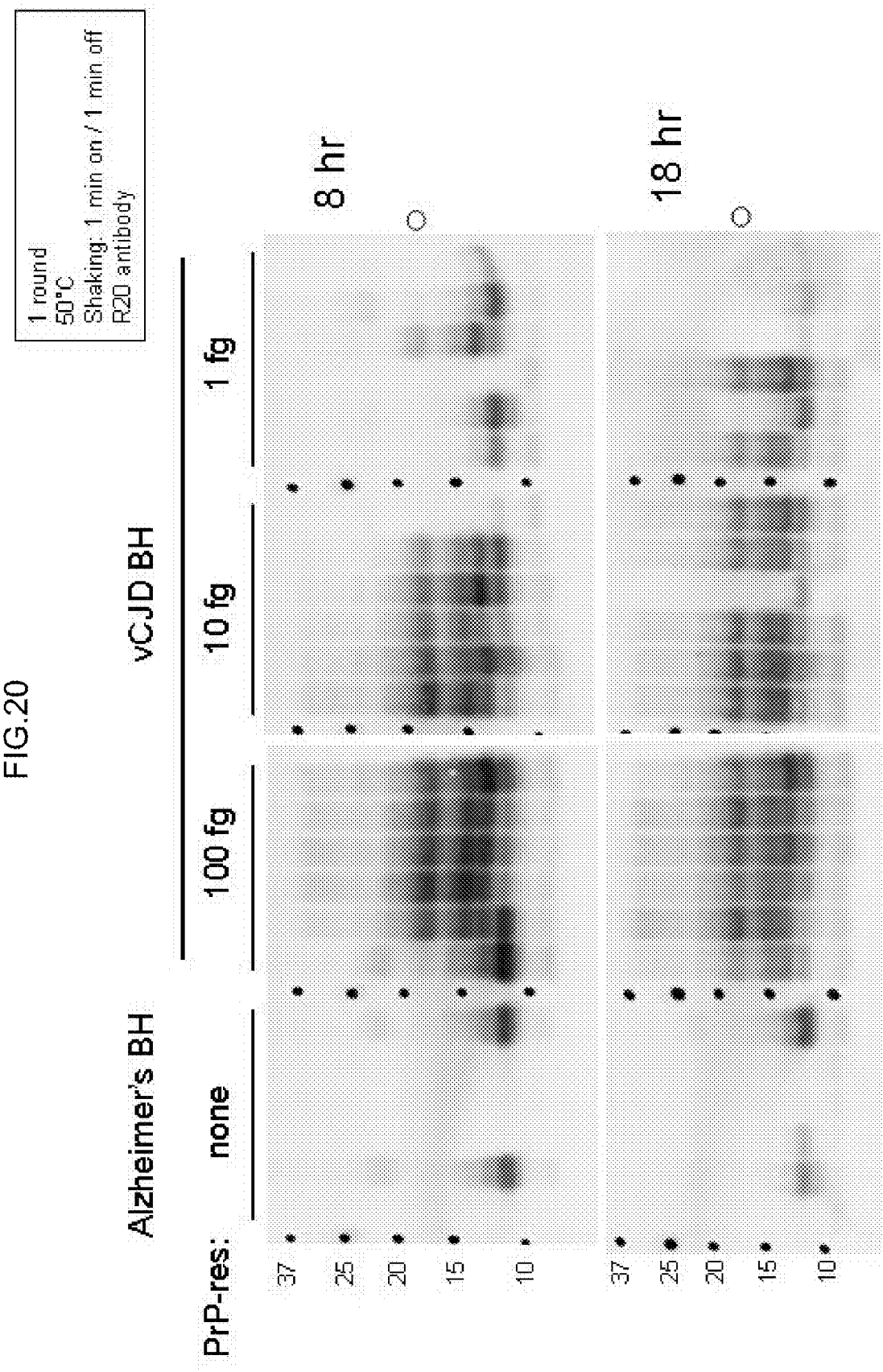
FIG. 20 shows blots from a QUIC reaction seeded either with dilutions of brain homogenate from a variant CJD patient containing 100 fg, 10 fg, or 1 fg of PrP-res or, as a negative control, a dilution of a non-CJD human brain homogenate (from an Alzheimer's disease patient) equivalent to the 100-fg vCJD brain homogenate dilution. The recombinant PrP substrate in these reactions was the Syrian hamster PrP sequence (residues 23-231). This was a single-round reaction at 50° C. for either 8 hours (top blots) or 18 hours (bottom blots). The primary antibody used to detect the rPrP-res[CJD] reaction products was monoclonal Ab 3F4, which has an epitope within residues 106-112, and thus, is only expected to detect the 17-kDa rPrP-res[CJD] product and not the smaller bands that are detected by more C-terminally reactive antibodies. Six separate reactions were performed with each type or dilution of seed and the number of rPrP-res[CJD]-positive reactions per 6 replicates is indicated below each set of replicates on the blots.

Testing of QUIC reaction conditions revealed that periodic shaking enhanced PrP$^{Sc}$ seeded conversion of hamster rPrP-sen (residues 23-231) into PK-resistant conversion products [rPrP-res(Sc), where (Sc) refers to seeding by PrP$^{Sc}$] (FIG. 10) which, consistent with our previous observations with sonicated (rPrP-PMCA) reactions 7, produced prominent rPrP-res(Sc) bands of 17, 13, 12 and 11 kDa. Periodic shaking can therefore substitute for sonication in promoting rPrP-res(Sc) formation. The rPrP-res(Sc) generation was further improved by varying rPrP-sen concentration, reaction volume (FIG. 10), reaction time (FIG. 11), number of serial reactions (FIG. 12), temperature (FIG. 18), and shaking cycle (FIG. 19). Furthermore, addition of the detergent N-lauroyl sarcosine to the PK-digestion buffer improved the ratio of the 17-kDa rPrP-res$^{(Sc)}$ band to the smaller bands (FIG. 20). In QUIC reactions performed at 45° C., rPrP-res$^{(Sc)}$ formed in triplicate 1-round 46-h QUIC reactions seeded with ≧100-ag of PrP$^{Sc}$ (FIG. 14). In contrast, 21 negative control reactions seeded with comparable dilutions of normal brain homogenate or buffer alone produced no rPrP-res (FIG. 14). Results similar to those in FIG. 1 were obtained in an identical repeat experiment done in triplicate. When products of PrPSc-seeded reactions were diluted 1000-fold into fresh rPrP-sen to seed the subsequent reaction rounds, strong propagation of rPrP-res$^{(Sc)}$ through at least 4 serial reactions was observed. Under some conditions, such as with multiple serial 48-h reaction rounds at 45° C., reactions seeded with only normal brain homogenate occasionally generated a spontaneous product, rPrP-res$^{(spon)}$, indicated by a set of ≦13 kDa PK-resistant bands. The latter were similar to those observed previously in unseeded rPrP-PMCA assays and were clearly distinct from the overall rPrP-res(Sc) banding profile. Hence longer amplification assays, although they can detect very small amounts of target in the sample, form more of the unwanted rPrP-res$^{(spon)}$ product that competes with the desired amplification reaction and that product could be confused with rPrP-res$^{(Sc)}$ under some conditions.

Consistent with previous findings with rPrP PMCA reactions, we found that when blots of PrPSc-seeded reaction products were probed with an antibody to PrP residues 95-103 (D13)$_8$, the 17-kDa rPrP-res(Sc) band was stained preferentially (FIG. 10). This result indicated that the smaller 11-13 kDa bands that reacted with the C-terminal antibody R20 were C-terminal fragments lacking the N-terminal portion of PrP containing the D13 epitope. Elevation of QUIC reaction temperatures accelerated rPrP-res$^{(Sc)}$ formation (FIG. 18). At 55° C., rPrP-res$^{(Sc)}$ was detected in 8-hour reactions seeded with as little as 10 fg PrPSc (~one intracerebral infectious dose) (FIG. 18), while 1 fg could be detected in triplicate 18-hours reactions (FIG. 21). At 65° C., 100 fg PrP$^{Sc}$ seed could be detected in only 4-hours (FIG. 18). However, at 65° C., there was also more rapid formation of rPrP-res$^{(spon)}$ in reactions seeded with normal brain homogenate, which was apparent in all three reactions at 18 hours. Overall, there is a tradeoff between sensitivity and speed in QUIC assays and at any given temperature, the longer the total reaction times the greater the likelihood of spontaneous (unseeded) rPrP-res formation. However, spontaneous rPrP-res has usually produced patterns of PK-resistant bands that are distinct from rPrP-res$^{(Sc)}$. Interestingly, the patterns can be altered when reaction conditions were pushed to both higher temperatures and relatively long reaction times. The QUIC reaction conditions can be altered to reduce the production of spontaneous rPrP-res that appears similar to rPrP-res$^{(Sc)}$ according to the rPrP-sen sequence used in the QUIC reaction.

Cerebral spinal fluid (CSF) is a more accessible biopsy specimen than brain, hence QUIC seeding activity was evaluated in CSF samples collected from hamsters showing clinical signs of scrapie or uninfected control animals. After one 48-h round (at 37° C.), no rHaPrP-res was seen in the control reactions. However, all of the scrapie CSF reactions produced the distinctive rHaPrP res(Sc) banding pattern albeit with variable intensities (FIG. 17). After a second serial QUIC reaction, the control reactions still lacked rPrP-res, while the reactions seeded with scrapie CSF produced strong rHaPrP-res(Sc) patterns of similar intensity. Similar 2-round QUIC reactions showed that CSF samples from 10 additional uninfected control hamsters produced no rHaPrP-res bands while two of the original scrapie-positive CSF samples again produced strong rHaPrP-res(Sc) patterns (data not shown). Thus, QUIC reactions seeded with CSF samples can discriminate between uninfected and scrapie-affected hamsters.

Figure 15A:
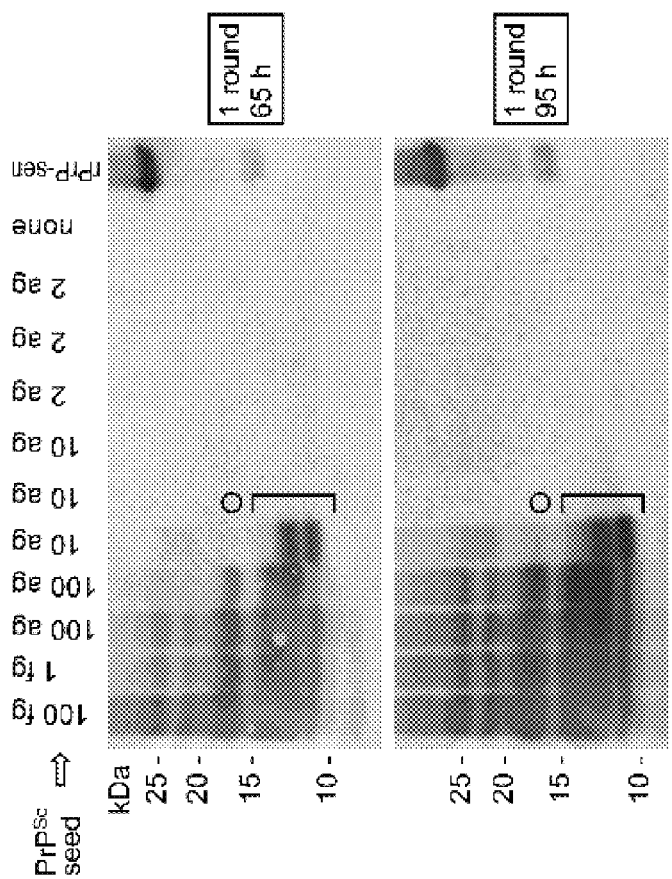
Figure 15B:
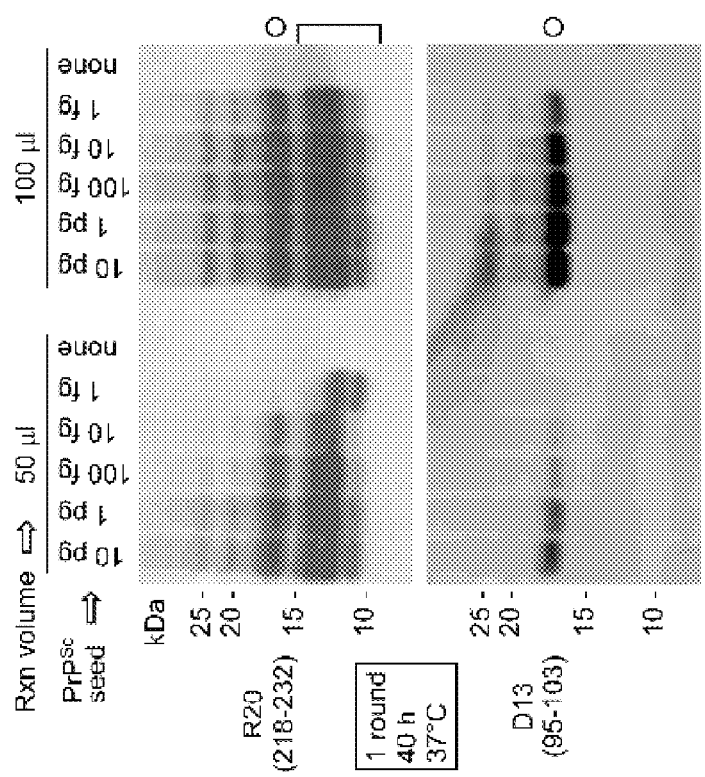

A QUIC assay provides a simple alternative to sonication for supporting an ultrasensitive prion assay. The delivery of vibrational energy to samples does not vary substantially with tube position, tube construction, probe age, bath volume, and the redistribution of samples as often occurs within the tubes with sonication-induced atomization and condensation. The 45° C. single-round QUIC reaction is virtually as sensitive as 2-round sonicated rPrP-PMCA reactions of similar overall duration. The QUIC reaction conditions are also less permissive of spontaneous unseeded rPrP-res$^{(spon)}$ formation. Significantly, elevated reaction temperatures can greatly accelerate QUIC reactions, allowing detection of a lethal dose of 263K scrapie (i.c.) in <1 day (See FIGS. 15 and 18). The relative speed, simplicity and ease of duplication of the QUIC reaction conditions offers major practical advantages.

It is also possible to vary the shaking cycle to obtain surprisingly superior results in the QUIC assay. For example, the ratio of time spent shaking to time at rest can be varied to improve the outcome of the assay. In some examples, the ratio of time shaking:time at rest can vary from 1:15 to 1:1, such as 1:11 to 1:1. In particular examples, it has been found that substantially equal periods of shaking and rest provide particularly good results. For example, a shaking cycle of 60 seconds on and 60 seconds off works better than the 10 seconds on, 110 seconds off cycle for the hamster scrapie QUIC assay using rPrP-sen 23-231.

The total length of a cycle (time spent shaking plus time spent not shaking) may be less than about an hour, or even less than 5 minutes, for example less then 3 minutes, such as 2 minutes (120 seconds) or less. In particular examples, the total cycle is more than 60 seconds, such as 60-180 seconds, or 60-120 seconds. The shaking cycle can be optimized with regard to the rPrP-sen sequence used in the QUIC reaction.

Example 9

Exemplary Protocol for rPrP-PCMA

This Example provides an exemplary step-by-step protocol for rPrP-PMCA using hamster 263K scrapie seed and hamster rPrP-sen substrate. Although specific exemplary protocols are provided, one will appreciate that other similar protocols can be used.
I. Sample and Substrate Preparation
  A. Preparation of Normal or 263K Scrapie Brain Homogenates (NBH And ScBH, Respectively):
  Reaction tubes were 0.2 ml thin wall PCR tube strips (Nalge Nunc International 248161). Sample and substrate preparation was carried out as follows:
    1) Perfuse normal or scrapie-affected Syrian golden hamsters with ice cold 1×PBS-EDTA:

| | |
|---|---|
| NaCl | 8 g |
| KCl | 0.2 g |
| Na$_2$PO$_4$ | 1.44 g |
| KH$_2$PO$_4$ | 0.24 g |
| +5 mM EDTA | |
| pH to 7.4 with HCl | |
| QS to 1 L | |

2) Extract hamster brain with clean tools and flash freeze with liquid nitrogen
    3) Store perfused brains at −80° C.
    4) Dounce homogenize perfused brains, on ice, in conversion buffer (10% weight to volume):

| | |
|---|---|
| 1X PBS-EDTA from step #1 (but 1 mM EDTA) | 19.3 ml |
| 5 M NaCl | 0.6 ml |
| Triton X-100 | 0.1 ml |
| Complete Protease Inhibitor Cocktail, EDTA free (Roche 11836170001) | 1 tablet/20 mls |

5) Spin NBH at 2000 g for 2 minutes to partially clarify; collect supernatant
    6) Prepare 1 ml 10% NBH aliquots and flash freeze in liquid nitrogen
    7) Store aliquots at −80° C.
  B. Preparation of Hamster rPrP-sen:
Materials:
  Approximately a 2 g cell pellet of rHaPrP 23-231 (yield from ¼$^{th}$ of 1 L LB-Miller growth medium)
  BugBuster™ and lysonase bioprocessing reagent (EMD Biosciences)
  8M Guanidine in water
  Ni-NTA Superflow resin (Qiagen)
  Denaturing Buffer: 100 mM sodium phosphate, 10 mM Tris, 6M Guanidine, pH 8.0
  Refolding Buffer: 100 mM sodium phosphate, 10 mM Tris, pH 8.0
  Elution Buffer: 500 mM imidazole, 10 mM Tris, 100 mM Phosphate pH 5.8-6.0
  Dialysis Buffer: 10 mM sodium phosphate, pH 6.5 (diluted from 1M stock at pH 5.8)
  AKTA Explorer 10 liquid chromatography system
Bacterial Cell Lysis:
  200 µL of lysonase bioprocessing reagent and 1 Complete protease inhibitor tablet (Roche) were mixed into 50 mL of BugBuster™ and stirred on ice. The frozen cell pellet was sliced with a razor blade and added portionwise into the BugBuster™ solution. Stirring was performed at 0° C. while breaking up larger pieces with a spatula. Sonication was performed for 15 second intervals with a Misonix ultrasonic cell disrupter (power level 10) periodically over the course of ~30 minutes until the mixture was relatively homogeneous and became milky. Centrifugation was carried out at 10,000 g (JA 12 rotor, Beckman Centrifuge) for 10 minutes. Pellets were washed twice with 20 mL BugBuster™ diluted 10-fold with water, dispersed with pipette-aid, and centrifuged at 10,000 g for 10 minutes. The washing, dispersing and centrifuging was repeated, and the inclusion body pellet was stored at −20° C.

Purification was carried out by filling a 2×2 L graduated cylinder with 10 mM phosphate dialysis buffer diluted from 1 M stock at pH 5.8. All chromatography buffers were filtered prior to use. The inclusion body pellet was dissolved into 8 mL of 8 M guanidine and mixed by pipetting up and down with a transfer pipette. The mixture was transferred into 2 mL flip cap tubes and centrifuged at 8,000 g for 10 minutes. Filter and wash fresh Ni-NTA Superflow resin (Qiagen) exhaustively with water. Store dry at 4° C. Then 18 g of Ni-NTA resin was weighed into a clean beaker and the resin pre-equilibrated with 30-40 mL of denaturing buffer by stirring at room temperature. Supernatant was added from 2 mL flip cap tubes to the resin and the tube discarded with the pellet. Stirring was carried out for an additional 30 minutes. The resin slurry was poured into an empty XK16/20 column and a column attached with impregnated resin to an AKTA Explorer 10 (GE/Amersham) according to the manufacturer's directions. The column outlet was detached and the flow-though collected directly in a graduated cylinder. The flow-through can either be discarded or saved for future use, as there is typically excess PrP in this solution.

A linear gradient was run with 0-100% refold buffer at 0.75 mL/min over 5-6 hours, followed by 100% refolding buffer for 30-60 minutes at 1 mL/min. The pump were rinsed with distilled water, and then Line A equipped with refold buffer and Line B with elution buffer. The bottom of column was reattached to the UV and conductivity detector. Elution buffer was run through line B and the UV autozero detector set at 280 nm. The refolded peptide was eluted at 2 mL/min for 20 minutes. After a brief forerun, the major fraction was collected at UV 280 as one portion in a 250 mL graduated cylinder prefilled with 50 mL pure water. The protein was diluted with water to 150 mL, then sterile filtered with a 150 mL filter unit. An expected concentration of ~0.1-0.15 mg/mL is determined by $A_{280}$. The protein was dialyzed (Snakeskin dialysis tubing MWCO 7000) overnight in dialysis buffer, and the protein transferred into fresh dialysis buffer for 1 hour. If there was any turbidity at this point, immediate sterile filtration was performed. The peptide was analyzed for purity by SDS-PAGE, Western blot, and MALDI, and the protein concentrated to ~0.4 mg/ml in 10 mM sodium phosphate buffer, pH 6.5, using an Amicon Ultracel –10k filter (15 ml capacity). Aliquots were flash frozen and stored at −80° C. Once thawed, it was kept at 4° C.

C. 4×PMCA Buffer
(Final composition: 0.2% SDS, 0.2% TritonX-100, 4×PBS)
10% SDS stock (20 µl/ml)
10% TritonX-100 stock (20 µl/ml)
10×PBS stock (400 µl/ml):

| | |
|---|---|
| $Na_2HPO_4 7H_2O$ | 26.8 g/L |
| $NaH_2PO_4 H_2O$ | 13.8 g/L |
| NaCl | 75.9 g/L |
| pH 6.9 | |
| $H_2O$ (560 µl/ml) | |

II. rPrP-PMCA Protocol:
A. 1$^{st}$ rPrP-PMCA Round was carried out according to this protocol:
1) Sonicator setup: Misonix 3000 with microplate (cup) horn accessory
2) Circulating water bath was set up at 39.4 degrees for cup horn, resulting in a temperature of 37 degrees in the cup horn.
3) 1 ml of 1×PMCA buffer was made up from 4× stock
4) Thawed aliquots of 10% NBH & 10% ScBH
5) Centrifuged 10% NBH at 1000 rcf for 5 minutes at 4° C. to remove large debris.
6) Made up 1 ml of 1% NBH by dilution into 1×PMCA buffer
7) Prepared 263K BH seed diluted in 1% NBH (see dilution series below)
 a) dilute 10% 263K BH 1:20 into 1% NBH (5 µl stock+9 µl 1% NBH)→500 pg/1 µl
 b) further dilute 1:10 (5 µl previous+45 µl 1% NBH)→50 pg/1 µl
 c) further dilute 1:10 (5 µl previous+45 µl 1% NBH)→5 pg/1 µl
 d) further dilute 1:10 (5 µl previous+45 µl 1% NBH)→500 fg/1 µl
 e) further dilute 1:10 (5 µl previous+45 µl 1% NBH)→50 fg/1 µl
 f) further dilute 1:10 (5 µl previous+45 µl 1% NBH)→5 fg/1 µl
 g) further dilute 1:10 (5 µl previous+45 µl 1% NBH)→500 ag/1 µl
 h) further dilute 1:10 (5 µl previous+45 µl 1% NBH)→50 ag/1 µl
 i) further dilute 1:10 (5 µl previous+45 µl 1% NBH)→5 ag/1 µl
 j) further dilute 1:10 (5 µl previous+45 µl 1% NBH)→0.5 ag/1 µl
  (1 fg=2 µl of g)
  (100 ag=2 µl of h)
  (30 ag=6 µl of i)
  (10 ag=2 µl of i)
8) Prepared reaction mix in reaction tubes as described above (adding in the order specified)

| 1$^{st}$ Round Reaction Mix: | |
|---|---|
| 31.3 µl | H2O |
| 20 µl | 4X PMCA buffer |
| 26.7 µl | rPrP-sen (to give a final concentration of 0.1 mg/ml) |
| 2 µl | ScBH seed diluted in 1% NBH |
| 80 µl | total volume |

9) When adding the rPrP-sen and then the seed material to the 1×PMCA buffer in the reaction mix, mixing was performed by pipetting up and down gently without vortexing. The reaction tubes were capped but without vortexing. Place tube strips were placed in a floating 96 well rack in the sonicator cup horn, cover cup with plastic wrap to reduce splashes and evaporation.
10) Started sonicator program (typical: 40 second intermittent sonication at power setting #10, 16 minute total sonication time, 59 minute 20 second incubations between each sonication, 24 hour total cycle time)
11) Following sonication cycle (24 hours), turned off sonicator and removed tube strips.
12) Spun the tube strips briefly to bring solution down out of the caps.
13) Removed aliquot for 2$^{nd}$ rPrP-PMCA round and/or prepared for methanol precipitation and immunoblot analysis (see below).

B. 2nd PMCA Round:
1) Prepare reaction mix in fresh reaction tube strips as described for 1$^{st}$ round above. The sample was gently vortexed to evenly suspend just prior to transferring volume. Following the addition of rPrP-sen, mixing was performed by pipetting up and down.

| 2nd Round Reaction Mix: | |
|---|---|
| 30 µl | H₂O |
| 18 µl | 4X PMCA buffer |
| 24 µl | rPrP-sen (a volume to give a final concentration of 0.1 mg/ml) |
| 8 µl | reaction aliquot from first round rPrP-PMCA |

2) The reaction tube strips were capped, and the tube strips placed in the floating rack in the sonicator cup horn. The cup horn was covered with plastic wrap to reduce splashes and evaporation. The sonicator program was started (typical: 40 second intermittent sonication at #10, 16 minute total sonication time, 59 minute 20 second incubations between each sonication, 24 hours total cycle time). Following the sonication cycle (24 hours), the sonicator was turned off and tube strips removed. The tube strips were quick spun to bring solution down out of the caps, and the samples were methanol precipitated prior to further analysis (see below)

C. PK-Digestion and SDS-PAGE Sample Preparation:
(Note: In the following example, the methanol precipitation-associated steps 7-11 can often be omitted, in which case the products of step 6 are mixed directly with more concentrated SDS-PAGE sample buffer)

1) Prepared 0.1% SDS in 1×PBS

2) Transferred 5 μl of each sample to a clean screw cap tube. (vortexed sample to evenly suspend just prior to transferring volume)

3) Added 19 μl 0.1% SDS in PBS

4) Added 1 μl 75 μg proteinase K (PK)/ml (final concentration will be 3 μg PK/ml) PK storage buffer PK storage buffer:

50% glycerol 1 mM CaCl2

50 M Tris, pH 8.5

5) Incubated at 37 degrees for 1 hour

6) Added 1 μl of 0.1M PEFABLOC® (4-(2-Aminoethyl)-benzensulfonyl fluoride (Roche), vortex and place on ice 7) Added 4 μl of thyroglobulin (5 mg/ml), vortex and keep on ice 8) Added 120 μl (4 volumes) of cold methanol, vortexed and kept on ice 9) Stored at −20 degrees for ≧1 hour 10) Spun at 20800 rcf in the Eppendorf 5417R centrifuge at 4 degrees for 30 minutes 11) Aspirated off supes and leave caps off to air dry samples 12) Added 15 μl 1×SDS-PAGE sample buffer containing 4M Urea to each tube 13) Vortexed samples in SDS-PAGE sample buffer for 1 minute 14) Boiled tubes for 10 minutes 15) Loaded sample onto 10% NUPAGE® (polyacrylamide) gel & run D. Immunoblotting:

Wet transfer was performed using Towbin transfer buffer, Immobilon-P Blotting sandwiches (Millipore IPSN07852) and BioRad Mini Trans-blot for 1 hour at 0.3 amps constant. The primary antibodies used were R20 (*J. Virol.* 65, 6597-6603 (1991)) at 1:30,000 or D13 (*Nature* 412, 739-743 (2001)) at 1:10,000. The secondary antibodies were anti-rabbit or anti-human AP conjugated, as appropriate. Immunostaining was visualized by Attophos AP Fluorescent Substrate System (Promega) according to the manufacturer's recommendations.

III. QUIC Protocol

A. $1^{st}$ QUIC Round:

1 ml of 1×PMCA buffer was made up from 4× stock, and aliquots of 10% NBH & 10% ScBH were thawed. Centrifuged 10% NBH at 2000 rcf for 2 minutes at 4° C. to remove large debris. Made up 1 ml of 1% NBH by dilution into 1×PMCA buffer and prepared 263K BH seed diluted in 1% NBH (see dilution series below).

263K BH Seed Dilution Series:

a) dilute 10% 263K BH 1:20 into 1% NBH (5 μl stock+95 μl 1% NBH)→500 pg/1 μl b) further dilute 1:10 (5 μl previous+45 μl 1% NBH)→50 pg/1 μl c) further dilute 1:10 (5 μl previous+45 μl 1% NBH)→5 pg/1 μl d) further dilute 1:10 (5 μl previous+45 μl 1% NBH)→500 fg/1 μl e) further dilute 1:10 (5 μl previous+45 μl 1% NBH)→50 fg/1 μl f) further dilute 1:10 (5 μl previous+45 μl 1% NBH)→5 fg/1 μl g) further dilute 1:10 (5 μl previous+45 μl 1% NBH)→500 ag/1 μl h) further dilute 1:10 (5 μl previous+45 μl 1% NBH)→50 ag/1 μl i) further dilute 1:10 (5 μl previous+45 μl 1% NBH)→5 ag/1 μl j) further dilute 1:10 (5 μl previous+45 μl 1% NBH)→0.5 ag/1 μl (1 fg=2 μl of g)

(100 ag=2 μl of h)

(30 ag=6 μl of i)

(10 ag=2 μl of i)

Prepared reaction mix in reaction tubes as described above (add in the order specified).

| $1^{st}$ Round Reaction Mix: | |
|---|---|
| 47.4 μl | H2O |
| 25 μl | 4X PMCA buffer |
| 25.6 μl | rPrP-sen |
| 2 μl | ScBH seed diluted in 1% NBH |
| 100 μl | total volume |

Adjusted $H_2O$ and rPrP-sen volumes to give a final rPrP-sen concentration of 0.1 mg/ml. When adding the rPrP-sen and then the seed material to the 1×PMCA buffer in the reaction mix, mixing was performed by pipetting up and down gently without vortexing. The reaction tubes were capped but not vortexed. The tubes were placed in Eppendorf Thermomixer R with 24×0.5 ml tube block and incubated in Thermomixer R for the desired time at 37° C., alternating between 10 seconds of shaking at 1500 rpm and no shaking for 110 seconds, unless designated otherwise. The tubes were spun to bring any solution down out of the caps. An aliquot was removed for $2^{nd}$ QUIC round and/or prepared for PK digestion, methanol precipitation and immunoblot analysis (see below).

B. 2nd QUIC Round:

The reaction mix was prepared in fresh reaction tubes similar to $1^{st}$ round above. The sample tubes were gently vortexed to evenly suspend any pellet just prior to transferring volume to the $2^{nd}$ round reaction tube. Following the addition of rPrP-sen, mixed by pipetting up and down.

| $2^{nd}$ Round Reaction Mix: | |
|---|---|
| 43.5 μl | H2O |
| 22.5 μl | 4X PMCA buffer |
| 24 μl | rPrP-sen |
| 10 μl | sample volume from $1^{st}$ round reaction |
| 100 μl | total volume |

The $H_2O$ and rPrP-sen volumes were adjusted to give a final rPrP-sen concentration of 0.1 mg/ml. When adding the rPrP-sen and then the seed material to the 1×PMCA buffer in the reaction mix, mixing was performed by pipetting up and down gently without vortexing. The seed was diluted in 1% NBH as described in the 1st QUIC round, and the remainder of the method performed as in 1st QUIC round.

PK-Digestion and SDS-PAGE Sample Preparation:

(Note: In the following, the methanol precipitation-associated steps 7-11 can often be omitted, in which case the products of step 6 is mixed directly with more concentrated SDS-PAGE sample buffer)

1) Prepared 0.1% SDS in 1×PBS
2) Transferred 10 µl of each sample to a clean screw cap tube and vortexed sample to evenly suspend any pellet just prior to transferring volume
3) Added 38 µl 0.1% SDS in PBS
4) Added 2 µl 75 µg proteinase K (PK)/ml (final concentration will be 3 µg PK/ml) PK storage buffer (50% glycerol, 1 mM $CaCl_2$, 50 mM Tris, pH 8.5)
5) Incubated at 37 degrees for 1 hour
6) Added 1 µl of 0.1M PEFABLOC® (4-(2-Aminoethyl)-benzensulfonyl fluoride (Roche), vortexed and placed on ice
7) Added 4 µl of thyroglobulin (5 mg/ml), vortexed and kept on ice
8) Added 120 µl (4 volumes) of cold methanol, vortexed and kept on ice
9) Stored at −20 degrees for ≧1 hour
10) Spun at 20800 rcf in Eppendorf 5417R centrifuge at 4 degrees for 30 minutes
11) Aspirated off supernatant and left caps off to air dry samples
12) Added 15 µl 1×SDS-PAGE sample buffer containing 4M Urea to each tube
13) Vortexed samples in SDS-PAGE sample buffer for 1 minute
14) Boiled tubes for 10 minutes
15) Loaded sample onto 10% NUPAGE® (polyacrylamide) gel & run Immunoblotting:

Wet transferred using Towbin transfer buffer, Immobilon-P Blotting sandwiches (Millipore IPSN07852) and BioRad Mini Trans-blot for 1 hour at 0.3 amps constant.

Primary antibodies: R20 [*J. Virol.* 65, 6597-6603 (1991)] at 1:30,000 or D13 [*Nature* 412, 739-743 (2001)] at 1:10,000.

Secondary antibodies-anti-rabbit or anti-human AP conjugated, as appropriate.

Immunostaining was visualized by ATTOPHOS® AP Fluorescent Substrate (2'-[2-benzothiazoyl]-6'-hydroxybenzothiazole phosphate [BBTP]) System (Promega) according to the manufacturer's recommendations.

Example 10

Amplification of PrP-res from a Variant-CJD (vCJD) Patient

FIG. 20 shows Western blots from a QUIC reaction seeded either with dilutions of a brain homogenate (BH) from human variant CJD patient (vCJD BH) containing 100 fg, 10 fg, or 1 fg of PrP-res or, as a negative control, a dilution of a non-CJD human brain homogenate (from an Alzheimer's patient; AD-BH) equivalent to the 100-fg vCJD brain dilution. The recombinant PrP (rPrP-sen) substrate in these reactions was the Syrian hamster PrP sequence (residues 23-231). A single-round reaction was performed at 50° C. for either 8 hours (top blots) or 18 hours (bottom blots). The primary antiserum used to detect the rPrP-res[CJD] reaction products was R20. Six separate reactions were performed with each type or dilution of seed and the number of rHaPrP-res$^{(vCJD)}$-positive reactions per 6 replicates is indicated below each set of replicates on the blots.

vCJD-BH dilutions containing a nominal 100 fg of PrP-res produced clear rHaPrP-res$^{(vCJD)}$ patterns in five out of six 8-h reactions, and in 6/6 18-hour cross-species QUIC reactions. Samples with 10 fg PrP-res were positive for rHaPrP-res$^{(vCJD)}$ in 5/6 reactions of both 8 and 18 h. Samples with 1 fg PrP-res were rHaPrP-res$^{(vCJD)}$-positive in 1/6 8-h and 2/6 18-h reactions. At the same time, the AD-BH gave no rHaPrP-res$^{(vCJD)}$-positive reactions with either reaction time. Although it is unknown how much PrP-res is required for an infectious dose, it is known that a lethal intacerebral dose of hamster 263K scrapie usually corresponds to 1-10 fg of PrP$^{Sc}$. Thus, this cross-species QUIC reaction can detect quantities of vCJD PrP-res (as little at 10 fg and even as low as 1 fg) that approximate that of an infectious dose of scrapie by the most efficient intracerebral route.

The assay was carried out in 0.5 ml conical microcentrifuge tubes with screw caps (Fisher $O_2$-681-334). Brains were homogenized in conversion buffer (10% weight to volume):

| | |
|---|---|
| 1X PBS-EDTA from step #1 (but 1 mM EDTA) | 19.3 ml |
| 5M NaCl | 0.6 ml |
| Triton X-100 | 0.1 ml |
| Complete Protease Inhibitor Cocktail, EDTA free (Roche 11836170001) | 1 tablet/20 mls |

Brain homogenates (BH) were spun spin at 2000 g for 2 minutes to partially clarify; supernatant was collected and 1 ml 10% AD-BH and vCJD-BH aliquots were prepared and frozen for storage at −80° C.

Hamster rPrP-sen was prepared as in Example 8, as were bacterial cell lysis and purification. The same 4×PMCA buffer was used as in Example 8. The QUIC protocol was carried out by making up a working stock of 0.1% SDS in 1×PBS, thawing aliquots of 10% AD-BH & 10% vCJD-BH, making up 1 ml of 1×N2 supplement (Invitrogen) by dilution into 0.1% SDS/PBS. The AD-BH & vCJD-BH seed dilutions in 1×N2 were carried out as follows:

7.1 ul 10% AD-BH or 10% vCJD-BH+2.9 ul 1×N2→1 ug/2 ul further dilute 1:10 (5 ul previous+45 ul 1×N2)→100 pg/2 ul further dilute 1:10 (5 ul previous+45 ul 1×N2)→10 pg/2 ul further dilute 1:10 (5 ul previous+45 ul 1×N2)→1 pg/2 ul further dilute 1:10 (5 ul previous+45 ul 1×N2)→100 fg/2 ul further dilute 1:10 (5 ul previous+45 ul 1×N2)→10 fg/2 ul further dilute 1:10 (5 ul previous+45 ul 1×N2)→1 fg/2 ul Recombinant PrP was filtered with a 100 kD microtube filter (PALL) by spinning at 3000×g for 12 min, and diluted 1:10 in 0.1% SDS/PBS and measured spectrometrically for optical density at 280 nm.

[Protein] mg/mL=(280 nm reading/PrP Extinction Coefficient (2.6))*Dilution Factor=X mg/mL Want 0.1 mg/mL rPrP in 100 uL reaction=10 ug/X=Y uL rPrP per reaction Amount of water in reaction=100−Y−2−25=Z uL Water per reaction The reaction mix was prepared in reaction tubes as described above (add in the order specified).

| 1ˢᵗ Round Reaction Mix: | | |
|---|---|---|
| Z ul | H₂O | 13 ul |
| 25 ul | 4X QUIC buffer | 25 ul |
| 2 ul | ScBH seed diluted in 1% NBH | 2 ul |
| Y ul | rPrP-sen | 60 ul |
| | | 100 ul total volume |

The first three components were vortexed for 5 s prior to adding the rPrP-sen, and the rPrP-sen was added gently, as not to create bubbles. The reaction tubes were capped but not vortexed. The tubes were placed in an Eppendorf Thermomixer™ with 24×0.5 ml tube block and incubated for the designated time (either 8 or 18 hrs) at 50° C., alternating between 60 seconds of shaking at 1500 rpm and no shaking for 60 sec. The Thermomixer R is programmed to adjust to 4° C. following the 50° C. time. Spinning of the tubes was performed to recover any solution from the caps.

PK-digestion and SDS-PAGE sample preparation were performed by preparing 1% N-lauroylsarcosine sodium salt (sarkosyl) in 1×PBS, and diluting stock proteinase K (PK) (10 mg/ml) 100-fold into PK storage buffer (final concentration will be 100 ug PK/ml).

PK storage buffer:
50% glycerol
1 mM $CaCl_2$
50 mM Tris, pH 8.5

Further diluted 100 μg PK/ml solution above 1 to 5 in 1% Sarkosyl/PBS (25 ul+100 ul 1% Sarkosyl/PBS), transferred 5 μl of PK/Sarkosyl solution to a fresh set of tube, and vortexed QUIC sample tubes evenly to suspend any pellet just prior to transferring volume, then transferred 10 ul to individual tubes containing PK/Sarkosyl. Incubation was performed at 37° C. for 1 hour, then 15 μl 2×SDS-PAGE sample buffer containing 4M Urea was added to each tube. The samples were vortexed in SDS-PAGE sample buffer for 1 minute, the tubes boiled for 10 minutes, and the samples subjected to zip spinning and loaded onto 10% NuPAGE gel (Invitrogen) with MES buffer (Invitrogen).

Immunoblotting was performed by pre-incubating membranes in methanol for 3 minutes to wet the PVDF membrane, pouring off the methanol and adding Towbin buffer to the VDF membrane. Dry transfer was performed using Invitrogen iGel System and Immobilon-P PVDF membrane (Millipore IPSN07852) for 7 minutes. The membrane was blocked in 5% Milk/TBST at room temperature for 30 minutes. It was exposed to primary antibody (R20 at 1:10,000 (2 uL/20 mL 5% Milk/TBST) for 30 min at room temperature) then washed 3× in ~30 mL TBST (500 uL Tween 20/1 L 1×TBS) for 5 minutes per wash. The secondary antibody was Goat anti-rabbit-AP conjugate (1:10,000 in 5% milk/TBST or 2 uL/20 mL) (Jackson) for 30 minutes). Washing was performed 3× in TBST for 5 minutes per wash. Then 1.5 mL Attophos AP (alkaline phosphatase) Fluorescent Substrate System (Promega) was added to the plastic container and gel placed face down onto it for ~4 minutes, following which the gel was removed and left on its edge to dry. The gel was visualized on Storm system (Amersham).

Example 11

Amplification of PrP from Sheep and Cows

Sheep with nervous disorders resembling those of a scrapie infection are purchased or donated. In some cases, sheep are diagnosed with scrapie by histopathological and immunohistochemical examination of the brain. If necropsy is performed, it is performed within 36 hours after natural death or immediately after killing the animal by intravenous injection of sodium pentobarbital and exsanguination. The brain is removed from each sheep for scrapie diagnosis. Blood, serum, cerebral spinal fluid and/or brain tissue samples are obtained from each sheep.

Cows with nervous system disorders resembling those of bovine spongiform encephalitis are also tested. These animals can be "downers" or can exhibit less severe symptoms. In some cases, animals that appear healthy can be tested to determine that they are not infected.

The samples are used to seed the conversion of rPrP-sen to protease-resistant forms in reactions performed in 0.1% sodium dodecyl sulfate and 0.1% Triton X-100, in PBS at 37° C. in 0.5 ml tubes. Tube shaking is done at 1500 rpm in an Eppendorf Thermomixer R or by vortexing. Proteinase K digestions and immunoblotting were performed as described above.

For comparing PK-resistant QUIC reaction products, 24-hour unshaken reactions and reactions were shaken with or without 0.1 mm glass cell disruption beads (Scientific Industries). These reactions are seeded with 0.2 mg/ml hamster rPrP-sen, 0.2 mg/ml bovine rPrP-sen, or 0.2 mg/ml sheep rPrP-sen and a 50 μl reaction volume. The tubes are subjected to cycles of 2 minutes of shaking and 28 minutes without shaking. C-terminal antibody R20 is used for the immunoblot. The tubes are subjected to cycles of 10 seconds of shaking and 110 seconds without shaking. R20 was used for the immunoblot.

If needed 65-hour and 95-hour QUIC reactions are carried out as described above, and 0.2 mg/ml rPrP-sen, is used for 100-μl reaction volumes. Cycles of 10 seconds shaking and 110 seconds without shaking can be used.

In other examples, 48-hour reaction times are used with reduced detergent concentrations (0.05% SDS and 0.05% Triton X-100). For the second round, 10% of the volume of the first round reaction products are diluted into 9 volumes of reaction buffer containing fresh rPrP-sen. PK-digestions and immunoblotting using either R20 or D13 primary antibodies were performed as described above.

For seeding with CSF samples, aliquots (2 μl) of CSF are used to seed QUIC reactions using the conditions, and immunoblots are carried out using the PK-digested products of the first 48-hour round. Ten percent of each first round reaction volume is used to seed a second 48-hour round of QUIC. Antibodies R20 and D13 are used for the immunoblots.

The foregoing examples provide specific examples of methods for carrying out the disclosed assay. In view of the many possible embodiments to which the principles of the disclosed assay can be applied, it should be recognized that the illustrated embodiments should not be taken as a limitation on the scope of the disclosure. Rather, the scope of the disclosure is defined by the following claims. We therefore claim all that comes within the scope and spirit of these claims.

We claim:

1. A method for detecting protease resistant prion protein (PrP-res) in a sample comprising:
   (a) mixing the sample with purified recombinant protease-sensitive prion protein (rPrP-sen) to make a reaction mix, wherein the rPrP-sen comprises the amino acid sequence set forth as SEQ ID NO: 3;
   (b) performing an amplification reaction comprising:
      (i) incubating the reaction mix at about 37° C. to permit coaggregation of the rPrP-sen with the PrP-res that may be present in the reaction mix, and maintaining incubation conditions that promote coaggregation of the rPrP-sen with the PrP-res and result in a conversion of the rPrP-sen to the recombinant protease resistant prion protein initiated by the presence of prions (rPrP-res$^{(Sc)}$), which is initiated by the presence of PrP-res in the sample, while inhibiting development of spontaneously occurring recombinant prion protein (rPrP-res$^{(spon)}$);
      (ii) agitating aggregates formed during step (i), in shaking cycles, wherein each shaking cycle of the shaking cycles comprises a period of rest and a period of shaking, and wherein the period of rest is about 30 seconds in length and the period of shaking is about 30 seconds in length, wherein agitating is performed for about 48 hours in the absence of sonication; and
   (c) detecting rPrP-res$^{(Sc)}$ in the reaction mix after agitating for about 48 hours as above, wherein detection of rPrP-res$^{(Sc)}$ in the reaction mix indicates that PrP-res was present in the sample.

2. The method of claim 1, wherein detecting the rPrP-res$^{(Sc)}$ comprises detecting rPrP-res$^{(Sc)}$ aggregates in the sample.

3. The method of claim 1, wherein the method further comprises digesting the reaction mix with proteinase K prior to detecting rPrP-res$^{(Sc)}$ in the reaction mix.

4. The method of claim 2, wherein detecting rPrP-res$^{(Sc)}$ comprises detecting rPrP-res$^{(Sc)}$ with an antibody that specifically binds to prion protein.

5. The method of claim 4, wherein the antibody is a polyclonal antibody.

6. The method of claim 1, wherein the rPrP-sen consists of:
   a) SEQ ID NO: 3.

7. The method of claim 1, wherein the sample is a tissue sample from an animal.

8. The method of claim 1, wherein prion can be detected in a sample containing no more than about 1 fg PrP-res.

9. The method of claim 1, wherein the method is a method of diagnosing a prion disease.

10. The method of claim 4, wherein the antibody is a monoclonal antibody.

11. The method of claim 1, wherein detecting rPrP-res$^{(Sc)}$ in the reaction mix comprises the use of a fluorescence assay.

12. A method for amplifying and detecting human protease resistant prion protein (PrP-res) in a sample comprising:
   (a) mixing the sample with the purified recombinant human protease-sensitive prion protein (rPrP-sen) comprising the amino acid sequence set forth as SEQ ID NO: 3 to make a reaction mix;
   (b) performing an amplification reaction comprising:
      (i) incubating the reaction mix at about 37° C. to permit formation of aggregates of the human rPrP-sen with the human PrP-res that may be present in the reaction mix, and maintaining incubation conditions that promote aggregation of the human rPrP-sen with the human PrP-res and results in a conversion of the human rPrP-sen to recombinant protease resistant prion protein initiated by the presence of prions (rPrP-res$^{(Sc)}$) while inhibiting development of spontaneously occurring recombinant prion protein (rPrP-res$^{(spon)}$);
      (ii) agitating aggregates formed during step (i), in shaking cycles, wherein each shaking cycle of the shaking cycles comprises a period of rest and a period of shaking, and wherein the period of rest and the period of shaking are substantially equal, wherein each shaking cycle is about 60 seconds in length, and wherein agitating is performed for about 48 hours in the absence of sonication;
   (c) detecting rPrP-res$^{(Sc)}$ in the reaction mix using fluorescence after agitating for about 48 hours as above, wherein detection of rPrP-res$^{(Sc)}$ in the reaction mix indicates that PrP-res was present in the sample.

* * * * *